United States Patent
Roe et al.

(10) Patent No.: US 6,517,856 B1
(45) Date of Patent: Feb. 11, 2003

(54) INSECTICIDE RESISTANCE ASSAY

(75) Inventors: R. Michael Roe, Apex, NC (US);
Woodward D. Bailey, Apex, NC (US);
Fred Gould, Raleigh, NC (US);
George G. Kennedy, Apex, NC (US);
Chester L. Sutula, Elkhart, IN (US)

(73) Assignees: Agdia Incorporated, Elkhart, IN (US);
North Carolina State University, Raleigh, NC (US)

( * ) Notice: Subject to any disclaimer, the term of this patent is extended or adjusted under 35 U.S.C. 154(b) by 0 days.

(21) Appl. No.: 09/567,319

(22) Filed: May 9, 2000

Related U.S. Application Data

(63) Continuation-in-part of application No. 09/112,274, filed on Jul. 8, 1998, now Pat. No. 6,060,039.

(51) Int. Cl.[7] ............................................. A01N 25/34

(52) U.S. Cl. .................. 424/410; 43/107; 43/121; 43/122; 43/123; 43/132.1; 119/6.5; 206/459.5; 220/23.83; 424/9.6; 424/93.1; 424/405; 424/409; 424/93.46; 426/1; 426/532; 514/29; 514/65

(58) Field of Search .................. 424/9.6, 84, 93.1, 424/409, 93.46, 410, 93.461, 93.462, 484–488, 405, DIG. 8; 514/29, 65, 68, 531, 120, 478, 631; 426/1, 532; 206/459.5, 524.1; 220/23.83, DIG. 10; 43/107, 121–125, 132.1; 119/6.5–6.7, 270

(56) References Cited

U.S. PATENT DOCUMENTS

| | | | |
|---|---|---|---|
| 4,988,510 A | 1/1991 | Brenner et al. ................ 424/84 |
| 5,139,031 A | 8/1992 | Guirguis ...................... 128/771 |
| 5,141,744 A | 8/1992 | Chang et al. .................. 424/93 |
| 5,172,514 A | * 12/1992 | Weber et al. ............... 43/132.1 |
| 5,246,936 A | 9/1993 | Treacy et al. ................ 514/256 |
| 5,716,831 A | 2/1998 | Whalon et al. ................ 435/19 |
| 5,763,245 A | 6/1998 | Greenplate et al. ...... 435/172.3 |
| 5,953,854 A | * 9/1999 | Hyatt .......................... 43/131 |
| 6,060,039 A | 5/2000 | Roe et al. ..................... 424/9.2 |

OTHER PUBLICATIONS

Bailey et al.; *Feeding disruption bioassay for species and Bacillus thuringiensis resistance diagnosis for Heliothis virescens and Helicoverpa zea in cotton* (Lepidoptera: Noctuidae), Crop Protection 17:7 591–598 (1998).

Cibulsky RJ and Ng SS; *Lepton HTK: A Diagnostic Test Kit To Improve Cotton Insect Control*, in: Proceedings Beltwide Cotton Conference, pp. 889–891. National Cotton Council, Memphis TN (Jan. 1996).

Gould et al.; *Feeding Behavior and Growth of Heliothis Virescens Larvae on Diets Containing Bacillus Thuringiensis Formulations or Endotoxins*, Entomologia Experimentalis et Applicata 58:3 199–210 (Mar. 1991).

Gould, Anderson, Jones et al., *Initial frequency of alleles for resistance to Bacillus thuringiensis toxins in field populations of Heliothis virescens*, Proc. Natl. Acad. Sci. USA., 94:3519–3523 (Apr. 1997).

Gould, Anderson, Reynolds et al.; *Selection and Genetic Analysis of a Heliothis virescens* (Lepidoptera: Noctuidae) *Strain with High Levels of Resistance to Bacillus thuringiensis Toxins*, J. Econ. Entomol., 88:1545–1559 (Dec. 1995).

(List continued on next page.)

Primary Examiner—Neil S. Levy
(74) Attorney, Agent, or Firm—Myers Bigel Sibley & Sajovec

(57) ABSTRACT

Methods of assaying insects for pesticide resistance and to identify insect species are based on feeding disruption caused by insecticide such as the biopesticide *Bacillius thuringiensis* toxin (Bt). Further provided are methods for monitoring insecticide resistance in a population of insects, as well as methods of screening compounds for insecticidal activity. Insecticide resistance can be assessed at the level of an individual insect or at population levels. Apparatus and dehydrated insect meal pads useful in such assays are described.

59 Claims, 31 Drawing Sheets

OTHER PUBLICATIONS

Figure 1A:
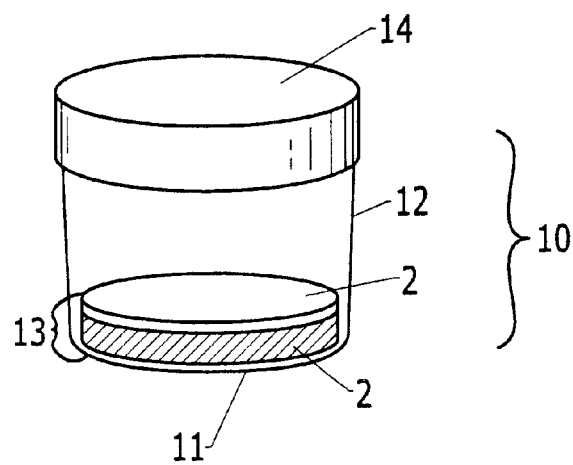

Hand et al.; *Activity of Different Formulations of Bacillus Thuringiensis on Lepidoptera in Cotton*: in Proc. of Beltwide Cotton Conferences, 908–911, National Cotton Council, Memphis, TN (Jan. 1996).

Jenkins, Parrott, McCarty et al., *Growth and Survival of Heliothis virescens* (Lepidoptera:Noctuidae) *on Transgenic Cotton Containing a Truncated form of the Delta Endotoxin Gene from Bacillus thuringiensis, J. Econ. Entomol.*, 86:181–185 (Feb. 1993).

Matsumura; *Toxicology of Insects*, 78–84, Plenum Press, New York (1975).

McGaughey and Whalon, *Managing Insect Resistance to Bacillus thuringiensis Toxins, Science*, 258:1451–1455 (Nov. 1992).

Nussinovitch et al.; *Compressive Characteristics of Freeze–Dried Agar and Alginate Gel Sponges*, Biotechnol. Prog. 9:101–104 (1993).

Parrott et al., *Feeding and Recovery of Gossypol and Tannin from Tobacco Budworm Larvae*, The Southwestern Entomologist 12:3 197–204 (Sep. 1987).

Ramachandran, Raffa, Miller et al., *Behavioral Responses and Sublethal Effects of Spruce Budworm* (Lepidoptera: Tortricidae) *and Fall Webworm* (Lepidoptera: Arctidae) *Larvae to Bacillus thuringiensis CrylA(a) Toxin in Diet, Environ–Entomol.*, 22:197–211 (Feb. 1993).

Raubenheimer et al.; *Hunger–thirst Interactions in the Locust, Locusta migratoria*, J. Insect Physiol. 40:7 631–639 (1994).

Rose, Barbhaiya, Roe et al., *Cytochrome P450–Associated Insecticide Resistance and the Development of Biochemical Diagnostic Assays in Heliothis virescens, Pestic. Biochem. Physiol.*, 51:178–191 (1995).

SIGMA catalog, p. 1447, Sigma Chemical Company (1989).

Sims et al.; *Monitoring Strategies for Early Detection of Lepidoptera Resistance to Bacillus thuringiensis Insecticidal Proteins*, Resistant Pest Management 9:1 21–24 (Summer 1997).

Tabashnik B.E., *Evolution of Resistance to Bacillus Thuringiensis, Annu. Rev. Entomol.*, 39:47–79 (1994).

Van Frankenhuyzen et al.; *Specificity of Activated CryIA Proteins From Bacillus thuringiensis subsp. kurstaki HD–1 for Defoliating Forest Lepidoptera*; Applied and Environmental Microbiology 57:6, 1650–1655 (Jun. 1991).

Williams et al.; *Combining ability in maize for fall armyworm and southwestern corn borer resistance based on a laboratory bioassay for larval growth*, Theor Appl Genet 90:275–278 (1995).

Bailey et al.; *Validation of Feeding Disruption Bioassays for Species Diagnosis and BT–Resistance Monitoring of Bollworm and Tobacco Budworm Field Populations*, Proceedings Beltwide Cotton Conferences 2000 (Jan. 2000).

Roe et al.; *Characterization of Spinosad (Tracer®) Resistance in a Laboratory Strain of the Tobacco Budworm and Development of Novel Diagnostics for Resistance Monitoring in the Field*, Proceedings Beltwide Cotton Conferences 2000 (Jan. 2000).

Roe et al.; *Detection of Resistant Insects and IPM*, Proceedings of a Conference 67–85 (Mar. 1999).

Roe et al.; *Assay Kit for Species and Insecticide Resistance Diagnosis for Tobacco Budworm and Bollworm in Cotton*, Proceeding Beltwide Cotton Conference 1999.

Rohitha et al. "Freeze–Dried Artificial Diet–Based Technique for Screening Plant Extracts Against *Epiphyas Postvittana* (Lepidoptera: Tortricidae)," *Journal of Economic Entomology*. (Dec. 1995) vol. 88, No. 6, pp. 1566–1569.

Singh, Pritam. "A General Purpose Laboratory Diet Mixture for Rearing Insects," *Insect Sci. Application*. (1983) vol. 4, No. 4, pp. 357–362.

International Search Report corresponding to PCT/US01/14284; mailing date Nov. 1, 2001.

* cited by examiner

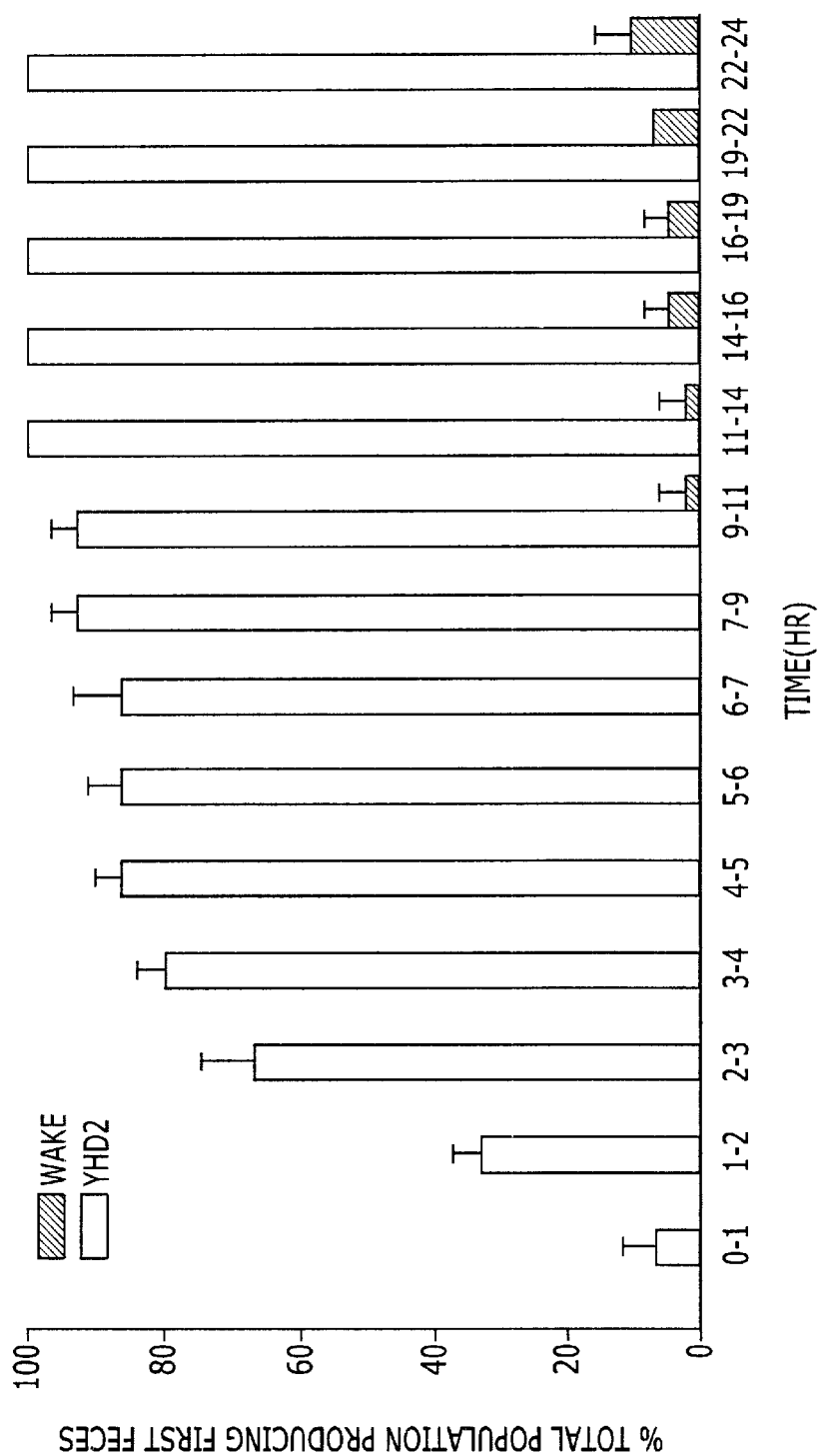

FECAL PELLETS PRODUCED IN 24 HR

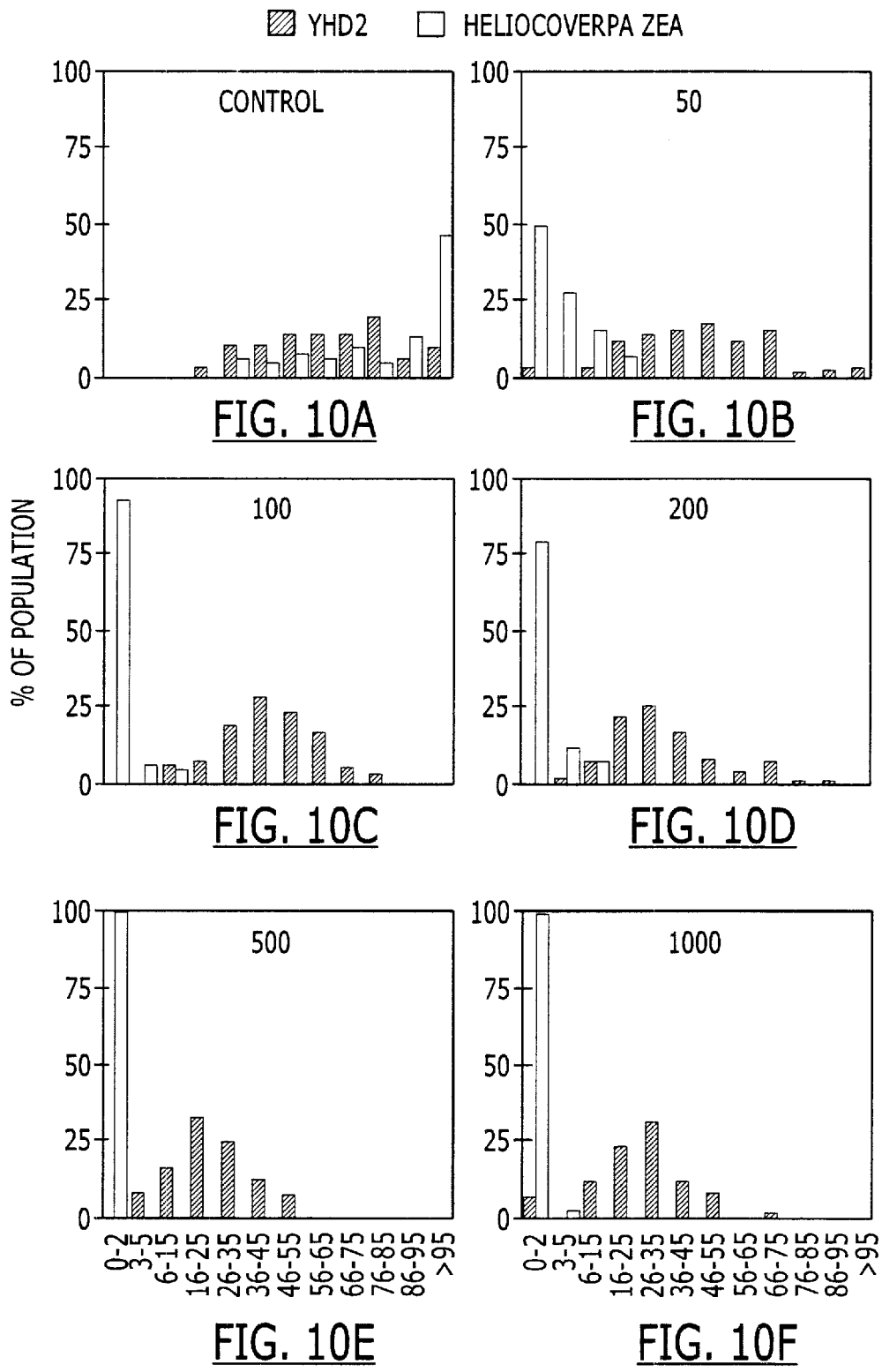
FECAL PELLETS PRODUCED IN 24 HR

INSECTICIDE RESISTANCE ASSAY

RELATED APPLICATION INFORMATION

This application is a continuation-in-part of U.S. application Ser. No. 09/112,274, filed Jul. 8, 1998, now U.S. Pat. No. 6,060,039 the disclosure of which is incorporated herein by reference in its entirety.

This invention was made with Government support under grant USDA NRI-CGP 94-37302-0501. The Government may have certain rights to this invention

FIELD OF THE INVENTION

The present invention relates to methods of testing insects for resistance to pesticides, and in particular to rapid bioassay methods for testing insect resistance to *Bacillus thuringiensis* (Bt), spinosyns (e.g., spinosad), and pyrethroid insecticides. The present invention further relates to assays for the identification of insect species based on resistance or susceptibility to insecticides, and in particular to a method of distinguishing larvae of *Helicoverpa zea* and *Heliothis virescens*. The present invention further relates to methods of screening compounds for insecticidal activity. The present invention further relates to dehydrated insect meal pads and containers for carrying out the inventive methods.

BACKGROUND OF THE INVENTION

The bacterium *Bacillus thuringiensis* (Bt) contains genes encoding insecticidal proteins. Bt proteins are toxic when ingested by susceptible insect and insect larvae. Bt proteins are used commercially in pesticide formulations, and transgenic crop plants expressing the Bt gene are widely cultivated. The Bt gene codes for a protein toxin that attacks the insect midgut, stops feeding and eventually kills susceptible insects. Gill et al., *Annu. Rev. Entomol.* 37:615 (1992); Fischhoff, In *Biotechnology and Integrated Pest Management*, Ed. G J Persley, pp. 214–227, CAB International, Cambridge, UK.

Several hundred strains of *Bacillus thuringiensis* exist, with considerable specificity toward various groups of insects such as the lepidoptera (butterflies and moths), coleoptera (beetles) and/or diptera (mosquitoes), as well as toward nematodes. There is a species specificity of the interaction between Bt toxin and the membranes of insect gut cells. The Bt toxin of a particular *B. thuringiensis* strain may bind to the gut of lepidopteran larvae, or only some species of lepidopteran larvae, but not to others. Binding of the protein to the membrane is required for its toxic effects. Thus the Bt toxins have a high specificity for a small number of pest species, while having no significant activity against beneficial insects, wildlife or humans. Lambert and Peferoen, *BioScience*, 42:112 (1992); Gill et al., *Annu. Rev. Entomol.* 37:615 (1992); Meadows, In: *Bacillus thuringiensis, An Environmental Biopesticide: Theory and Practice*, Entwistle et al., Eds., pp. 193–200 (1993).

Formulations of Bt toxin for use as insecticides are known in the art. See, e.g., U.S. Pat. No. 5,747,450; U.S. Pat. No. 5,250,515; U.S. Pat. No. 5,024,837; U.S. Pat. No. 4,797,276; and U.S. Pat. No. 4,713,241.

Plants transformed to carry the Bt gene and express insecticidal proteins are known in the art, and include potato, cotton, tomato, corn, tobacco, lettuce and canola. Krimsky and Wrubel, *Agricultural Biotechnology: An Environmental Outlook*, Tufts University, Department of Urban and Environmental Policy, p. 29 (1993). See also U.S. Pat. No. 5,608,142; U.S. Pat. No. 5,495,071; U.S. Pat. No. 5,349,124; and U.S. Pat. No. 5,254,799. The use of such genetically engineered plants is expected to reduce the use of broad spectrum insecticides. Gasser and Fraley, *Science* 244:1293 (1989).

The use of pesticides results in the selection of individuals resistant to the pesticide, and can lead to the development of pesticide-resistant populations. Resistance to chemical insecticides such as organochlorines, organophosphates, carbamates, spinosyns and pyrethroids is known. Laboratory and field evidence documents that many pests are capable of evolving high levels of resistance to a number of commonly used Bt toxins. Tabashnik, *Annu. Rev. Entomol.* 39:47 (1994); Tabashnik, *J. Econ. Entomol.* 83:1671 (1990); Bauer, *Fla. Ent.* 78:414 (1995); Gould, *Proc. Natl. Acad Sci. USA* 94:3519 (1997). Resistance may evolve whether the Bt is applied to plants or the plants are genetically engineered to express Bt. The development of resistance to Bt toxin-expressing crops may also result in resistance to commercial formulations of fermented strains of Bt, such as DIPEL® (Abbott Laboratories).

A further concern in the use of plants genetically engineered to express Bt toxins is the difficulty of distinguishing between different pest species that will and will not be controlled by Bt. The presence of a pest in the field that is resistant to Bt indicates the need for supplemental pesticide treatments, whereas no additional treatment is needed if pests are susceptible to Bt. In the case of cotton, transgenic Bt cultivars are exceptionally toxic to most strains of the tobacco budworm *Heliothis virescens* (F.) (Lepidoptera: Noctuidae) (Jenkins et al., *J. Econ. Entomol.* 86:181 (1993)), but are less toxic to the bollworm *Helicoverpa zea* (Boddie) (Lepidoptera:Noctuidae) (Lambert et al., In: *Proceedings Beltwide Cotton Conference*, pp. 931–935, National Cotton Council, Memphis, Tenn. (1996)). *H. zea* and *H. virescens* are found in the same geographic areas, and in years when *H. zea* populations are high, larva that are not killed by ingestion of Bt can cause significant damage to cotton. The eggs and young larvae of *H. zea* and *H. virescens* are indistinguishable by simple observation in the field (although adults are readily distinguished visually). Without a test to distinguish among susceptible and relatively more tolerant species, farmers finding lepidopteran eggs or neonates on cotton cannot rely on Bt cotton for control of lepidopteran pests.

Rapid, reliable methods to distinguish Bt-susceptible from Bt-resistant species, and to detect the development of Bt resistance, as well as resistance to other insecticides, in populations of insects, are desirable. The methods of the present invention provide a bioassay capable of distinguishing between *H. virescens* and *H. zea*. The present methods can also detect insect resistance to Bt, and other insecticides, within a species. The present invention further provides a bioassay for screening compounds to identify those with insecticidal activity.

SUMMARY OF THE INVENTION

Accordingly, one aspect of the present invention is a dehydrated insect meal pad comprising a gel matrix and insect meal. In preferred embodiments, the gel matrix comprises agar. In particular preferred embodiments, the meal pad further comprises an insecticide or a compound to be screened for insecticidal activity and a marker compound (e.g., Trypan Blue). Preferred insecticides include Bt toxin and spinosyns.

As a further aspect, the present invention provides a container for housing insects, comprising: (a) a chamber having a floor, sidewalls extending from said floor and an open end portion; (b) a seal member removably attached to the container and configured to close the open end portion; and (c) a dehydrated insect meal pad contained with the chamber, as described above. In preferred embodiments, the floor of the container is permeable to liquids.

As a further aspect, the present invention provides a kit for testing insects for resistance to an insecticide that causes feeding disruption, comprising: (a) one or more containers sized to house at least one of the insects; (b) a dehydrated meal pad comprising a test diet comprising the insecticide; (c) printed instructions setting forth (i) a method for rehydrating the meal pad prior to use, and (ii) a diagnostic time period and a diagnostic amount of feces that indicates the insects are resistant to the insecticide to be tested.

Another aspect of the invention is a kit for screening a test compound for insecticidal activity as indicated by feeding disruption, comprising: (a) one or more containers sized to house at least one insect; (b) a dehydrated meal pad comprising a test diet comprising the test compound; (c) printed instructions setting forth a method for (i) rehydrating the meal pad prior to use, and a diagnostic time period and (ii) a diagnostic amount of feces that indicates the test compound exhibits insecticidal activity.

As still a further aspect the present invention provides a method of detecting in a plurality of insect larvae with the visual appearance of *H. virescens* larvae, the presence of *H. zea* larvae, comprising: (a) giving each of the larvae access to an insect meal pad of the invention for a predetermined time, wherein the meal pad has been rehydrated and further wherein the meal pad comprises a test diet containing a predetermined diagnostic amount of *Bacillus thuringiensis* toxin, and (b) assessing the amount of feces produced by each of the larvae over said predetermined time, wherein any larva producing more than a predetermined diagnostic amount of feces are *H. zea*.

As another aspect, the present invention provides a method of detecting, in one or more insects, the presence of an insect(s) resistant to an insecticide that causes feeding disruption in susceptible insects, comprising: (a) giving the one or more insects access to a meal pad according to the invention for a predetermined time, wherein the meal pad has been rehydrated and further wherein the meal pad comprises a test diet containing a predetermined diagnostic amount of said insecticide; and (b) assessing the amount of feces produced by the one or more insects over the predetermined time; wherein the amount of feces produced by the one or more insects is indicative of the presence of an insect(s) resistant to the insecticide.

Also provided herein is a method of identifying a compound that has insecticidal activity against a species of insect, comprising: (a) providing one or more insects from a species; (b) giving the one or more insects access to a meal pad of the invention for a predetermined time, wherein the meal pad has been rehydrated and further wherein the meal pad comprises a test diet containing a test compound to be screened for insecticidal activity; and (c) assessing the amount of feces produced by the one or more insects over the predetermined time; wherein the amount of feces produced by said one or more insects is indicative of the presence of an insect(s) resistant to the insecticide.

The feeding disruption assays described herein may be qualitative (i.e., detect the presence or absence of feces) or quantitative (i.e., count, measure, weight the feces, or the like) in nature. The feeding disruption assays of the invention are suitable for field or laboratory use. In particular preferred embodiments, the methods are used in high throughput methods employing automated imaging devices.

These and other aspects of the invention are set forth in more detail in the description of the invention that follows.

BRIEF DESCRIPTION OF THE DRAWINGS

FIG. 1A is a perspective view of apparatus for conducting the feeding disruption assays of the present invention.

FIG. 1B is a cross-section of apparatus for conducting the feeding disruption assays of the present invention, where the apparatus contains a perforated floor.

FIG. 1C is a perspective view of apparatus for conduction the feeding disruption assays of the present invention, wherein the ceiling of the container has a hole or aperture formed therein to allow placement of insects within the container.

FIG. 1D is a perspective view of a meal pad cover suitable for use with the apparatus as shown in FIG. 1A, 1B or 1C.

FIG. 2A is a cross-sectional view of an apparatus containing a cylindrical annular ring providing a platform surface. The interior of the cylinder is filled with an insect meal pad that is accessible to an insect placed within the container.

FIG. 2B is a cross-sectional view of an apparatus of the invention. The apparatus differs from that shown in FIG. 2A in that the interior space within the cylindrical annular ring is expanded at the bottom to form a funnel shape.

FIG. 3 is a cross-section of an apparatus for conducting the feeding disruption assays of the present invention, where the meal pad is deposited as a small disk or lens on the floor of the container.

FIG. 4A is an exploded view of an apparatus for conducting the feeding disruption assays of the present invention, where a plurality of individual containers have been affixed together.

FIG. 4B is a cross-section of a preferred apparatus for conducting the feeding disruption assays of the invention.

FIG. 4C is a perspective view of the upper well layer from the apparatus of FIG. 4B.

FIG. 5A is a perspective view of a multi-chambered plate in which there is a depression or well formed in the bottom of each container. A flat platform surface is formed around the perimeter of each well, on which insects can walk and deposit feces.

FIG. 5B is a cross-sectional view of a single container from the multi-chambered plate of FIG. 5A. The well formed within the container is filled with an insect meal pad.

FIG. 6A graphs the effect of different concentrations of CryIAc on the production of fecal pellets by third instars of the YHD2 strain of the tobacco budworm, *H. virescens*. CryIAc was placed in Trypan Blue diet in concentrations of 0.000 μg/ml diet (solid diamonds); 0.008 μg/ml diet (solid triangles); 0.016 μg/ml diet (open triangles); 0.032 μg/ml diet (squares); and 0.064 μg/ml diet (circles). Each treatment represents the average of three replicates of 15 insects per replicate. Error bars are ±1 SE, which in most cases does not exceed the size of the graph symbol.

FIG. 6B graphs the effect of different concentrations of CryIAc on the production of fecal pellets by third instars of the YHD2×Wake strain of the tobacco budworm, *H. virescens*. CryIAc was placed in Trypan Blue diet in concentrations of 0.000 μg/ml diet (open circles); 0.004 μg/ml diet (solid diamonds); 0.008 μg/ml diet (solid triangles); 0.016 μg/ml diet (open triangles); 0.032 μg/ml diet (squares); and 0.064 µg/ml diet (solid circles). Each treatment represents the average of three replicates of 15 insects per replicate. Error bars are ±1 SE, which in most cases does not exceed the size of the graph symbol.

Figure 6A:
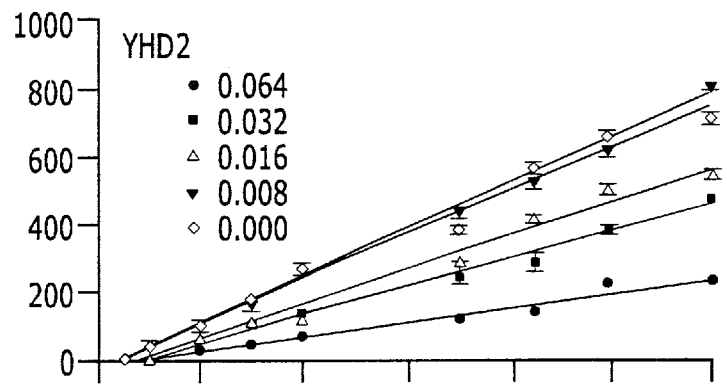
Figure 6B:
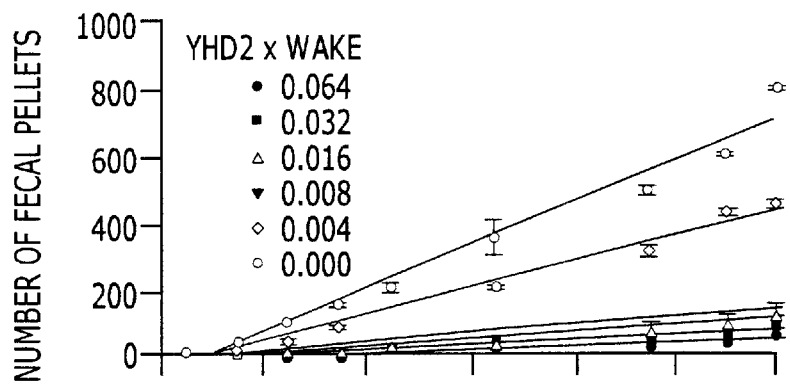
Figure 6C:
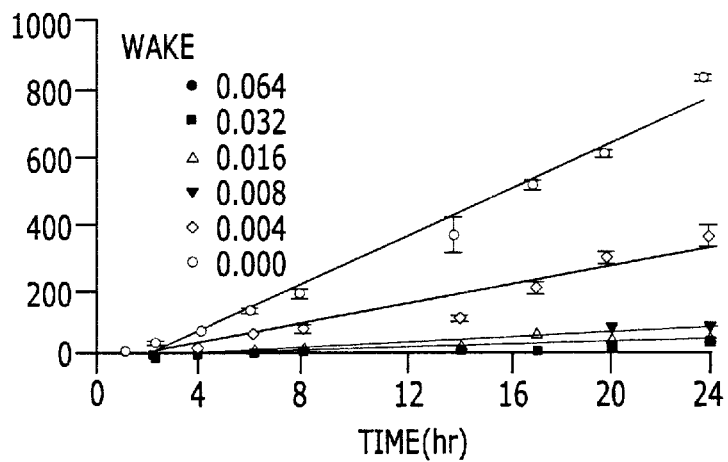

FIG. 6C graphs the effect of different concentrations of CryIAc on the production of fecal pellets by third instars of the Wake strain of the tobacco budworm, *H. virescens*. CryIAc was placed in Trypan Blue diet in concentrations of 0.000 µg/ml diet (open circles); 0.004 µg/ml diet (solid diamonds); 0.008 µg/ml diet (solid triangles); 0.016 µg/ml diet (open triangles); 0.032 µg/ml diet (squares); and 0.064 µg/ml diet (solid circles). Each treatment represents the average of three replicates of 15 insects per replicate. Error bars are ±1 SE, which in most cases does not exceed the size of the graph symbol. Fecal production was minimal at concentrations>0.004 µg CryIAc/ml diet, preventing separate plots for each data set.

Figure 7:
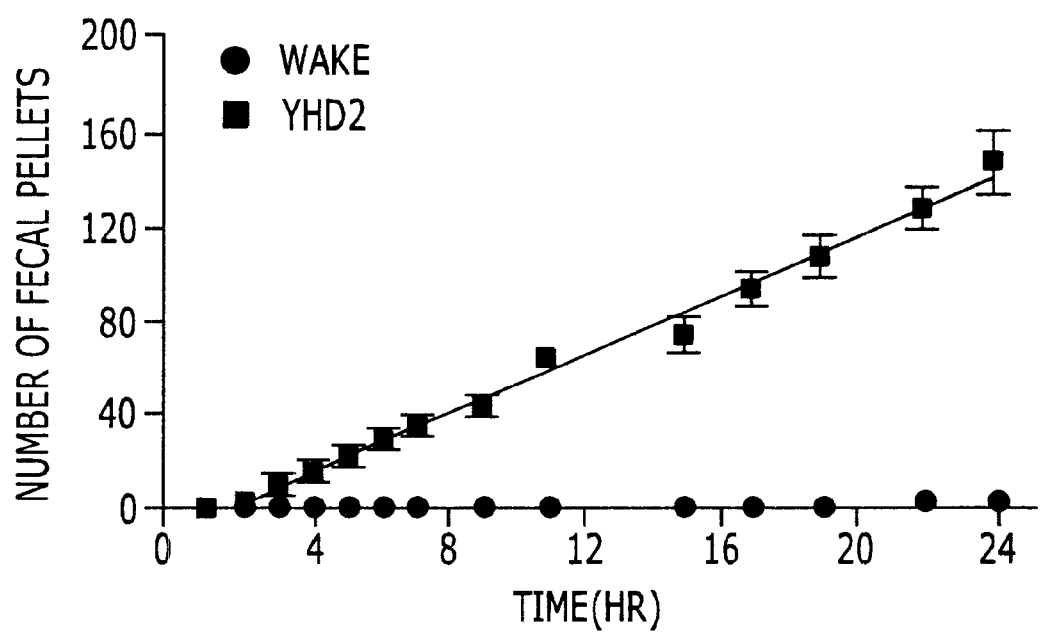

FIG. 7 graphs the effect of 0.032 µg CryIAc/mi of Trypan Blue diet on fecal pellet production by Wake (circles) and YHD2 (squares) third instars previously reared on cotton. Each treatment is the average of three replicates of 15 insects per replicate. Error bars are ±1 SE, which in most cases does not exceed the size of the graph symbol.

FIG. 8 graphs the percentage of the total population of Wake (shaded bars) versus YHD2 (open bars) third instars producing the first blue fecal pellet at different time intervals after the larvae were transferred to the surface of the CryIAc-Trypan Blue diet (0.032 µg CryIAc/ml). Each treatment is the average of three replicates of 15 insects per replicate. Error bars are ±1 SE, which in most cases does not exceed the size of the graph symbol.

Figure 9A:
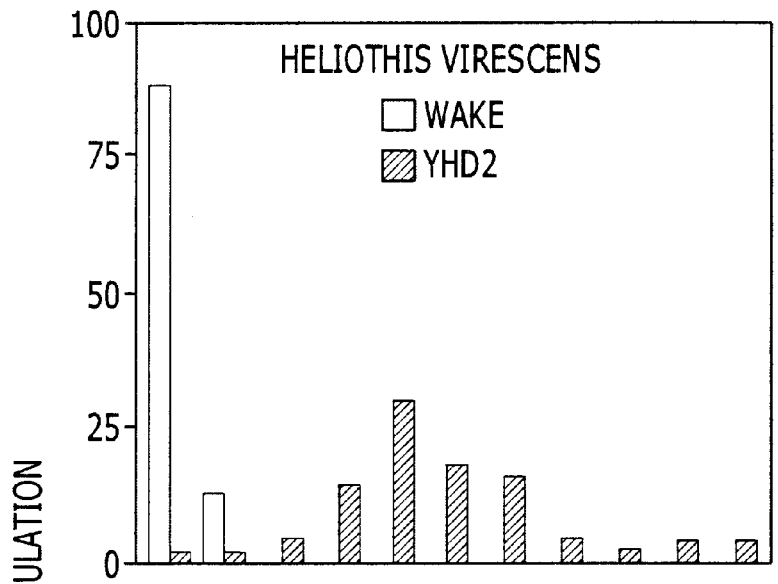

FIG. 9A graphs the percentage of the test population producing blue fecal pellets as neonates in 24 hours on CryIAc-Trypan Blue diet (0.032 µg CryIAc/ml), where shaded bars represent YHD2 larvae and open bars represent Wake larvae. Results were taken from two replicates consisting of 25 insects per replicate for each species and strain.

Figure 9B:
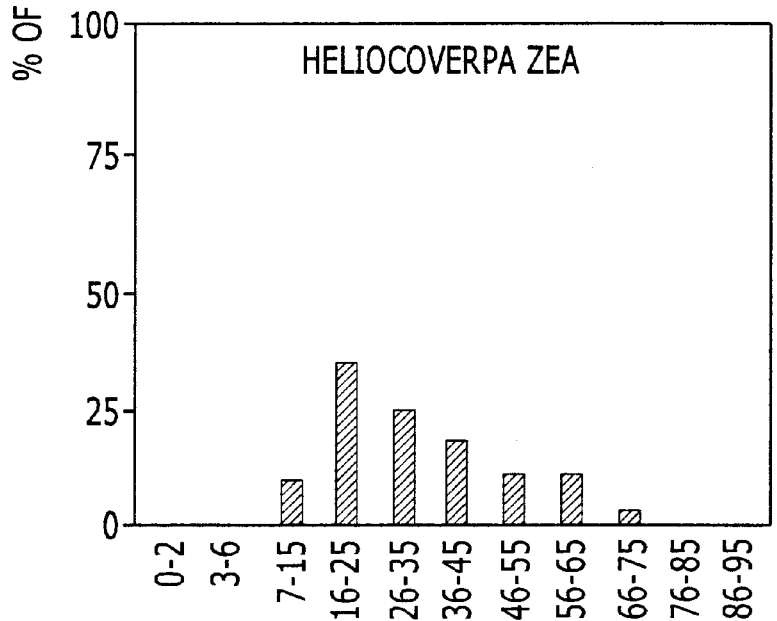

FIG. 9B graphs the percentage of the test population of *Helicoverpa zea* producing blue fecal pellets as neonates in 24 hours on CryIAc-Trypan Blue diet (0.032 µg CryIAc/mi). Results were taken from two replicates consisting of 25 insects per replicate for each species and strain.

FIG. 10A graphs the percentage of the test population of YHD2 (shaded bars) and *Helicoverpa zea* (open bars) neonates producing blue fecal pellets over 24 hours on Trypan Blue diet containing no CryIAc toxin. The results were taken from two replicates of 25 insects per replicate for each species.

FIG. 10B graphs the percentage of the test population of YHD2 (shaded bars) and *Helicoverpa zea* (open bars) neonates producing blue fecal pellets over 24 hours on Trypan Blue diet containing 50 µg CryIAc/ml diet. The results were taken from two replicates of 25 insects per replicate for each species.

FIG. 10C graphs the percentage of the test population of YHD2 (shaded bars) and *Helicoverpa zea* (open bars) neonates producing blue fecal pellets over 24 hours on Trypan Blue diet containing 100 µg CryIAc/ml diet. The results were taken from two replicates of 25 insects per replicate for each species.

FIG. 10D graphs the percentage of the test population of YHD2 (shaded bars) and *Helicoverpa zea* (open bars) neonates producing blue fecal pellets over 24 hours on Trypan Blue diet containing 200 µg CryIAc/ml diet. The results were taken from two replicates of 25 insects per replicate for each species.

FIG. 10E graphs the percentage of the test population of YHD2 (shaded bars) and *Helicoverpa zea* (open bars) neonates producing blue fecal pellets over 24 hours on Trypan Blue diet containing 500 µg CryIAc/ml diet. The results were taken from two replicates of 25 insects per replicate for each species.

FIG. 10F graphs the percentage of the test population of YHD2 (shaded bars) and *Helicoverpa zea* (open bars) neonates producing blue fecal pellets over 24 hours on Trypan Blue diet containing 1000 µg CryIAc/ml diet. The results were taken from two replicates of 25 insects per replicate for each species.

Figure 11:
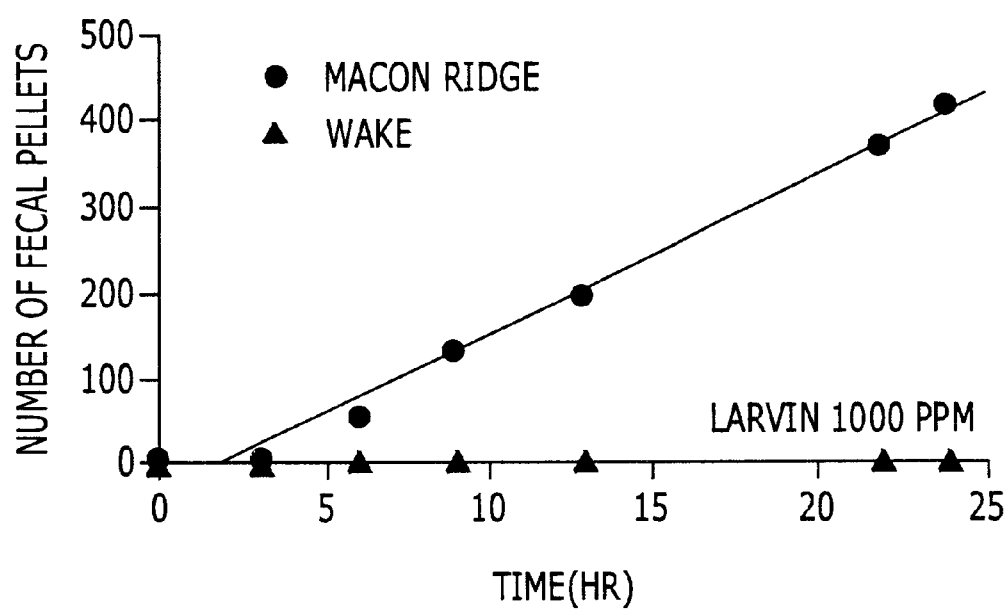

FIG. 11 graphs the number of fecal pellets produced over time by two strains of *H. virescens* exposed to a test diet containing a carbamate insecticide (LARVIN®). One strain (Macon Ridge; closed circles) was resistant to the insecticide; the other strain (Wake; closed triangles) was susceptible.

Figure 12:
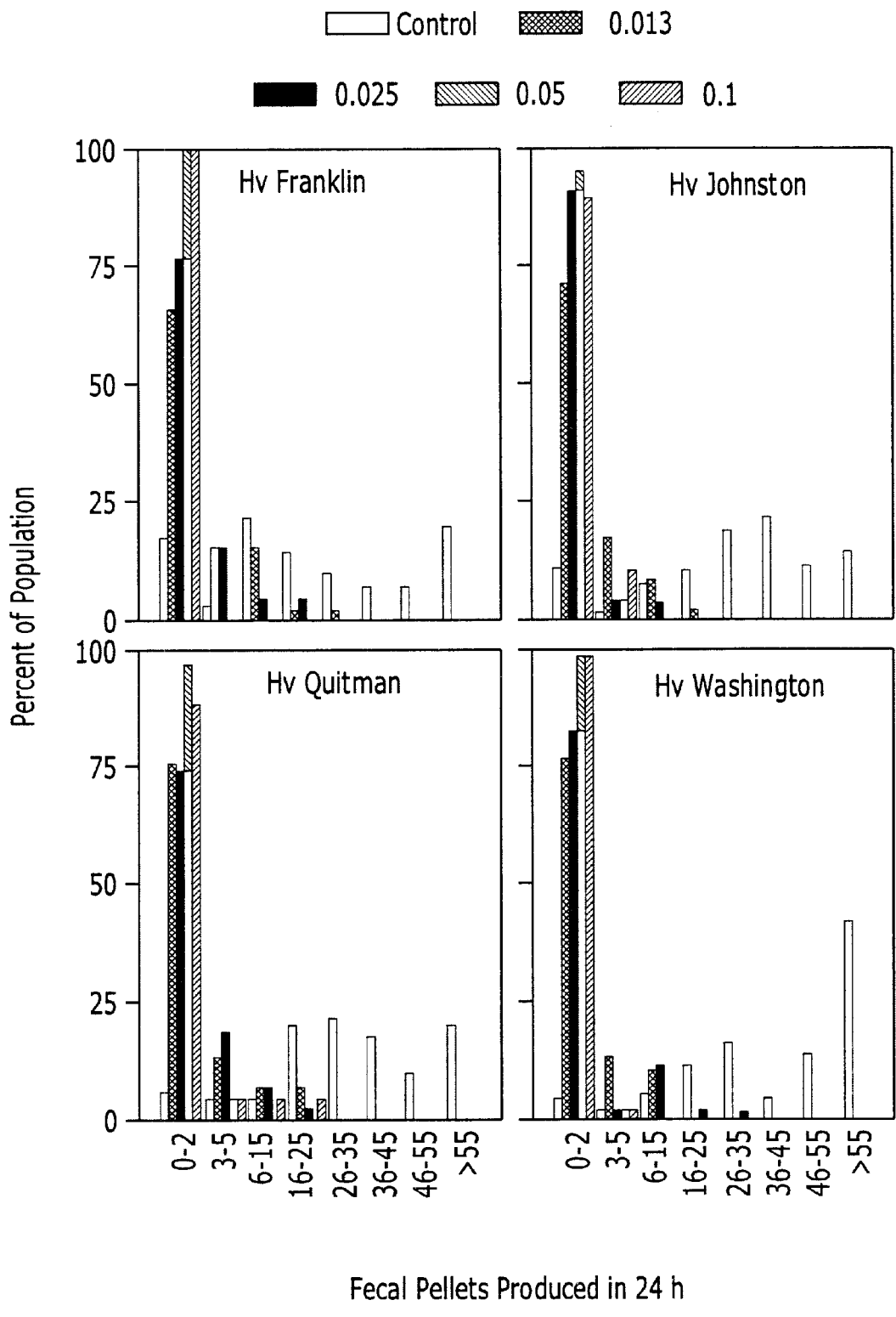

FIG. 12 graphs the percentage of *H. virescens* populations producing fecal pellets in neonates in 24 h on MVP-hydrated meal pads. Each bar represents the response at a particular dose, given as µg MVP per ml hydrated diet. The results were taken from two replicates consisting of 24 insects per replicate for each strain at each dose. No-dose controls were replicated three times.

Figure 13:
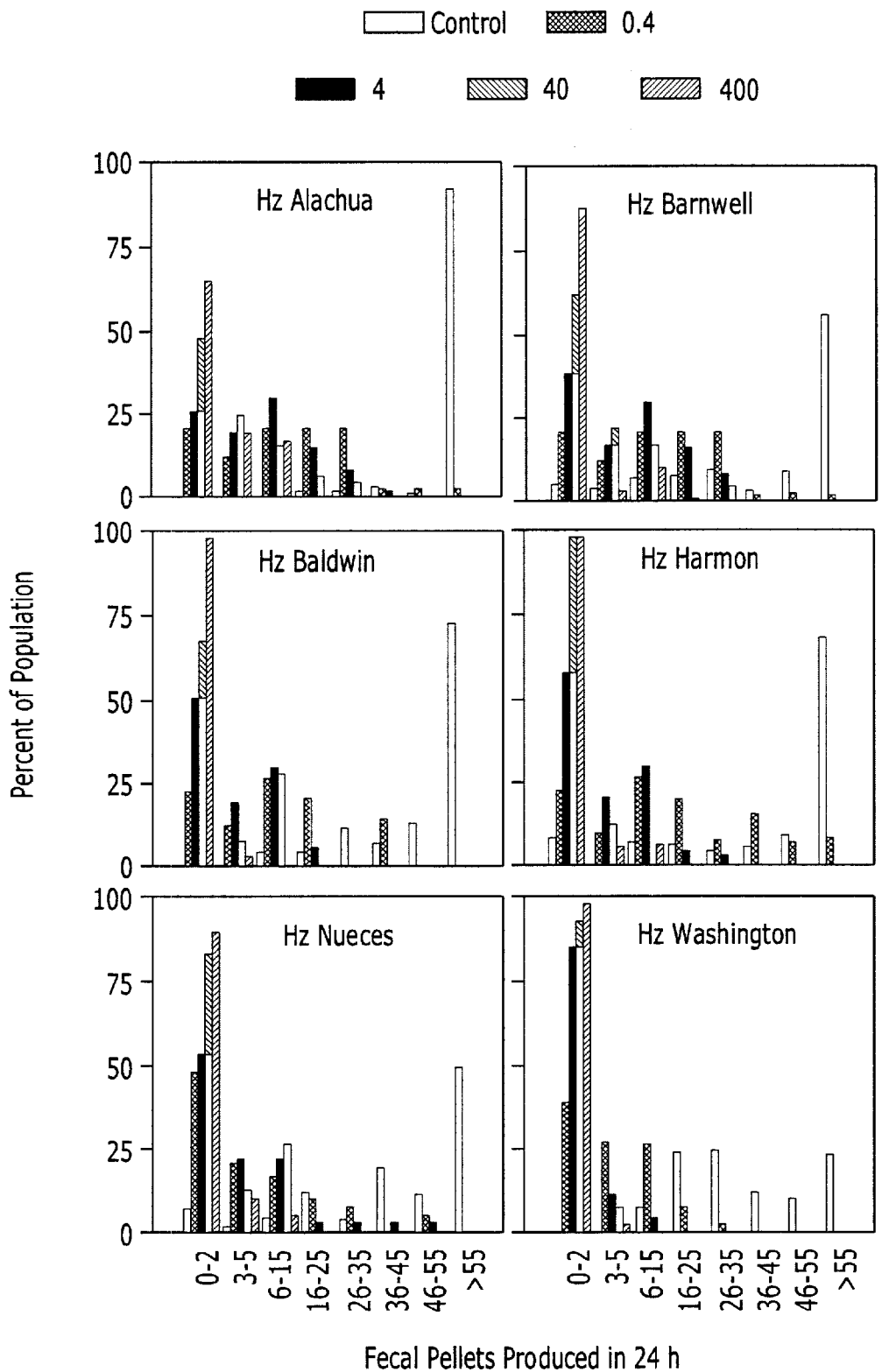

FIG. 13 graphs the percentage of *H. zea* populations producing fecal pellets in neonates in 24 h on MVP-hydrated meal pads. Each bar represents the response at a particular dose, given as µg MVP per ml hydrated diet. The results were taken from two replicates consisting of 24 insects per replicate for each strain at each dose. No-dose controls were replicated three times.

Figure 14:
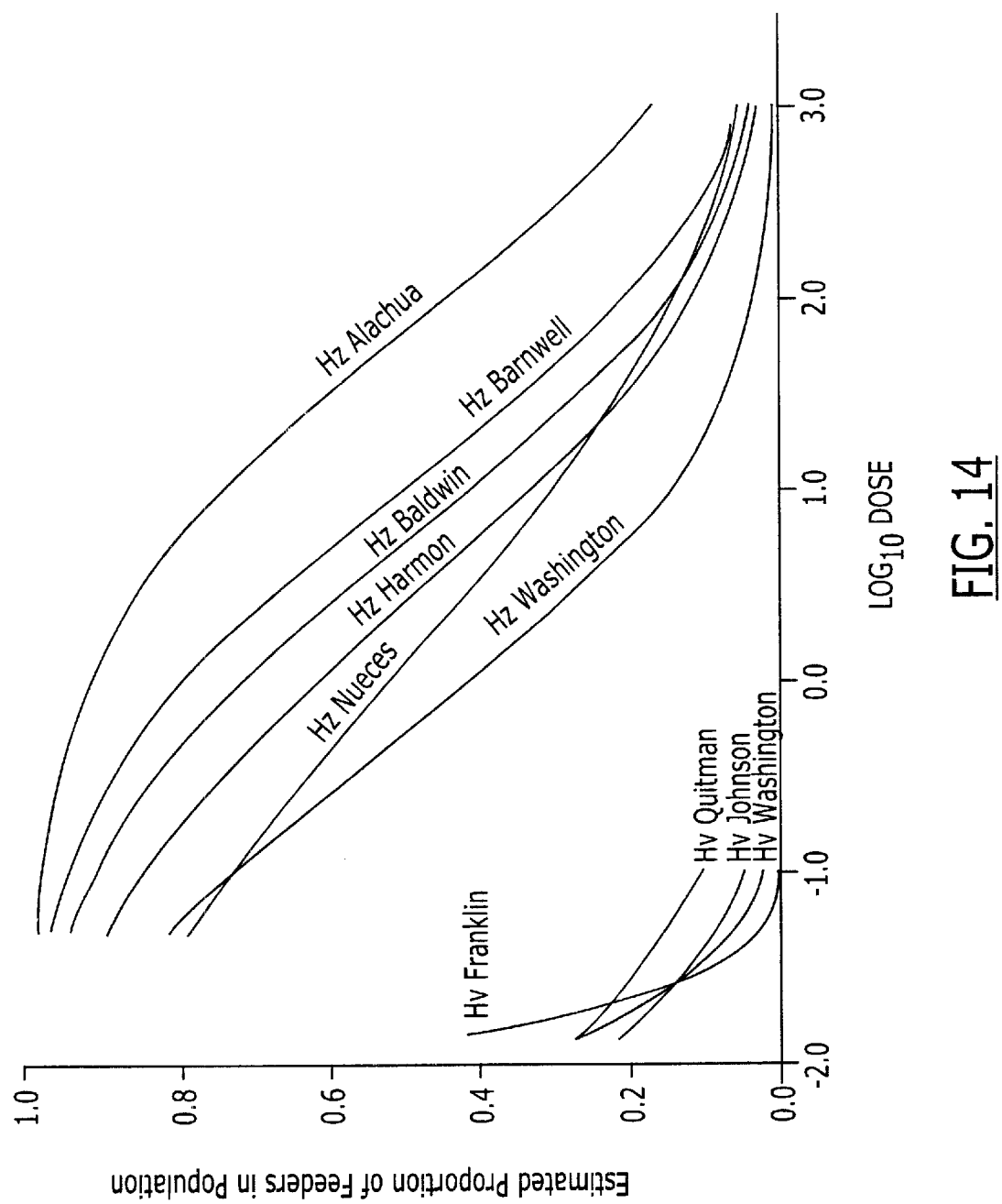

FIG. 14 presents Probit curves relating the proportion of nonfeeders ($\leq 2$ fecal pellets per larva) to $\log_{10}$ dose. Probit analyses were applied to results taken from two replicates consisting of 24 insects per replicate for each strain.

Figure 15:
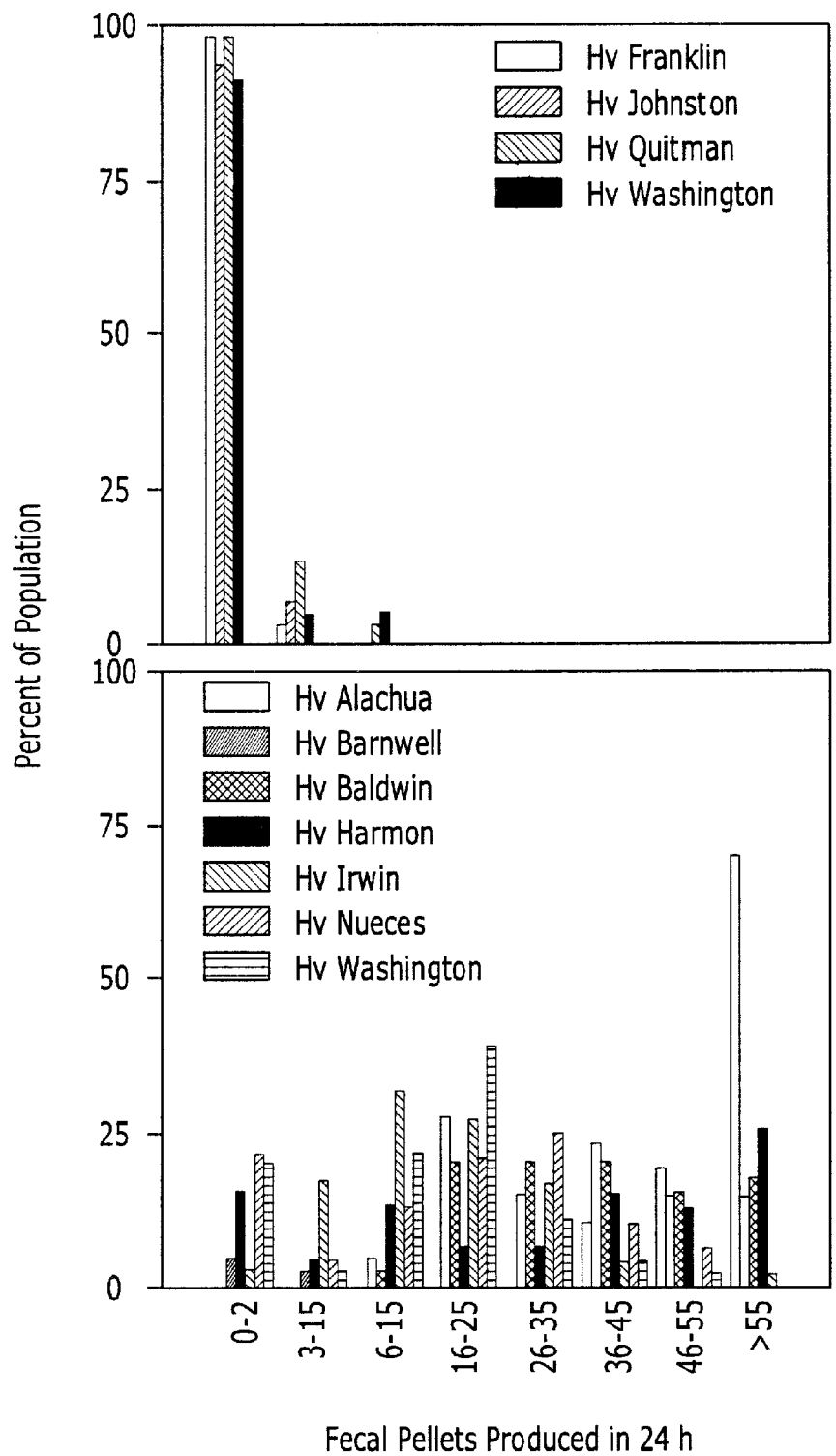

FIG. 15 graphs the percentage of *H. virescens* and *H. zea* populations producing fecal pellets as neonates in 24 h on MVP-hydrated meal pads, concentration=0.04 µg MVP per ml hydrated diet. The results were taken from two replicates consisting of 24 insects per replicate for each strain.

Figure 16:
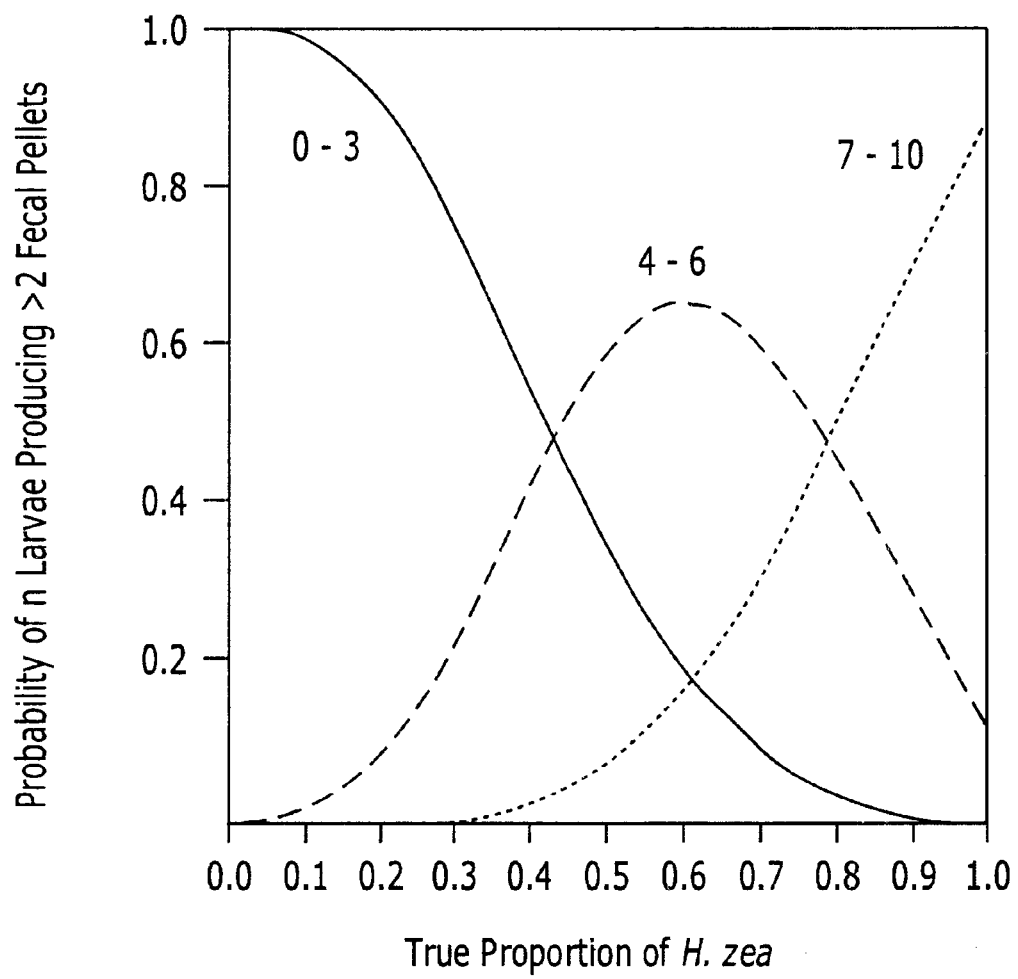

FIG. 16 shows the relationship between the true proportion of *H. zea* in a population and the probability of a sample of ten randomly sampled larvae containing n feeders. Probability curves were derived assuming a binomial model where the probability of feeding (>2 fecal pellets at 24 h; diagnostic concentration=0.04 µg MVP per ml diet) by individual larvae is a function of the actual percentage of *H. zea* in the population. Calculations are based on a diagnostic dose feeding likelihood of 0.8 and 0.02 for *H. zea* and *H. virescens*, respectively, so that the curves represent conservative estimates. Probabilities are summed for the presence of 0–3, 4–6, and 7–10 feeders in a sample of n=10.

Figure 17:
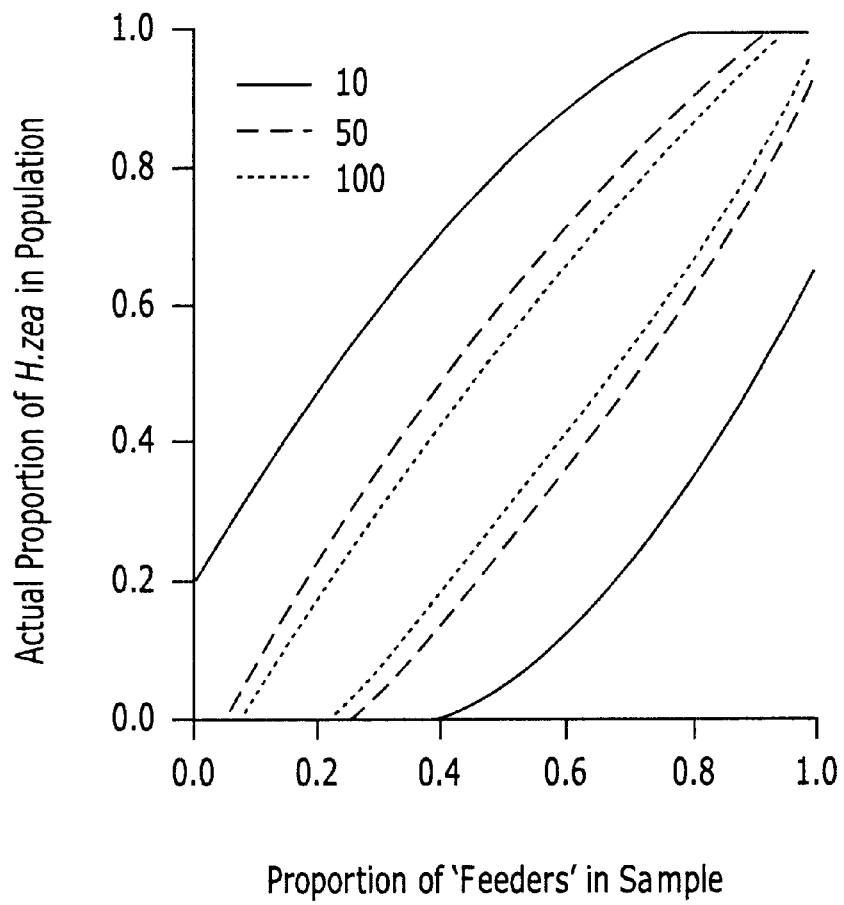

FIG. 17 demonstrates the accuracy of assay predictions using insects from southern Georgia. The proportion of feeders (larvae producing >2 fecal pellets over 24 h at a diagnostic concentration of 0.04 µg MVP per ml diet) in the bioassay is used to predict the actual proportion of *H. zea* in the population. Prediction accuracy, as represented by 95% confidence intervals, is presented for sample sizes of n=10, 50 and 100 randomly sampled larvae. Feeding probabilities for both species were assigned based on those observed in insects from south Georgia, where ps=0.15 and pr=0.98.

Figures 18A, 18B:
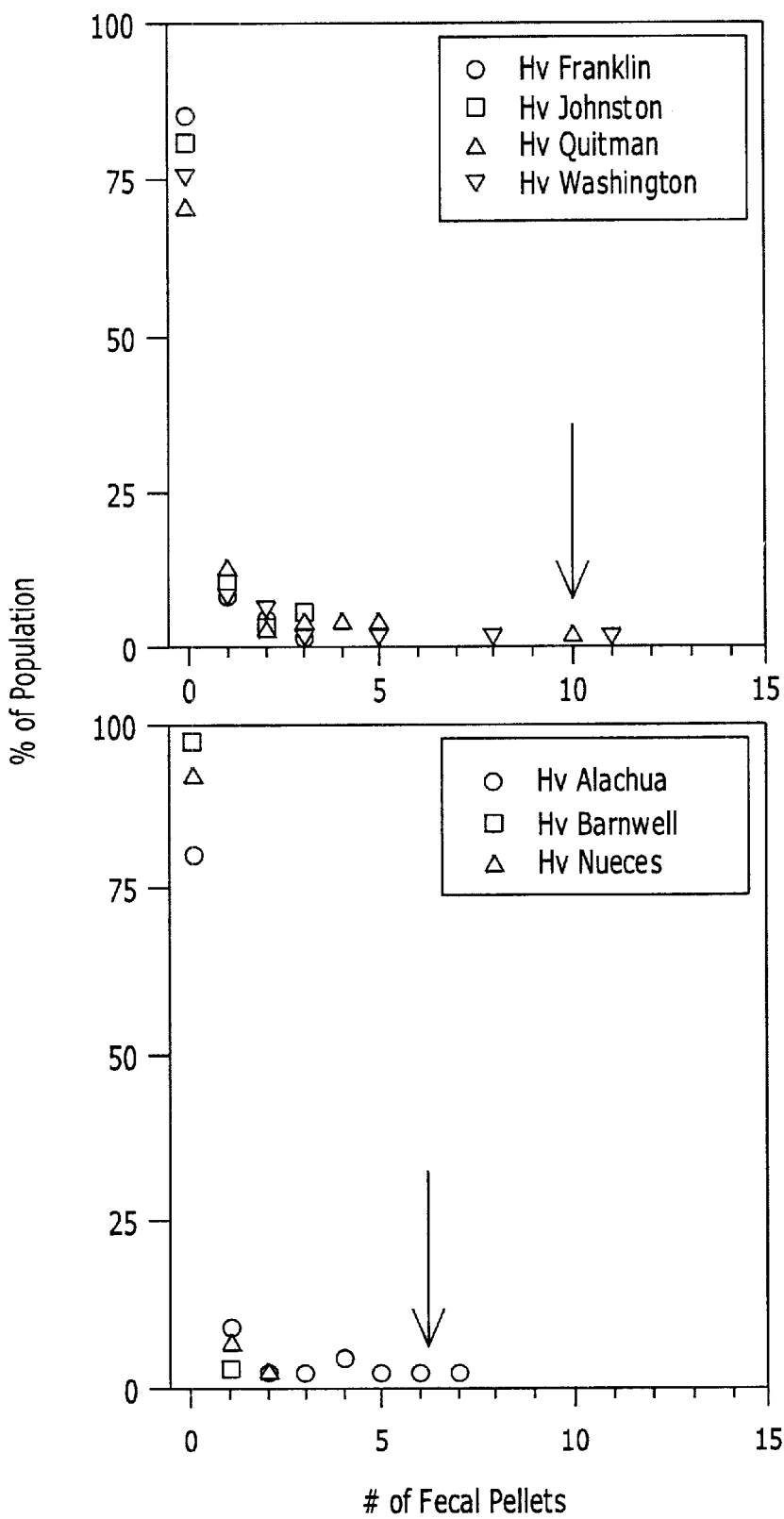

FIG. 18A graphs the frequency distribution of cumulative fecal production at 24 h for *H. virescens* (diagnostic concentration=0.04 µg MVP per ml diet). Arrows denote the fecal number at which <1.0% of the population produced additional feces.

FIG. 18B graphs the frequency distribution of cumulative fecal production at 24 h for *H. zea* (diagnostic concentration=1200 μg MVP per ml diet). Arrows denote the fecal number at which <1.0% of the population produced additional feces.

Figure 19:
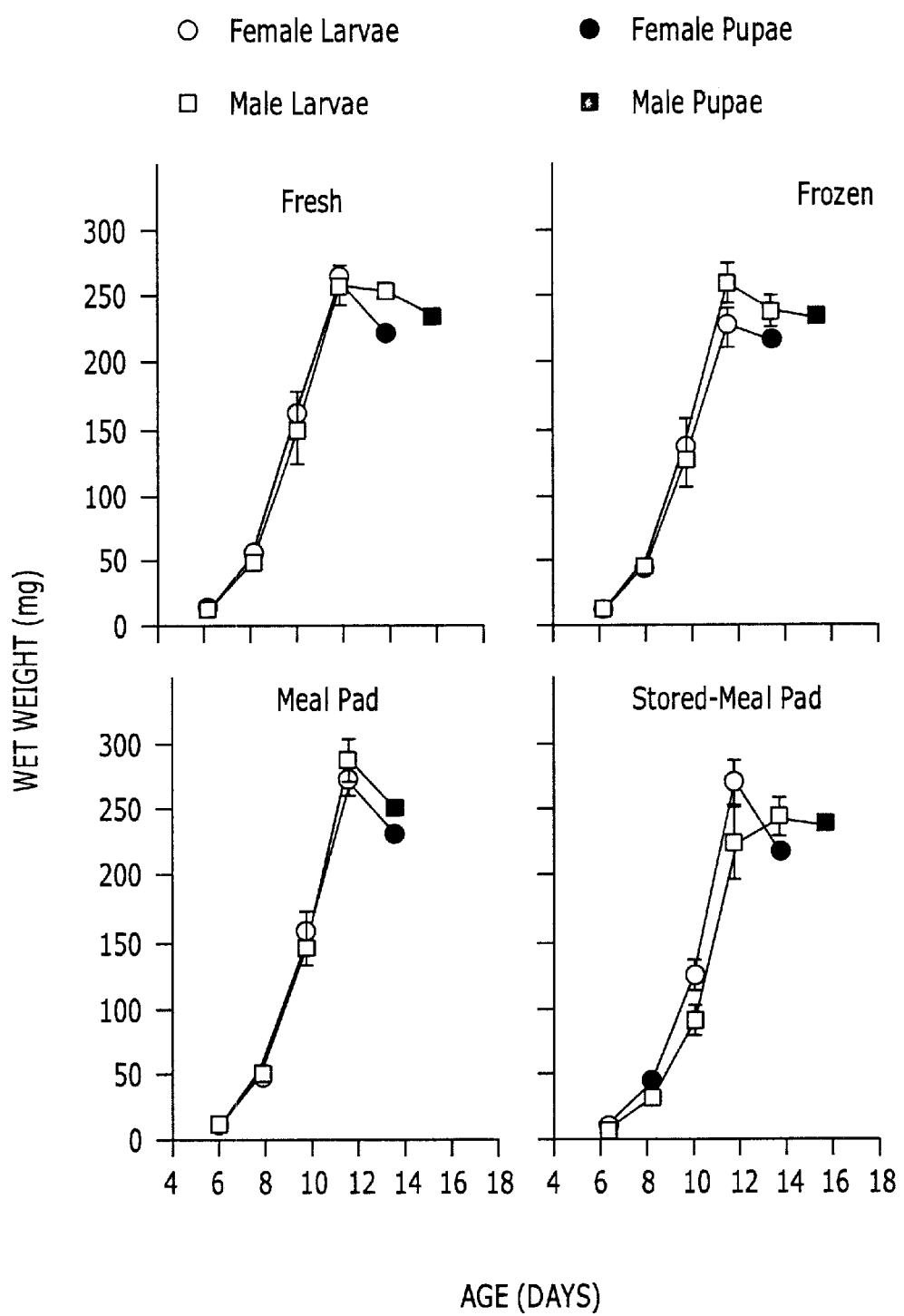

FIG. 19 graphs the mean developmental weight of *T. ni* reared on a pinto bean-based artificial diet. Neonates were placed on artificial diet (fresh or frozen/thawed) or lyophilized meal pads (fresh or stored >90 d), on larva per rearing cup. Wet weights were recorded every 2 d, with the first observation at 6 d after placement on diet. Thirty larvae were placed on each diet variety, and determinations of sex were made after pupation. The last data point in each curve (solid symbols) is the mean pupal weight observed on that day and indicates ≧50% pupation has been reached. Each curve represents a minimum of 12 insects. Error bars represent 1 SE of the mean, which in some cases to do not exceed the size of the symbol.

Figure 20:
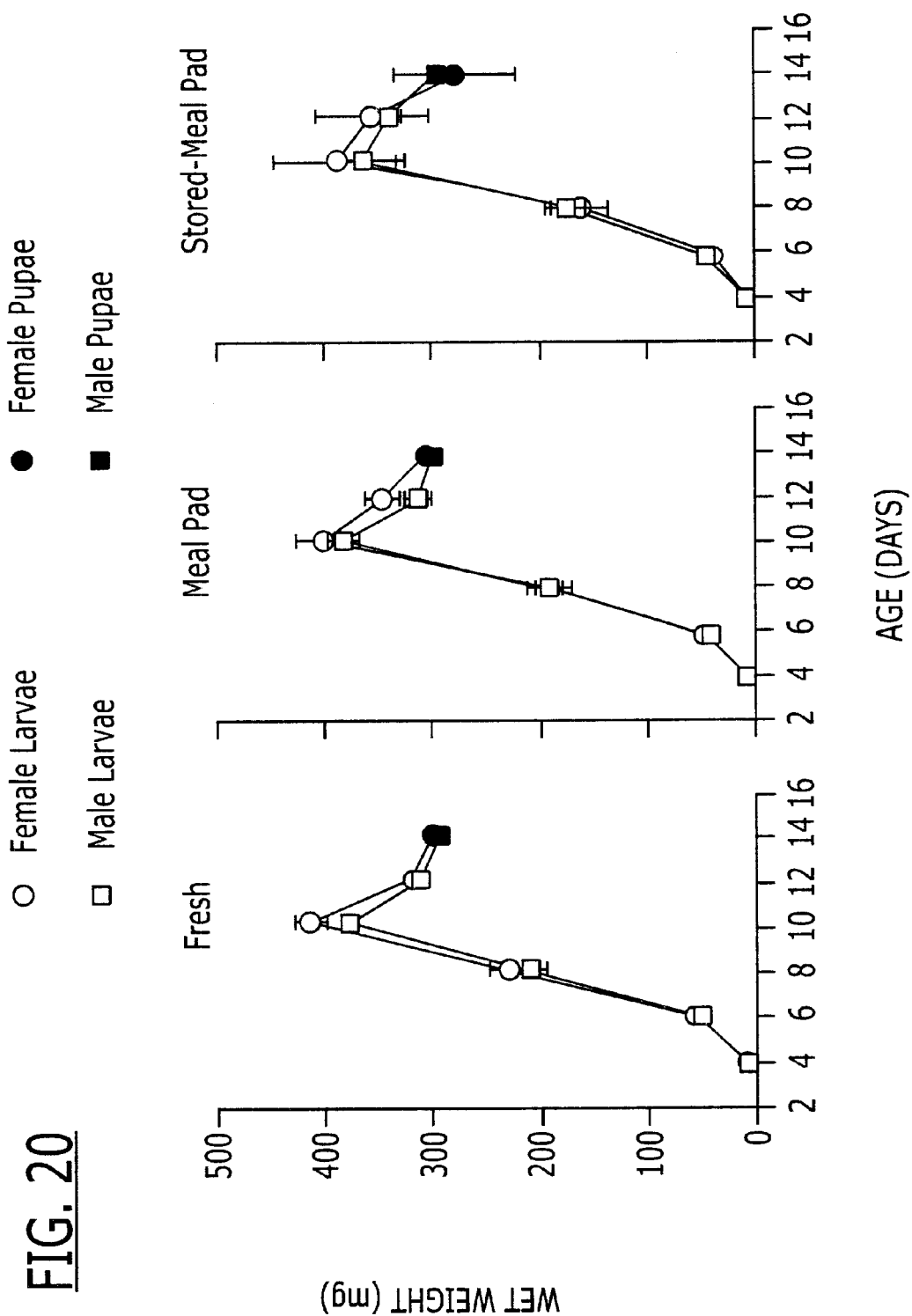

FIG. 20 graphs the mean developmental weights of *H. virescens* reared on a soy protein-based artificial diet. Neonates were placed on artificial diet (fresh or frozen/thawed) or lyophilized meal pads (fresh or stored >90 d), on larva per rearing cup. Wet weights were recorded every 2 d, with the first observation at 6 d after placement on diet. Thirty larvae were placed on each diet variety, and determinations of sex were made after pupation. The last data point in each curve (solid symbols) is the mean pupal weight observed on that day and indicates ≧50% pupation has been reached. Each curve represents a minimum of 9 insects, except for females on stored meal pads (6 survivors). Error bars represent 1 SE of the mean, which in some cases to do not exceed the size of the symbol.

Figure 21:
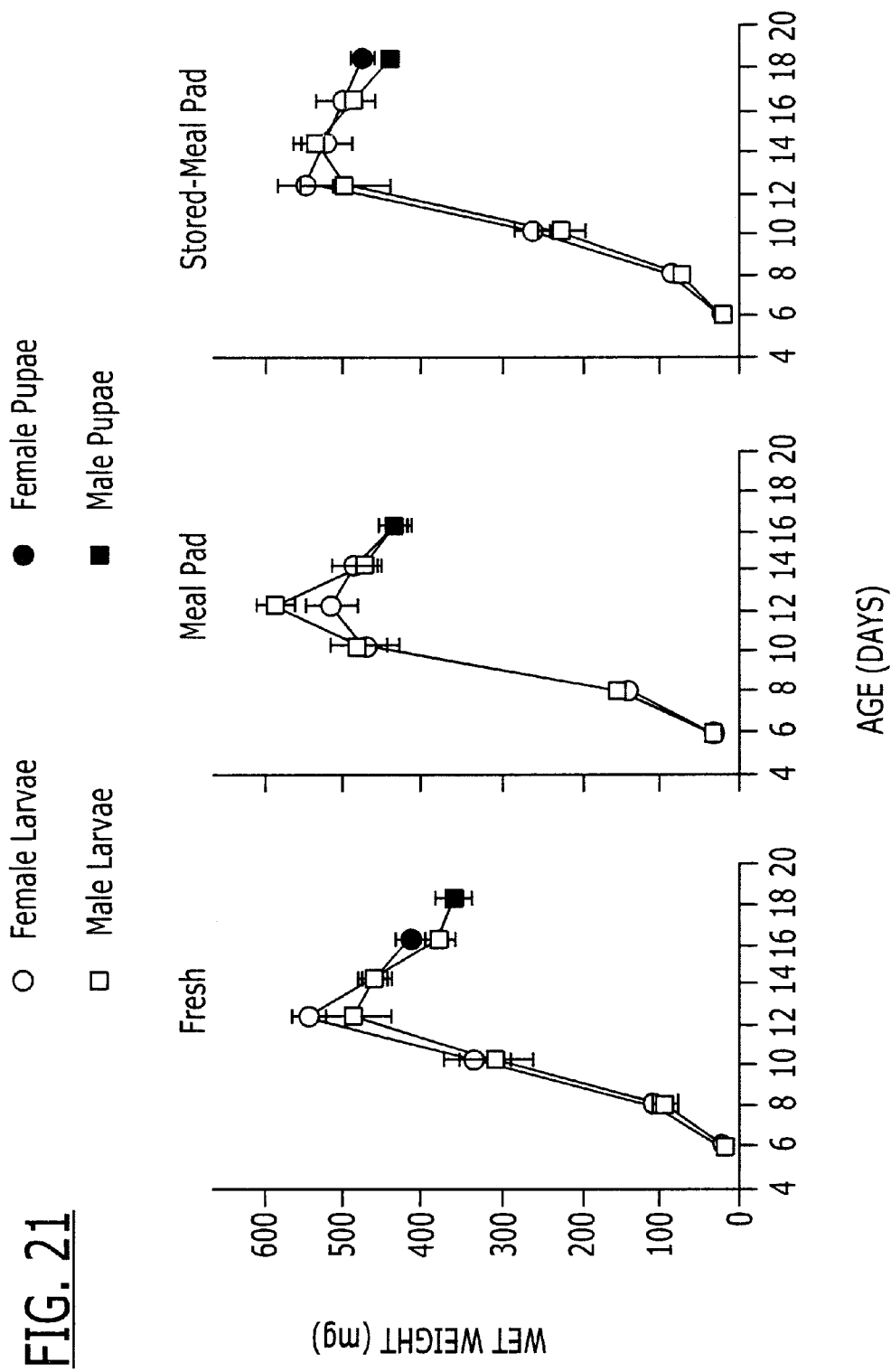

FIG. 21 graphs the mean developmental weights of *H. zea* reared on a soy protein-based artificial diet. Neonates were placed on artificial diet (fresh or frozen/thawed) or lyophilized meal pads (fresh or stored >90 d), on larva per rearing cup. Wet weights were recorded every 2 d, with the first observation at 6 d after placement on diet. Thirty larvae were placed on each diet variety, and determinations of sex were made after pupation. The last data point in each curve (solid symbols) is the mean pupal weight observed on that day and indicates ≧50% pupation has been reached. Each curve represents a minimum of 11 insects. Error bars represent 1 SE of the mean, which in some cases to do not exceed the size of the symbol.

Figure 22:
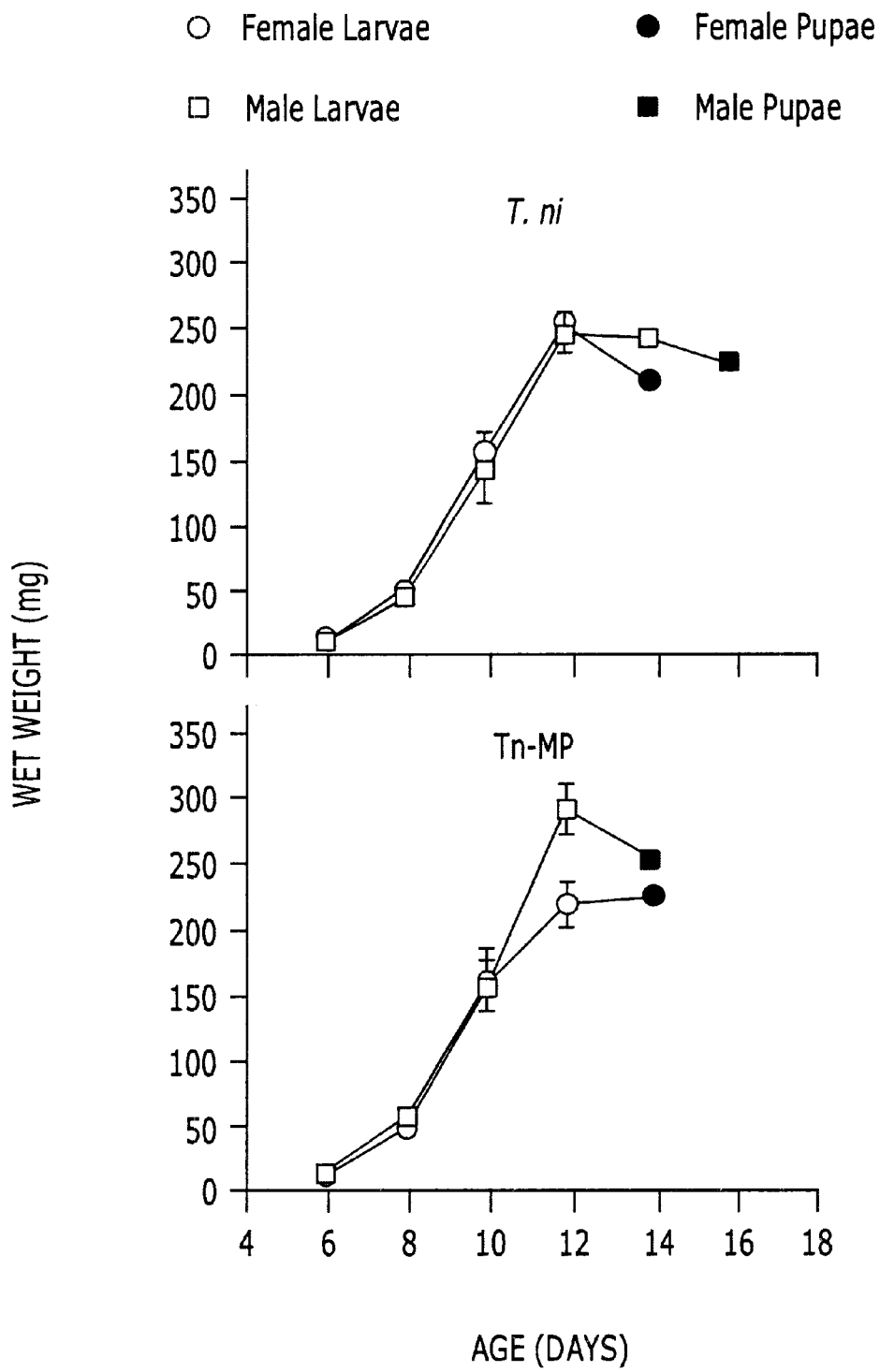

FIG. 22 graphs the mean developmental weight of *T. ni* reared on a pinto bean-based fresh artificial diet. Tn-MP (bottom) were reared on meal pads for seven generations prior to these observations, while a *T. ni* cohort was reared on fresh diet (top). Thirty neonates from each strain were placed on fresh diet, one larva per rearing cup, and wet weights recorded every 2 d, with the first observation at 6 d after placement on diet. Determinations of sex were made after pupation. The last data point in each curve (solid symbols) in the mean pupal weight observed on that day and indicates ≧50% pupation has been reached. Each curve represents a minimum of 12 insects. Error bars represent 1 SE of the mean, which in some cases to do not exceed the size of the symbol.

Figure 23:
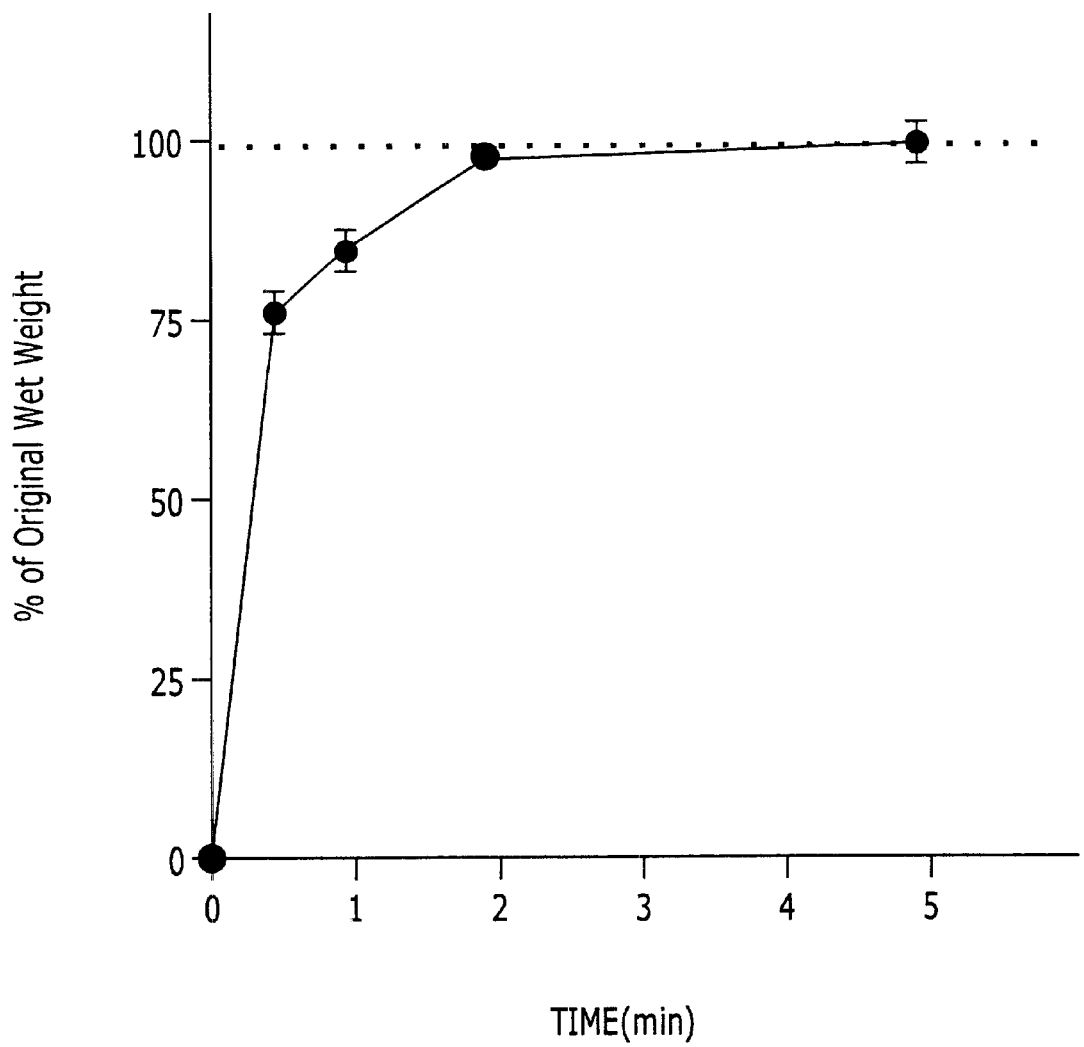

FIG. 23 is a graphical representation of the water content versus time during hydration of 400 μl lyophilized heliothine diet cylinders. Cylinders were placed vertically in excess water (depth=2 mm) and wet weights determined over time. The dotted line represents the original wet weight of the diet cylinders prior to lyophilization. Each point is the mean of three replicates, and bars represent 1 SE of the mean, in some cases not exceeding the size of the symbol.

Figure 24:
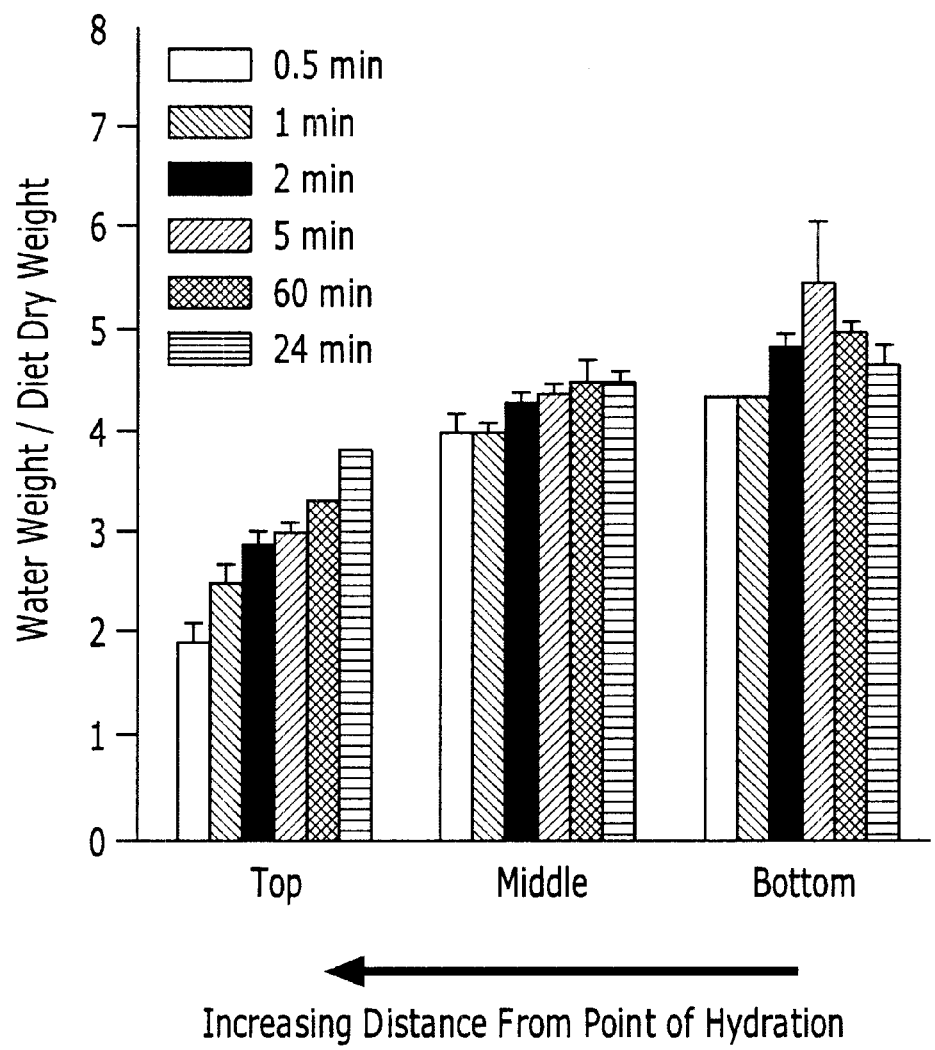

FIG. 24 is a graphical representation of the water content versus time during hydration of 400 μl lyophilized heliothine diet cylinders. Cylinders were placed vertically in excess water (depth=2 mm). Wet weights were determined for the bottom, middle and top thirds of the cylinders at different times after the initiation of hydration. Each column represents the mean of three replicates, and bars represent 1 SE of the mean. Columns without bars are due to SE=0.

Figure 25:
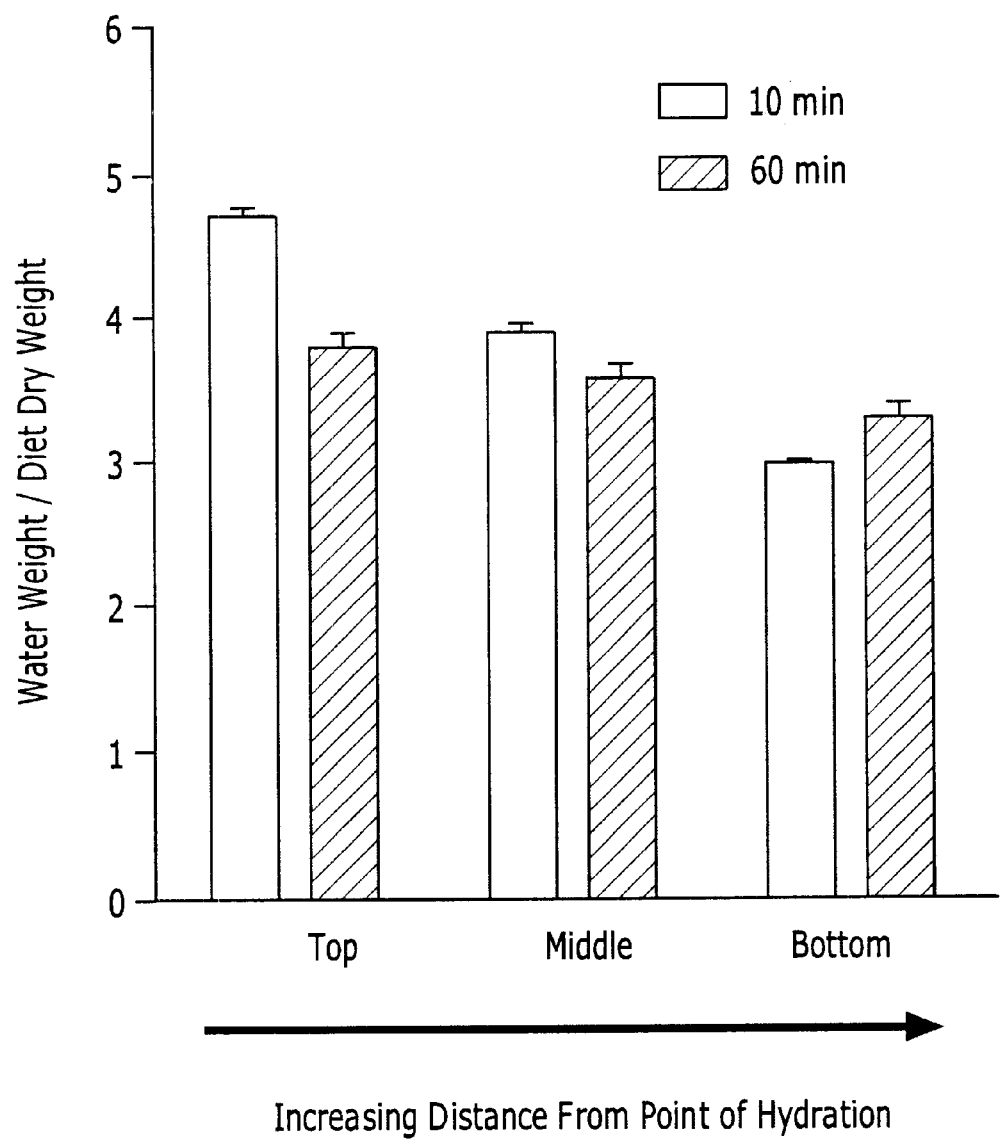

FIG. 25 graphs the ratio of water to dry diet weight with hydration of 400 μl lyophilized heliothine diet cylinders. Vertical cylinders were hydrated from the top to original wet weight. Wet weights were determined for the bottom, middle and top thirds of the cylinders at 10 and 60 min after the initiation of hydration. Each column represents the mean of three replicates, and bars represent 1 SE of the mean.

Figure 26:
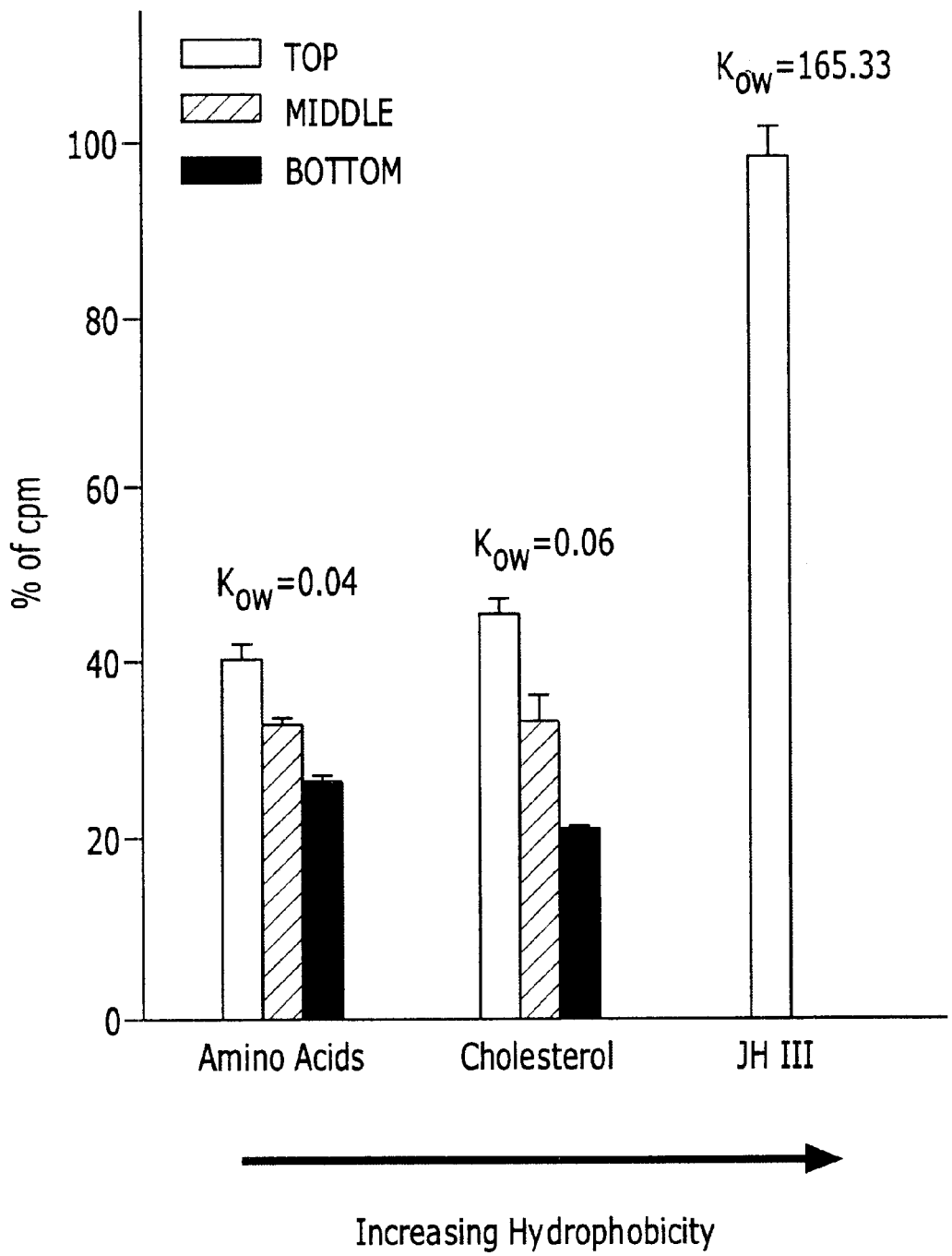

FIG. 26 is a graphical representation of the dispersal of various solutes in 400 μl lyophilized heliothine diet cylinders during hydration. Vertical cylinders were hydrated from the top to original wet weight with water containing one of three radiolabeled compounds in solution, and were divided into three sections (top, middle and bottom) at 60 min. Radioactivity in each cylinder section was then counted, and greater than 90% of the radioactivity was recovered in all experiments. Octanol-water coefficients ($K_{ow}$) are shown for each compound. Each column represents the mean of three replicates, and bars represent 1 SE of the mean. The column without a bar is due to SE=0.

Figure 27:
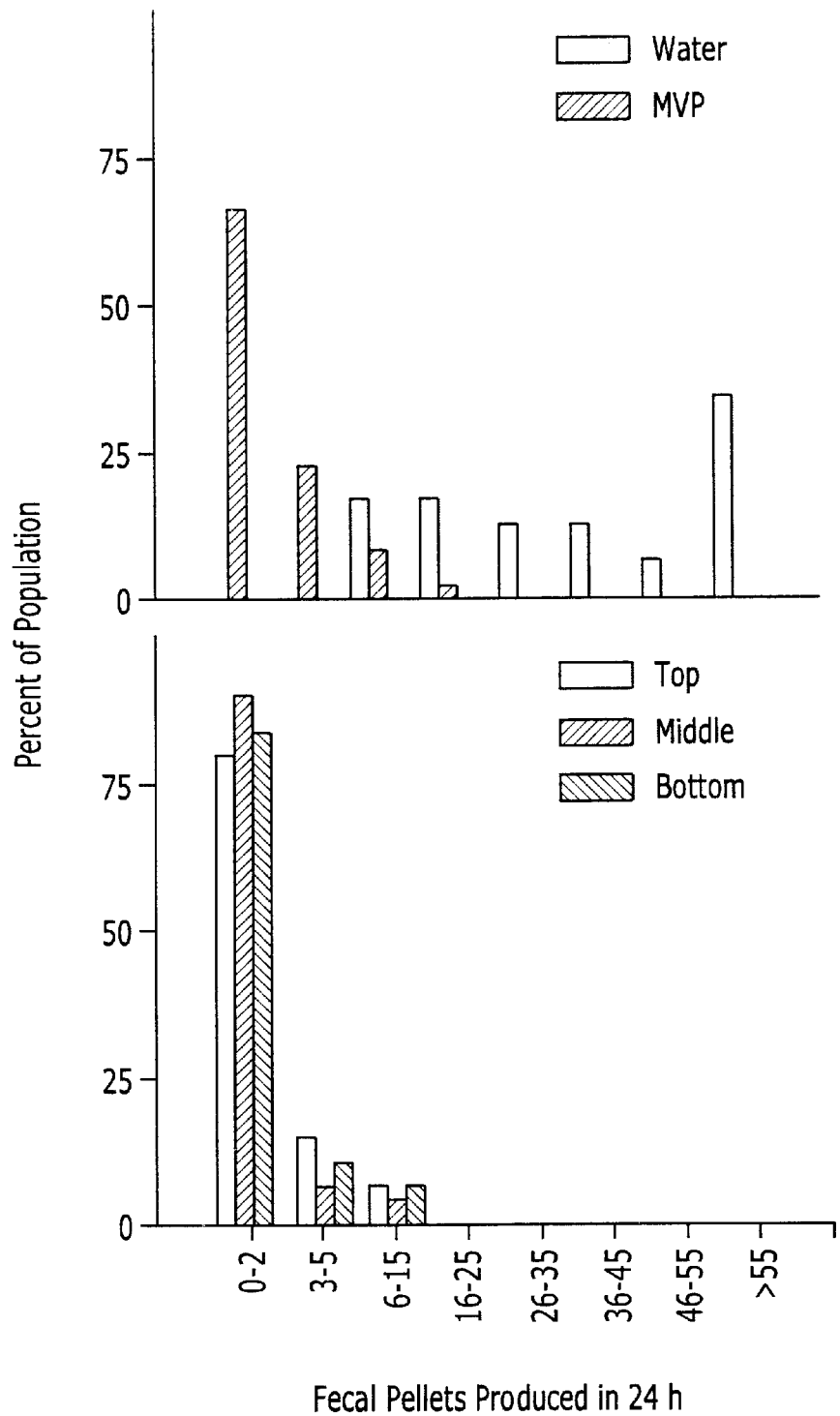

FIG. 27 presents graphical data on use of the feeding disruption bioassay to assess CryIAc diffusion during hydration of meal pads. A dilution of MVP in water was used to hydrate either 400 μl lyophilized diet cylinders or 100 μl meal pads to original wet weight 9 final concentration=0.04 μg MVP per ml diet). *Heliothis virescens* neonates (Hv Washington) were monitored for fecal production at 24 h on (A) 100 μl meal pads hydrated with water or MVP; or (B) 400 μl cylinders hydrated with MVP and divided into equal sections (top, middle and bottom) at 60 min after hydration, one larva per cylinder section. Results were taken from two replicates consisting of 24 insects per replicate.

Figure 28:
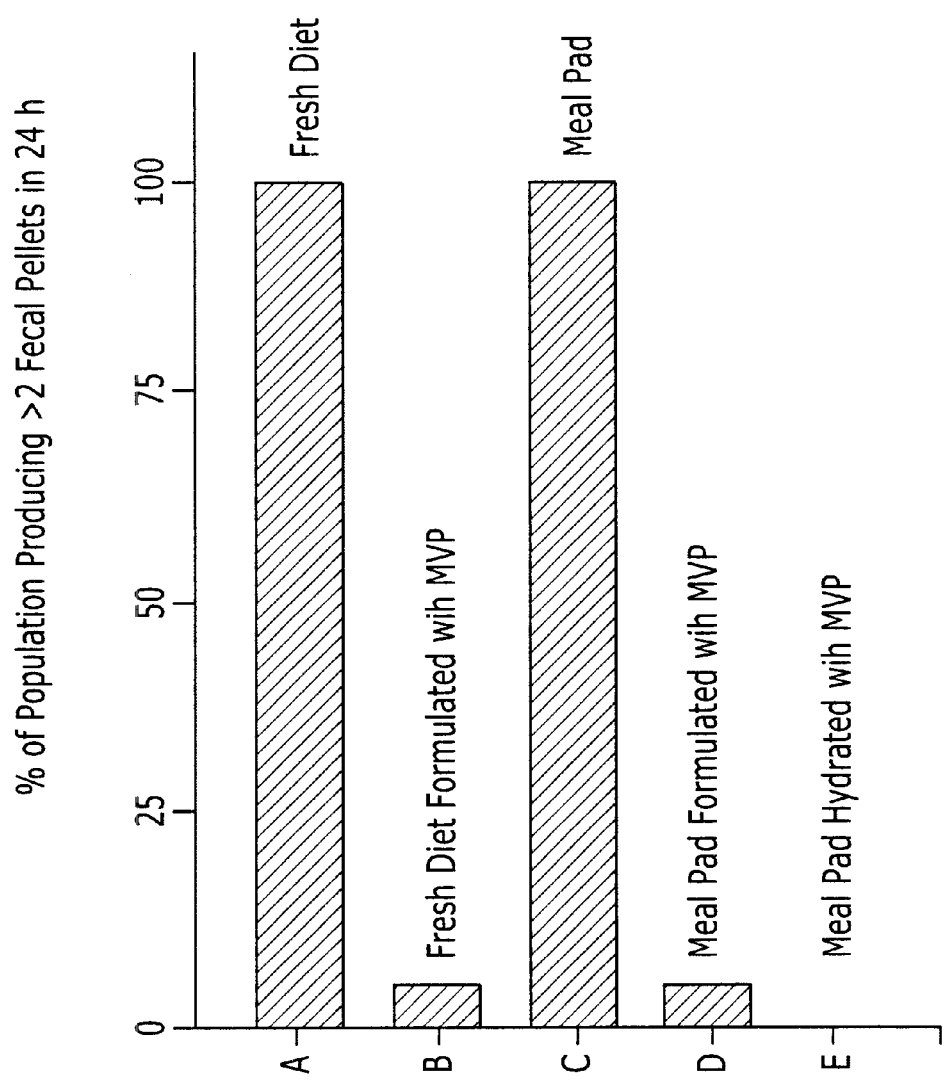

FIG. 28 is a graphical representation of a comparison of various diets in the feeding disruption bioassay. The percent of a population of *Heliothis virescens* neonates producing >2 fecal pellets in 24 h was compared on the following diets: (A) fresh, (B) fresh with 0.04 μg MVP per ml diet incorporated during diet formulation, (C) meal pads hydrated with water only, (D) meal pads containing 0.04 μg MVP per ml diet incorporated during diet formulation prior to lyophilization, and (E) meal pads with MVP incorporated during hydration (final concentration=0.04 μg MVP per ml diet). Results were taken from two replicates consisting of 24 insects per replicate.

Figure 29:
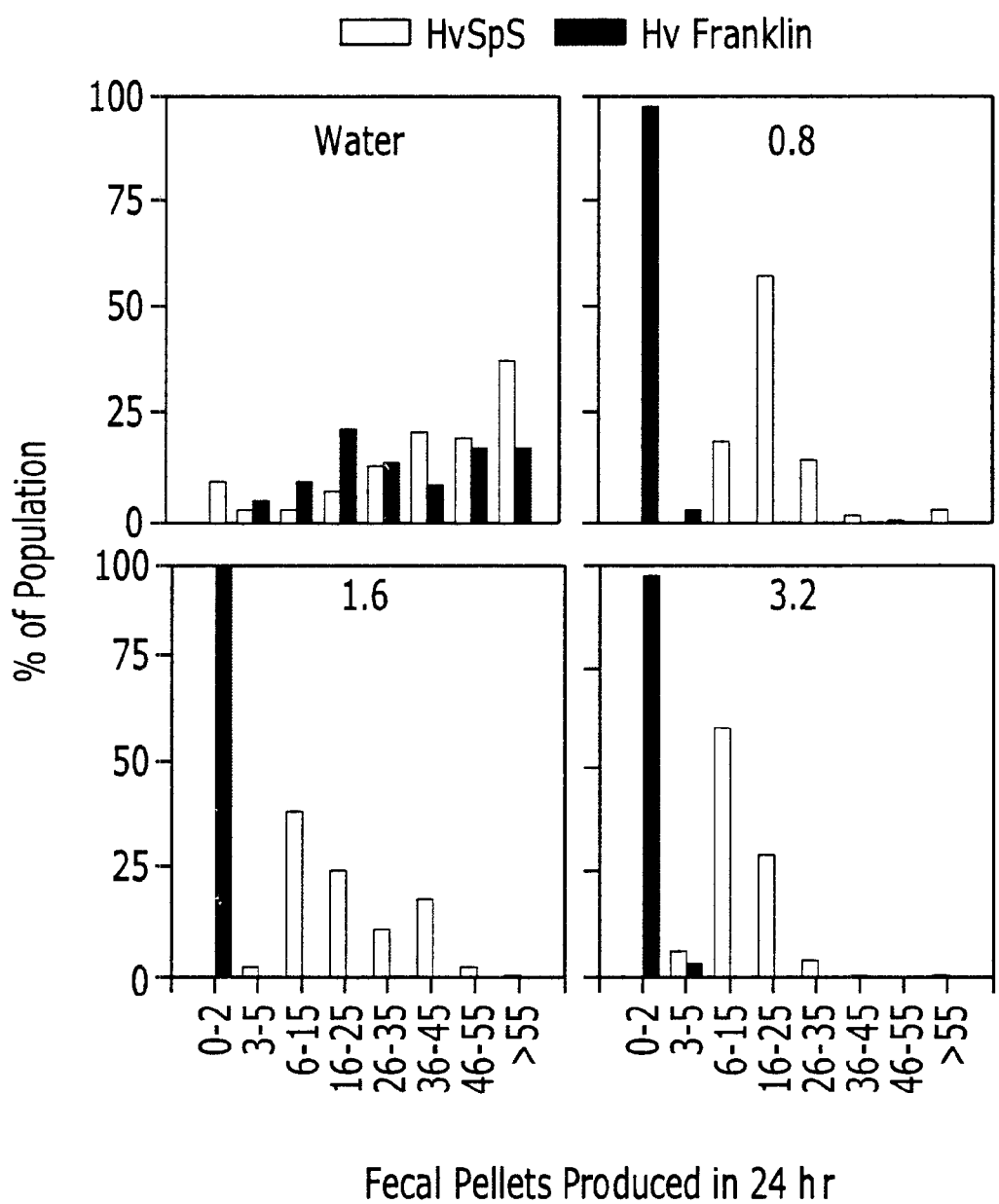

FIG. 29 is a graphical representation of the results from the feeding disruption assay as used to detect resistance in neonates of the tobacco budworm. Hv Franklin and Hv spinosad selected (HvSpS) neonates were placed on artificial diet containing 1.6 μg of spinosad (active ingredient) per ml diet and blue feces production measured after 24 hours. Spinosad was added to the diet as a formulated material (Tracer(t). Results were taken from two replicates consisting of 24 insects per replicate.

DETAILED DESCRIPTION OF THE INVENTION

The most common endpoint for assessing Bt susceptibility in lepidopteran larvae has been mortality at 7 to 10 days after treatment. Van Frankenhyzen et al., *Appl. Environ. Microbiol.* 57:1650–1655 (1991) used a 50% reduction in frass production in three days as a measure of toxicity for different Bt toxins against several species of forest pests.

Immunochemical and DNA amplification methods of species identification for *H. zea* and *H. virescens* are known. Cibulsky and Ng, In: *Proceedings Beltwide Cotton Conference*, pp. 889–891, National Cotton Council, Memphis, Tenn. (1996); Roehrdanz, R. USDA ARS Report Number 075350; U.S. Pat. No. 5,656,437 (Greenstone). Such methods may not be convenient for field use.

An additional method to distinguish *H. virescens* and *H. zea* eggs is described in Cibulsky and Ng, In: *Proceedings Beltwide Cotton Conference*, pp 889–891, National Cotton Council, Memphis, Tenn. (1996).

The present pesticide resistance assays and species identification assays are based on feeding disruption caused by pesticides such as the biopesticide *Bacillus thuringiensis* toxin (Bt). The assay end-point is feeding disruption, which is measured by the fecal production of insects exposed to a diagnostic dose of pesticide in a test diet. The test diet preferably also contains a marker compound as an aid in assessing fecal production from the test diet. Resistance can be assessed at the level of an individual insect or at population levels. Where insect larvae are utilized, those that survive the present assay methods can be reared to mature larvae or adults for visual species identification, or used at any stage in development in immunodiagnostic or DNA identification assays if desired.

The present inventors found that both Bt resistant and Bt susceptible third instars of the tobacco budworm (*H. virescens*) produced feces when fed a diet containing Bt, but that the rate of defecation was greatly reduced in susceptible insects. Feces produced by budworms on such diets could be derived from several possible sources, i.e., the Bt-containing test diet; from residual food in the larval digestive system from feeding prior to initiation of the bioassay; or from feeding on extraneous materials such as the cardboard lid of the assay container or egg chorion. To provide a marker for feeding on diet containing Bt toxin, Trypan Blue was incorporated into a standard artificial diet at the rate of 20 mg/ml of diet. Trypan Blue was selected because the blue feces produced by budworms on this diet can be easily distinguished from the brown feces derived from normal artificial diet, from the dark green feces produced by budworms feeding on cotton plants, and from the lightly colored feces produced by neonates feeding on the egg chorion. Insects reared on the Trypan Blue diet produced a distinctive smooth and shiny blue fecal pellet, different in appearance from feces produced by insects feeding on other possible sources.

Using a test diet containing a predetermined amount of Bt and Trypan Blue as a marker for ingestion of the test diet, the present inventors devised an assay to distinguish Bt resistant and Bt susceptible strains of *H. virescens*. The number of fecal pellets containing the marker, produced over a predetermined time period after exposure to a test diet containing a predetermined amount of Bt toxin, is indicative of Bt susceptibility or Bt resistance. The present methods are useful in detecting *H. virescens* larvae with economically significant levels of Bt resistance. The present methods are additionally useful in distinguishing between *Heliothis virescens* (Bt susceptible) and *Helicoverpa zea* (relatively Bt resistant) species.

It will be appreciated by those skilled in the art that *H. zea* are naturally more tolerant or "resistant" as a species to Bt than is *H. virescens*. Accordingly, the present invention may be used to distinguish between these two species. It will further be understood, however, that in other embodiments of the invention (described hereinbelow), the present invention may be practiced to detect the presence of *H. zea* that have developed field resistance to Bt, or other insecticides, beyond the tolerance naturally found in this species.

The present invention provides a method of detecting *H. zea* larvae within a group of larvae that appear to be *H. virescens*. Each larva is given access to a test diet containing a predetermined diagnostic amount of *B. thuringiensis* toxin. The diagnostic amount is previously determined using dose/response studies as outlined in the Examples provided below and knowledge in the art, to determine a dose of toxin and a time period during which *H. zea* larva (resistant to the Bt toxin) produce an amount of feces that is significantly greater than that produced by *H. virescens* (susceptible to Bt toxin) larva. After a larva is given access to the test diet for the predetermined test time, the amount of feces produced during that time is assessed, for example by counting the number of fecal pellets produced. Larvae that produce more than the predetermined diagnostic amount of feces are considered to be *H. zea*. In an exemplary assay, the test diet contains CryIAc *Bacillus thuringiensis* toxin at a concentration of from about 0.030 µg, or from about 0.032 µg, to about 0.035 µg CryIAc/ml diet, and the test time is 24 hours. Larvae producing seven or more fecal pellets are indicated as *H. zea*.

The present invention further provides a method of detecting, in a single test larva or in a plurality of test larvae, resistance to a pesticide known to cause feeding disruption in susceptible insects. Each larva is given access to a test diet (containing a predetermined resistance-diagnostic amount of the insecticide) for a predetermined time. The amount of feces produced by each larva over the test time is then quantified. Any larva producing more than the predetermined diagnostic amount of feces is considered resistant to the pesticide. The resistance-diagnostic amount of insecticide and the test time are previously determined using dose/response assays as described herein, and techniques known in the art. Alternatively, the presence or absence of feces may be assessed to determine resistance. It will be apparent to those skilled in the art that "resistance" is a relative term; an insect that is resistant to a low level of an insecticide may be susceptible to a larger dose.

The present invention further allows one to design an assay to discriminate between an insect type that is resistant to a pesticide and an insect type that is susceptible to a pesticide, where the pesticide is one that causes feeding disruption. As used herein, an 'insect type' may be a species, a subspecies, a particular strain of a species, or a geographic population of a species or subspecies or strain. Multiple larvae of each of the insect types are obtained, and a dose/response study is conducted, using methods described in the Examples below and knowledge in the art. The dose/response study determines a diagnostic dose of the pesticide, and a diagnostic feeding period, whereby the amount of feces produced by the two insect types differ significantly.

The present invention further allows one to design an assay to screen a homogenous population of insects for the development of pesticide resistance, where the pesticide causes feeding disruption. The screening may occur over time or over a geographic area. A homogenous population, as used herein, may refer to a particular species, subspecies or strain of insect, or a geographic population of a particular species, subspecies or strain. Larvae are obtained from the population of insects being tested, and a dose/response study is conducted to determine a resistance-diagnostic dose of said pesticide, and a diagnostic feeding period, during which the amount of feces produced by the larvae decreases significantly, compared to larvae fed on a control diet. Testing of additional subjects over time or over a geographic area can be used to detect the development of increased resistance to the pesticide.

As a further aspect, the present invention may also be employed to screen compounds for insecticidal activity, in particular, in the feeding disruption assays described herein. According to this activity, insecticidal activity may be assessed against one or more species of insects. As described in more detail hereinbelow, screening assays are preferably carried out with the hydratable meal pads and/or apparatus of the invention. According to this embodiment, the screening of large numbers of compounds by bioassay may be accomplished more rapidly and conveniently than with conventional methods. The present inventive methods provide an endpoint (e.g., colored or fluorescent feces on a contrasting background) that may be detected by digital imaging systems in high throughput formats.

Any compound of interest may be screened for insecticidal activity using the inventive feeding disruption assays described herein, including both polar and non-polar compounds. In particular embodiments, the invention may advantageously be employed in a high through-put screening format, for example, to screen large numbers of compounds including the screening of combinatorial libraries of compounds. The production of colored feces permits detection with digital imaging systems, which enables a high through-put automated screening assay for new insecticides (alternatively, for the detection of resistance or for distinguishing among species, as described herein). In other embodiments, a digital imaging system may monitor feces production by detecting particles of greater than a set size (i.e., to distinguish feces from the insect).

In particular embodiments, it is not necessary to quantify the amount of feces produced (e.g., by weight, volume or number of fecal pellets). According to this embodiment, it is only necessary to assess the presence or absence of any fecal pellets containing the marker. Such qualitative assessments may be used for rapid determination of resistance to the dose of Bt, or another pesticide, provided to the insect(s). Alternatively, a qualitative assessment may be used in conjunction with any of the feeding disruption assays described herein.

In each of the above methods, the test diet may additionally contain a marker compound that imparts a detectable characteristic (e.g., color, fluorescence, luminescence) to feces produced by the test subject. A preferred marker is the dye Trypan Blue. Additionally, it is preferred that the larva test subjects be starved for a period of time prior to being placed on the test diet, for example, for about an hour.

As used herein, a plurality of insect larvae may refer to a sample of insect larvae taken from a field, or to insect larvae produced by insects obtained from a field. As used herein, giving larvae access to a test diet means that larvae are placed in contact with or in close proximity to the test diet, and the larva are allowed to feed at liberty.

The present invention further provides a kit for testing insect larvae for resistance to a pesticide, where the pesticide causes feeding disruption. The kit contains at least one container of a size sufficient to contain at least one of the test insect larvae during the test period, and contains a test diet with a resistance-diagnostic amount of the pesticide. Printed instructions set forth the diagnostic time period, and the amount of feces that indicates that the test larva is resistant to the pesticide.

The present methods can be used with any insecticide that causes feeding disruption by any means (behavioral or physiological) in susceptible insects, including chemical insecticides and biopesticides such as Bt toxin. Chemical insecticides include pyrethroids (cypermethrin, bifenthrin, cyfluthrin, esfenvalerate, permethrin, tralomethrin, cyhalothrin, zetacypermethrin), carbamates, diamidides, organophosphates, organochlorines, spinosyns (e.g., spinosyn A and/or spinosyn D), and chloronicotinoids.

Pyrethroid-resistant populations of tobacco budworms (*H. virescens*) have been documented in the Southeastern United States. Resistance is typically measured using mortality assays, such as a 'vial test' in which glass vials are coated on the inside with a predetermined dose of insecticide that kills a majority of susceptible moths but not resistant moths. Strains of tobacco budworm resistant to carbamate and organophosphate insecticides are also known. Additionally, strains of cotton bollworm (*Helicoverpa armigera*) resistant to pyrethroid insecticides are known in Australia, and may exhibit cross-resistance to several pyrethroids.

The present methods are suitable for use with any insect that is susceptible to, or that is exposed to, an insecticide that causes feeding disruption and reduced fecal output. Such insects include, but are not limited to, the tobacco budworm (*Heliothis virescens*), bollworm or cotton earworm (*Helicoverpa zea*), and diamondback moth (*Plutella xylostella*). Susceptible insects may be monitored for the development of resistance or to assess levels of resistance; the feeding disruption assay may be carried out using larvae or adult insects, as would be apparent to one skilled in the art. As used herein, the term "insect" refers to both larval and adult forms of insects. As used herein, an "insect type" refers to a distinct group of insects that can be characterized by morphological, geographical, or phenotypic characteristics. An insect type may be a species or sub-species, or a geographical variant or isolate of a species.

As used herein, a test diet refers to a diet suitable for the insect(s) being tested, as is known in the art. In the present assays, a predetermined amount of pesticide is provided in the test diet; the amount of pesticide is sufficient to cause a statistically significant difference in fecal output between resistant and susceptible insects (species or strains) over a predetermined time period. The amount of pesticide will vary depending on the pesticide, the insect species, and the time over which feeding is allowed to occur. The amounts of pesticide and the time course of a particular assay may be determined by one skilled in the art using the procedures as taught herein. The same diet, but lacking any pesticide, may be used as a control.

The present test diets preferably also contain a marker substance. As used herein, a marker substance is one that, when ingested by an insect, imparts a detectable characteristic to feces produced by the insect. The detectable characteristic may be color, overall appearance, or a chemically detectable reaction. Preferred markers are dyes that impart a distinct color to fecal pellets; a particularly preferred marker is the dye Trypan Blue. Also useful are pH sensitive dyes, fluorescent dyes, luminescent dyes, and cytosolic markers of any type.

The present feeding disruption assays are simple and suitable for use by farmers and extension agents. The assay can be conducted on individual insects collected from the field as eggs, larva, neonates or older larvae, and results can be obtained within a short time, such as within 24 hours. Because the feeding disruption test does not result in the death of the insect, insects can subsequently be used for additional diagnostic assays, such as assaying for resistance to chemical insecticides, and/or can be raised to adulthood for visual species identification.

It will be apparent to those skilled in the art that an insect that is resistant to an insecticide at a particular dose may be susceptible to the same insecticide at a higher dose. As used herein, "resistance" and "susceptibility" are not absolute, but refer to survival after exposure to a particular dose of insecticide. Species and strains commonly referred to as "resistant" are those that survive exposure to recommended commercial doses of insecticide. The present assays are useful in detecting the presence of insects in the field that are resistant to recommended doses of commercial insecticides, and are further useful in detecting the level of resistance present in a population or strain of insect, or in comparing the relative resistance of two species or strains. Resistance, as used herein, does not imply that an insect is impervious to all effects of an insecticide, or that a higher dose of the insecticide would not harm the insect.

Accordingly, the present invention provides methods to assess resistance (e.g., determining the response to varying dosages of insecticide in a homogenous population of insects). The present invention further provides methods for typing species or strains of insects based on previously determined resistance profiles (e.g., typing larvae collected from the field to distinguish between *H. zea* and *H. virescens*, based on differing susceptibility to Bt toxin).

The present feeding disruption assay can be tailored for use where species that are difficult to distinguish in the larval stage differ in their susceptibility to a particular pesticide, and where the geographic ranges of the species overlap. The pesticide to be tested is one that disrupts feeding behavior. Sample insects are placed on a test diet containing a predetermined amount of the pesticide and preferably also containing a marker substance. The amount of pesticide in the test diet is sufficient to cause a statistically significant difference in fecal output between resistant and susceptible species over a predetermined time period. The amount of pesticide will vary depending on the pesticide, the insect species, and the time over which feeding is allowed to occur.

Where resistant *H. virescens* are absent from natural populations, the present feeding disruption assay is useful to discriminate between *H. virescens* and *H. zea* larvae, i.e., it is a species discrimination test.

A species-discriminating dose (or 'diagnostic dose') of Bt (determined using the methods described below) is provided in the assay diet, and a test sample of larvae is exposed to the diet for a predetermined time. The rate of feces production is examined over time or at a predetermined time point. The presence of larvae producing a diagnostic amount of feces indicates the presence of *H. zea*. In fields planted with Bt-expressing transgenic crops, the presence of *H. zea* (known to be naturally resistant to Bt) indicates that further pest control measures are necessary.

The production (or lack of production) of blue feces over time at the appropriate diagnostic concentration of Bt is the criterion used to discriminate resistant and non-resistant species.

Where strains of an insect species are known to be resistant to an insecticide, but other strains are susceptible to that insecticide, the present feeding disruption assays are useful in detecting the presence of resistant strains.

A resistance-discriminating dose (or 'discriminating dose') of Bt (determined using the methods described below) is provided in the assay diet, and a test sample of insect is exposed to the diet for a predetermined time. The rate of feces production is examined over time or at a predetermined time point. The presence of insects producing a diagnostic amount of feces indicates the presence of resistant strains. In fields planted with Bt-expressing transgenic crops, the presence of strains resistant to Bt toxin indicates that further pest control measures are necessary.

The production or lack of production of blue feces over time at the appropriate diagnostic concentration of Bt is the criterion used to discriminate resistant and non-resistant species.

As shown in the examples below, Bt resistant YHD2 budworm (*H. virescens*) larvae on test diet containing the appropriate diagnostic dose of Bt and the marker Trypan Blue produce blue feces; susceptible Wake or Wake×YHD2 hybrid *H. virescens* larvae under the same assay conditions produce minimal blue feces. The difference in feces production is sufficient to allow identification of resistant strains.

The present feeding disruption assays are useful in monitoring the development of resistance to a pesticide in natural insect populations.

A resistance-discriminating dose ('discriminating dose') of pesticide (determined using the methods described below) is provided in the assay diet, and a test sample of insects is exposed to the diet for a predetermined time. The production of feces over time is monitored, where a certain level of feces production is indicative of resistance to the insecticide being tested.

The present feeding disruption assays provide a more rapid assessment of resistance than the standard mortality assay. The discriminating dose of insecticide in the test diet determines the minimum detectable level of resistance, and the sensitivity of resistance detection is limited only by population variability in toxicity for susceptible and resistant genotypes. The discriminating dose may be set based on field data of species susceptibility in specific geographical areas, and/or what would be considered economically significant reductions in susceptibility due to selection.

The above resistance monitoring assays are useful in monitoring natural populations of moths for the development of resistance to Bt toxin. Female moths may be collected or trapped in the field and visually identified as to species. Larvae produced by the moths can then be assayed for resistance.

The present feeding disruption assays are useful in assessing different strains within a species for resistance to a pesticide.

A resistance-discriminating dose ('discriminating dose') of pesticide (determined using the methods described below) is provided in the assay diet, and a test sample of insects (of known strains) are exposed to the diet for a predetermined time. The production of feces over time is monitored, where a certain level of feces production is indicative of resistance to the insecticide being tested, and differences among strains in feces production is indicative of differing levels of resistance. The discriminating dose of insecticide in the test diet determines the minimum detectable level of resistance. The discriminating dose may be set based on field data of species susceptibility in specific geographical areas, and/or what would be considered economically significant reductions in susceptibility due to selection.

The above resistance identification assays are useful in identifying insect strains with resistance to an insecticide such as Bt toxin. Strains having known resistance to insecticides are useful in testing new insecticidal formulations.

Insect Meals and Hydratable Meal Pads.

Agar-based insect meals are commonly used in rearing insects. However, agar-based meal-gels require refrigeration, and condensation of water in the cup or syneresis of the gel can create a film of water that immobilizes and/or kills newly emerging larvae. A dry insect diet, hydratable at the time of use with water or with an aqueous solution of insecticide, would be useful in the present feeding disruption assays. The present inventors have unexpectedly found that insect meal pads may be formulated that upon dehydration and subsequent rehydration retain their functional properties such that they are substantially similar to fresh insect meal.

Such hydratable meal pads are also useful, when formulated without insecticide, in the routine rearing of insects. Meal pads can also be used for high throughput in vivo screening of chemicals for insecticidal activity where the meal is reconstituted at the point of use, typically, with an aqueous chemical solution. The meal pad may also be stable to applications of organic solvents containing insecticides or chemicals to be screened for insecticidal activity. The meal pads are also convenient for assessing insect resistance under field conditions where fresh meals would not be practical, for example, because of their perishable nature.

A dehydrated insect meal pad may be described as an insect meal in the form of an integral unit of a solid gel-sponge or solid porous matrix that rehydrates upon the addition of water or other aqueous solution. Preferably, upon rehydration, the meal pad retains substantially the same size, shape and gel properties as the fresh meal pad prior to dehydration. It is also preferred that the rehydrated meal pad retains substantially the same nutritional properties and other characteristics that support insect growth and development. In other preferred embodiments, the meal pad permits the incorporation (preferably, homogenous incorporation) of materials (e.g., insecticides or compounds to be tested for insecticidal activities) into the porous matrix during the re-hydration step.

Thus, in the most preferred embodiments, the dehydrated meal pads of the present invention may be used for substantially all of the purposes for which fresh insect meal pads may be employed. Alternatively stated, the meal pads of the present invention, upon rehydration, maintain substantially all of the functional characteristics of the fresh insect meal pad (e.g., nutritional content, shape, gel properties). The rehydrated meal pad preferably retains a gel-like state and retains its shape after application of light to moderate pressure to the surface thereof.

A preferred insect meal pad comprises a dry or dehydrated insect meal present or supported in a matrix or substrate. The matrix or substrate is preferably a porous or water permeable polymer gel matrix. Such matrices or substrates containing an insect meal are referred to herein as "meal pads", "dehydrated meal pads" or "hydratable meal pads". The meal pads can be stored dry and hydrated with water or with an aqueous solution at the time of use. Generally, the meal pad is a discrete unit, such as a disk, chip, wedge, wafer, or the like.

Any suitable matrix material may be used that produces a meal pad with the characteristics described herein. Agars, wheat starches, and corn starches are preferred, with agars being most preferred. Also suitable are gellan gums, gum tragacanths, and agars containing dextrin or other strengtheners. The gel matrix support may be a substance that is itself consumable by the insect, for example, a gellable polysaccharide (see U.S. Pat. Nos. 5,141,744; 4,326,052 and 4,326,053; all U.S. patents cited herein are incorporated herein in their entirety). Preferred meal pad compositions will substantially rehydrate and maintain a gel structure upon the addition of an aqueous liquid (e.g., water), and will further retain substantially the same size, shape and gel properties upon rehydration that they possessed before drying.

In particular embodiments of the invention, the liquid meal pad composition is cast as a film or impregnated within a porous mesh substrate (e.g., an open or porous paper, or a plastic mesh or web).

Beneficial supplements may optionally be added to the meal pads, including fungicides, stabilizers and UV protectants, as are known in the art. Where meal pads are used in the insecticide resistance assays as described herein, a predetermined concentration of insecticide and/or a marker such as Trypan Blue may also be added to the insect meal portion of the meal pad.

It is preferred that the meal pad composition be formulated so that it may be conveniently dispensed. For example, as the concentration of agar is increased beyond 2.5%, the meal pad composition may become too viscous and difficult to dispense. As a further consideration, it is also preferred that the meal pad is formulated so that insects feeding thereon produce a firm and discrete fecal pellet, rather than a liquid frass. For example, the present inventors have observed that at relatively low concentrations of insect diet in the meal pad formulation (e.g., less than about 20% w/v), the frass may be more liquid than is desired. Likewise, corn/soy blend diets are preferable to all-corn or all-soy diets for producing a pellet of the desired firmness and texture. As yet a further consideration, when selecting the concentration of the matrix material to be included in the meal pad, it is desirable that the pore size in the polymer matrix be sufficiently large to facilitate the incorporation of compounds into the matrix, e.g., during or following rehydration.

Concentrations of agar in the meal pad are typically about 0.5% (w/v) to about 4% (w/v), more preferably about 0.5% (w/v) to about 2.5% (w/v), still more preferably about 0.5% (w/v) to about 1.5% (w/v). When wheat and corn starches are used as the matrix material, these substances are generally included in the meal pad composition at about 7.5% (w/v) to about 15% (w/v), more preferably about 10% (w/v) to about 12% (w/v).

The meal pad may be formed by combining the meal, matrix material, and any other desired components (e.g., indicator and/or insecticide) together using any method known in the art and dispensed into individual meal pads. The fresh meal pad composition may optionally be dispensed into pre-formed molds, wells, containers, cups, and the like, to give the meal pad a desired shape. In particular embodiments, an insect meal and matrix material (e.g., agar) are combined and heated. The heated mixture is dispensed into individual molds, wells, containers or cups to form a solid meal pad disk or chip after cooling. Upon heating, the polymer is loosened, and when the mixture is cooled, the polymer bonds reform in the new shape.

Alternatively, the meal pad composition may be formulated in a mixed solvent system (e.g., an alcohol/water or acetone/water mixture). According to this embodiment, the non-polar solvent may be evaporated off after dispensing the fresh meal into the mold, well, cup, etc., and the gel will come out of solution and form as the non-polar solvent is removed by evaporation.

In general, the dehydrated meal pad comprises by weight: about 0.5–12% matrix (which may itself be edible), about 10–90% insect meal or other nutrient composition, less than about 1% free water, 0 to 5% marker, and 0 to 0.1, 1% or 2% (or more) insecticide or compound to be screened for insecticidal activity.

The meal pad may have any size or shape that is suitable for the particular end use. Typically, the meal pad will be a round disk-shape. In preferred embodiments, the pads will be formed to fit into apparatus or devices for rearing insects or feeding disruption assays, as described below. Typically, a meal pad for insect rearing will be prepared from about 5 to about 20 ml of meal. Meal pads for feeding disruption assays will generally be smaller, e.g., from about 20 μl to about 2 or 3 ml, depending upon the length of time and the purpose of the assay, as well as the configuration of the apparatus.

The meal pad may be dehydrated by any suitable means known in the art including air drying, heat drying, and/or lyophilization, and the like. As used herein, the terms "dehydrated" and "dehydration" have their conventional meanings in the art. The dehydrated meal pad will has less than about 5–10% water by weight, and will preferably contain essentially no free water (e.g., less that about 1%, preferably less than about 0.5%, more preferably less than about 0.1% water by weight). Significant levels of residual water in the dehydrated meal pad is undesirable because it may result in reduced shelf-life and increased incidence of spoilage.

After dehydration, meal pads may be stored at any suitable temperature, e.g., at ambient, refrigerated or freezing temperatures. The meal pads may optionally be stored in a carbon dioxide or nitrogen atmosphere. Typically, however, the meal pads may conveniently be stored at room temperature, e.g., in a sealed bag or container, optionally in the presence of a desiccant. In alternative embodiments, the meal pads may be stored under conditions of darkness or under conditions in which ultraviolet light (or other undesirable wavelengths of light) are reduced or eliminated.

Preferably, the meal pads of the invention may be stored for at least about 2 months, more preferably for at least about 6 months, more preferably for at least about one year, still more preferably for at least about two years, or even five years or longer at room temperature prior to use without substantial loss of their functional properties, as described hereinabove.

The meal pad may be reconstituted or rehydrated using any suitable liquid, including polar and non-polar solvents (e g., water, acetone, or mixtures thereof). The meal pad may be rehydrated by simply placing the dehydrated pad into a container of the liquid. Alternatively, the pad may be hydrated from the bottom by placing on a wet filter paper. Generally, the meal pad is hydrated with an aqueous liquid. A non-polar solvent may be used to incorporate non-polar compounds into the meal pad as described below. Typically, non-polar liquids will be evaporated from the meal pad prior to exposing insects thereto.

Dehydrated meal pads are preferably rehydrated to at least approximately their original wet weight or more. Those skilled in the art will appreciate that rehydration times will vary depending on the size, shape and composition of the meal pad as well as the nature of the rehydration solution. Typically, meal pads will be rehydrated for a period of time ranging from about one minute to about 24 hours, with rehydration times of about three to five minutes being most common. Larger meal pads may be conveniently rehydrated overnight.

The meal pad may be rehydrated with any amount of water that produces a hydrated meal pad with the desired properties. Typically, the meal pad is rehydrated to restore the water lost during the dehydration process, although excess liquid may also be employed.

Insecticides and other compounds may optionally be incorporated into the meal pad, for example, for the feeding disruption assays as described herein. In particular preferred embodiments, the compound is incorporated during the formation of the meal pad. Alternatively, the insecticide or compound is introduced during or following the hydration process. As described further in the Examples, lipophilic compounds may optionally be incorporated using an organic solvent prior to rehydration. According to this embodiment, the organic solvent is preferably evaporated off prior to rehydration with an polar (preferably, aqueous) solution.

Incorporation during the hydration process is preferred. Incorporation of the insecticide or other compound at the point of use (i.e., right before, during or following rehydration) is particularly useful for assays in which it is desired to evaluate a number of compounds. The meal pads may be prepared and sold as "blanks", and the individual compounds added to one or more meals pads during (or after) rehydration. "Blank" meal pads may also be conveniently employed by other end-users to screen a compound or compound of interest, e.g., by a producer in a field environment testing for resistance to a particular insecticide.

Apparatus for Conducting the Present Assays.

Apparatus for carrying out the present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1B:
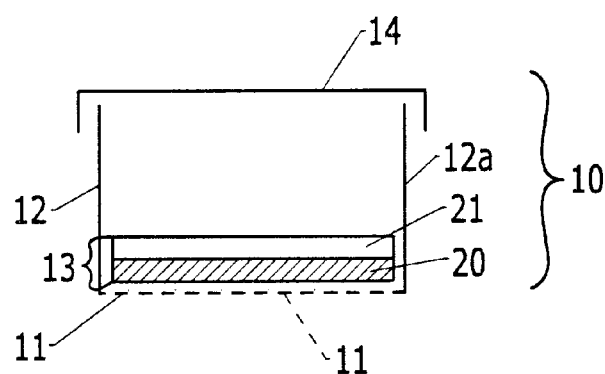

As shown in FIGS. 1A and 1B, an apparatus for conducting the feeding disruption assays of the present invention comprises a container or chamber 10 for housing insects. The container 10 comprises a floor 11 with sidewalls 12 extending upward from the floor 11 to define an open-topped. cavity. A removable cap or other seal member, such as an adhesive polymer film (e.g., mylar) 14 is attached to the container 10, so that the open end portion of the container can be closed. The container sidewalls 12 may be essentially perpendicular relative to floor 11, or angled relative thereto; the container 10 may be of any convenient shape including but not limited to cylindrical, cup-shaped and square.

Within the container and resting on the floor 11 is an insect-consumable dehydrated (i.e., hydratable) insect meal pad 13 as described above. In the particular embodiment shown in FIGS. 1A and 1B, the meal pad 13 has been coated on top of a mesh substrate layer 20 (e.g., a substrate layer having an open or porous paper, mesh or web structure). In other embodiments, the mesh substrate layer 20 is omitted. The insect meal contains nutritional components suitable to support the particular insect species or genus for which the container is intended.

In particular preferred embodiments, the dehydrated insect meal pad 13 is sized to cover essentially all of the floor 11 within the container; by essentially all it is meant that any gap between the meal pad and container sidewall is small enough that insects housed in the container cannot fit in said gap. The insect meal pad 13 may be formulated to contain a predetermined amount of insecticide within the insect meal layer, and may also contain a marker within the insect meal layer (such as Trypan Blue, discussed above).

Figure 1C:
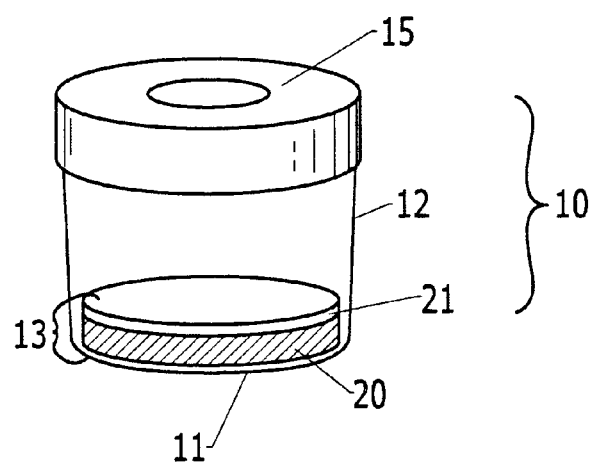

An alternative embodiment is a container according to FIG. 1A or 1B, but having a ceiling 15 rather than a removable cap. The ceiling 15 has formed therein an aperture or hole sized to admit the insect intended to be housed in the container. A still further embodiment is a container according to FIG. 1C, having a ceiling 15 without an aperture formed therein, but having an aperture or hole formed in sidewalls 12.

A further embodiment of the present apparatus is a container having a floor, sidewalls and a ceiling defining an interior space and containing an insect meal pad therein, and having at least one hole or aperture formed in the ceiling or sidewalls of the container. The container is sized according to its intended use, and is of a size suitable to house the insect for which it is intended.

The top surface or seal 14 and/or sidewalls 12 of the container 10 may optionally be perforated to allow the exchange of gases between the container 10 and the outside environment. Preferably the container 10 is made of transparent or semi-opaque material. Suitable materials include, but are not limited to, plastics, silicone, glass, and cardboard. The container 10 may be made of a material that is suitable for re-use (such as silicone), or a disposable material (such as cardboard). Preferably, the material is compatible with exposure to organic solutions. The container 10 is sized according to the intended use; a container designed for the feeding disruption assays as described herein may be a cylindrical container of about ½ inch in height and about ½ inch in diameter. The container will generally be larger for insect rearing purposes (e.g., about 2 to 4 inches in height, and about 1.5 to 2 inches in diameter).

As shown in FIG. 1B, the floor 11 of container 10 may optionally be perforated or foraminated so that the meal pad is in fluid communication with the exterior of the container (e.g., conductive to fluids such as liquid or permitting air into the container 10). The floor 11 may, for example, be formed as or comprise a section that is a grid, latticework or mesh. Alternatively, the floor 11 may be made of a material that is permeable to water, such as cardboard, nitrocellulose, nylon or filter paper (e.g., Schleicher & Schuell 803C).

The sidewalls 12 and seal 14 of the container 10 may be made of the same permeable material as the bottom surface, or of a different (permeable or impermeable) material. The seal 14 may be any material that seals the container 10 and may be conveniently applied and removed.

The exterior of the floor may optionally include ridges, bumps, extensions or legs, so that when placed on a level surface, the floor 11 is slightly elevated off of an underlying surface. Alternatively, sections of the sidewall(s) may extend downward past the floor 11 so that the floor 11 is slightly elevated from any level surface on which the container 10 is placed.

In use, the container 10 may be placed in a shallow tray of a rehydrating solution (e.g., water) so that liquid passes through the floor 11 to hydrate the meal pad 13 contained therein. Alternatively, container 10 is placed on a wet material (e.g., paper towels or filter paper) and the meal pad 13 is hydrated by absorbing liquid from the wetted material. As a further alternative, the meal pad 13 is hydrated by adding liquid directly to the meal pad 13, typically from the open top of the container 10.

The hydratable meal pad 13 may be hydrated with any suitable solution (e.g., an aqueous solution), as described above, including solutions containing an appropriate concentration of insecticide and/or marker useful in feeding disruption assays according to the present invention.

In those embodiments in which the floor 11 of the container 10 is conductive to liquid, a layer of an open-pored fiber or mesh (e.g., a glass fiber or polysulfone fiber paper) may optionally be placed or adhered to the top of the floor 11. This layer may provide better adhesion for the meal pad 13 to the floor 11. In addition, the open-pore structure may advantageously provide hydration control and/or promote penetration of the liquid through floor 11 and into the meal pad 13. This particular embodiment preferably includes an annular ring 30 (e.g., washer) or other platform placed on top of the meal pad.

In a further embodiment of the present apparatus, a dehydrated meal pad is placed atop an essentially flat supporting surface. A container such as that of FIGS. 1A, 1B or 1C, but lacking a floor 11 or having a perforated or foraminated floor 11 or, alternatively, a floor 11 with an aperture formed therein, is placed on the meal pad to isolate a test area of the meal pad. A plurality of containers may be placed on the meal pad, or an array of containers affixed together into a unit may be placed on the meal pad. The meal pad is hydrated, either prior to or after placement of the test containers. In a preferred embodiment, the supporting surface that carries the dehydrated meal pad is perforated or formed as a grid, lattice or mesh; in use the supporting surface is placed in a hydrating solution (e.g., an aqueous solution), so that the solution comes in contact with and hydrates the meal pad.

In one particular embodiment, a container lacking a floor 11 is placed on top of, and completely surrounds, a meal pad 13 supported on an essentially flat surface to form a closed container 11. In preferred embodiments, the meal pad 13 is placed on top of, or adhered to, a relatively rigid supporting surface (e.g., plastic or cardboard) to which the sidewalls 12 of the container 10 attach. For example, the sidewalls 12 may interlock with the supporting surface on which the meal pad is placed to form a sealed container with a floor.

In a further embodiment of the present apparatus, an annular ring 30 or other platform is placed atop the meal pad, leaving a central portion of the meal pad exposed and accessible to insect feeding. By exposing only a central area to insect feeding, the majority of feces produced by the insects are deposited on the annular ring covering the perimeter of the meal pad, and are easily observed. The surface of annular ring 30 is essentially flat, and preferably has an outer diameter essentially equal to that of the meal pad or that of the interior of the container in which it is used (see FIG. 1D). The central opening of the annular ring 30 may be of any suitable size (e.g., about 2 to 4 mm), and will vary depending on the insects with which it is used. Preferably, the diameter of the opening is less than the length of the insect being housed therein so as to promote feces deposition on the exposed surface of the ring and not on the meal pad, e.g., to promote visualization and detection of the feces.

Figure 1D:

The annular ring may be relatively thin, e.g., as shown in FIG. 1D. Alternatively, the annular ring may be of a depth to form a cylinder with a hollow space formed therein (see FIG. 2A). According to this embodiment, the center of the cylinder is filled with the meal pad with the top surface exposed to insects.

Preferably the annular ring or platform is of a color that contrasts with the color of feces produced by the insects being tested, for easy counting and identification. White or light-colored meal pad covers are suitable for use with test diets containing Trypan Blue. Annular rings or other platforms may be made of any suitable material, including but not limited to cardboard, nylon (e.g. nitrocellulose, PVDF) and plastics (e.g., polystyrene). The insects will typically prefer to walk on the surface of the annular ring or platform than the meal pad itself. In addition, the annular ring or platform may assist with hydration control of the meal pad and reduce the likelihood of the meal pad drying out, as well as limit the access of the insect to the space between the meal pad and the side of the container, and hold the meal pad to the bottom of the container.

The annular ring or platform may further contain, be manufactured of, or be coated with a substance that reacts with feces produced by the test insects to produce a mark on the annular ring or platform. For example, the meal pad test diet may contain a marker substance that reacts with the annular ring or platform to produce a visible mark or chemically detectable reaction thereon.

This embodiment of the invention may be preferably and advantageously employed in high through-put assays to screen compounds for insecticidal activity (alternatively, to detect resistance in insects or to distinguish among insect species based on relative insecticide resistance). The platform surface of the ring is preferably of a color that contrasts with the color of the feces (e.g., blue feces on a white or other light colored background), so that an automated digital imaging system may be used to detect feces production. Alternatively, a digital imaging system may be programmed to detect particles that are greater than a specified size, so as to distinguish feces from the insect.

Figure 2A:
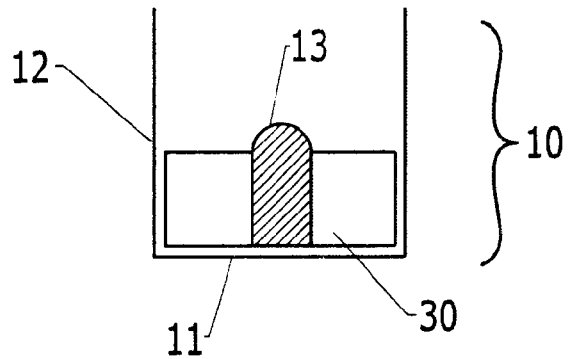

Accordingly, in another preferred embodiment, the annular ring 30 forms a cylinder as shown in FIG. 2A. The meal pad 13 fills the center of the annular ring and provides an exposed surface for insects placed in the container 10. The annular ring preferably covers all or substantially all of the floor 11 of the container 10, so that insects cannot enter the space between sidewalls 12 and the annular ring 30. Insects placed in container 10 will deposit feces on the surface of the annular ring 30 which may be readily detected, e.g., with the naked eye or an automated imaging system.

Figure 2B:
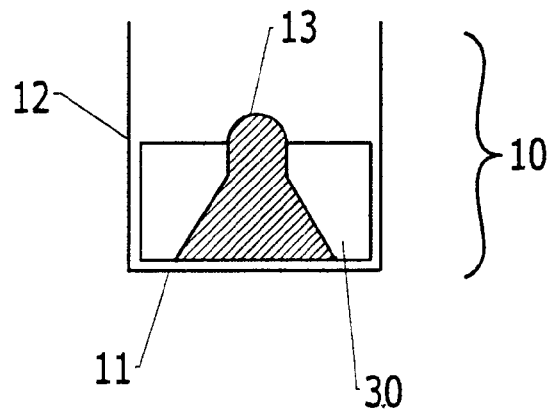

In a more preferred embodiment shown in FIG. 2B, the annular ring forms a cylinder, the center of which has a funnel shape, where the expanded end of the funnel is typically placed on the floor of the container, and the top of the ring forms a platform surface for the insects.

The annular ring and meal pad may be placed in the container 10 and optionally adhered to the floor 11 and/or sidewalls 12 of the container.

In yet a further preferred embodiment, a cylinder-shaped annular ring and dehydrated meal pad according to the invention (e.g., as shown in FIGS. 2A and 2B) are provided to the end-user. The annular ring is sized so as to be compatible with standard-sized containers or multi-well plates (e.g., commercially available 2-well, 4-well. 8-well, 24-well, or 96-well plates, and the like). The end-user may place the annular ring containing the insect meal in the cup or well(s) to provide a container for carrying out the inventive feeding disruption assay. This embodiment is particularly convenient for carrying out screening assays to identify compounds with insecticidal activity (or other assays using the feeding disruption assay as described herein) using standard multi-well plates and an automated digital imaging device (e.g., an ELISA plate reader).

In other particular embodiments of the apparatus, the hydratable meal pad is a small "disk" or "lens" (e.g., formed from about 20 to 50 µl of the meal pad formulation) on the floor (e.g., filter paper, nitrocellulose, cardboard, plastic) of the container. The floor of the container will typically be conductive to liquid to maintain the hydrated state of the relatively small meal pad. The floor may be water conductive to liquid because of holes, perforations or foraminations or, alternatively, because the floor is composed of a conductive material (e.g., filter paper such as Schleicher & Schuell 803C, as described above). The top of the container may be sealed with a removable top (e.g., plastic or cardboard, as described above). The floor may further include an annular ring or other platform for the insects to walk on and/or an open-pore paper on top of the bottom layer.

Figure 3:
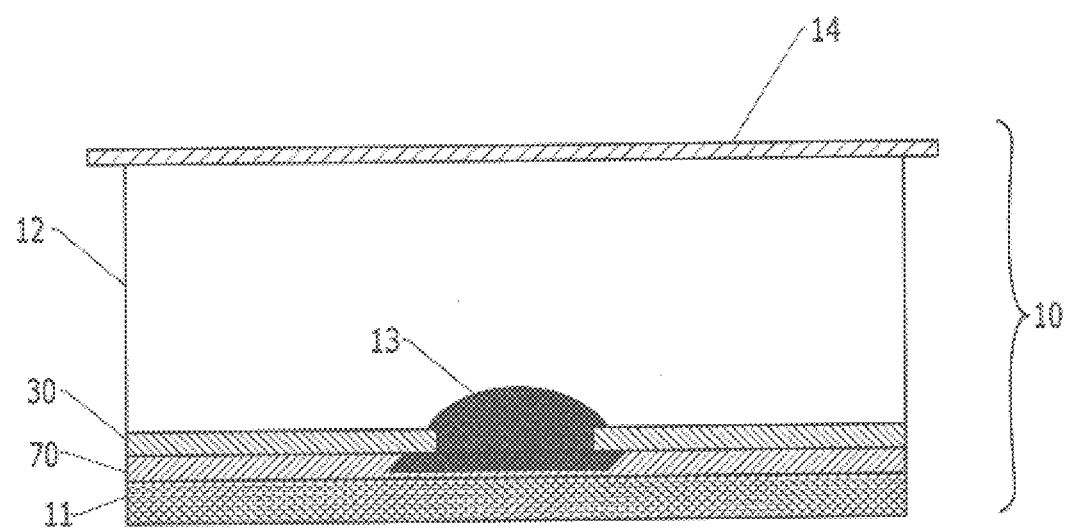

One particular preferred embodiment of the apparatus is shown in FIG. 3. A container 10 is shown with seal 14 formed from a removable top. The sidewalls 12 extend upward from floor 11. The floor 11 is composed of a permeable substrate (e.g., filter paper, as described above), on top of which is placed an open fiber layer 70 (e.g., a glass paper or plastic fiber paper), and a membrane or plastic platform to form an annular ring 30. The meal pad 13 is dispensed on top of the hole in the annular ring 30 so that it spreads to completely cover or substantially completely cover the opening in annular ring 30. The meal pad penetrates into the open fiber layer 70, providing better adhesion for the meal pad and facilitating hydration of the meal pad through the floor 11 of container 10. The meal pad is preferably hydrated by placing the container 10 (or an affixed array of containers) into a tray containing rehydrating solution or by placement onto a wetted material such as filter paper or paper towels.

A plurality of containers 10 may be affixed together, for example in a 4×4 array, 4×6 array, 10×10 array, etc., to provide a unitary multi-chambered apparatus for use in rearing or testing a plurality of insects. The containers are preferably affixed together so that the bottom surfaces of the containers form a plane, i.e., are aligned. This particular embodiment may be advantageously employed for high throughput screening of compounds and for detection of an indicator marker (e.g. a colored dye or fluorescent marker) using an automatic plate reader.

A particular preferred multi-chambered apparatus 40 is shown in FIG. 4. A plurality of containers 10 are affixed together to form a multi-chambered plate 50. The top surface or seal 14' is a cover that fits over the top of the multi-chambered plate 50. Preferably, as shown, the top surface or seal closes off each individual container within the multi-chambered apparatus, so that insects may not escape one container and enter another. For example, the individual containers may be sealed off. with adhesives. In other respects, seal 14' is similar to seal 14 described above.

Figure 4A:
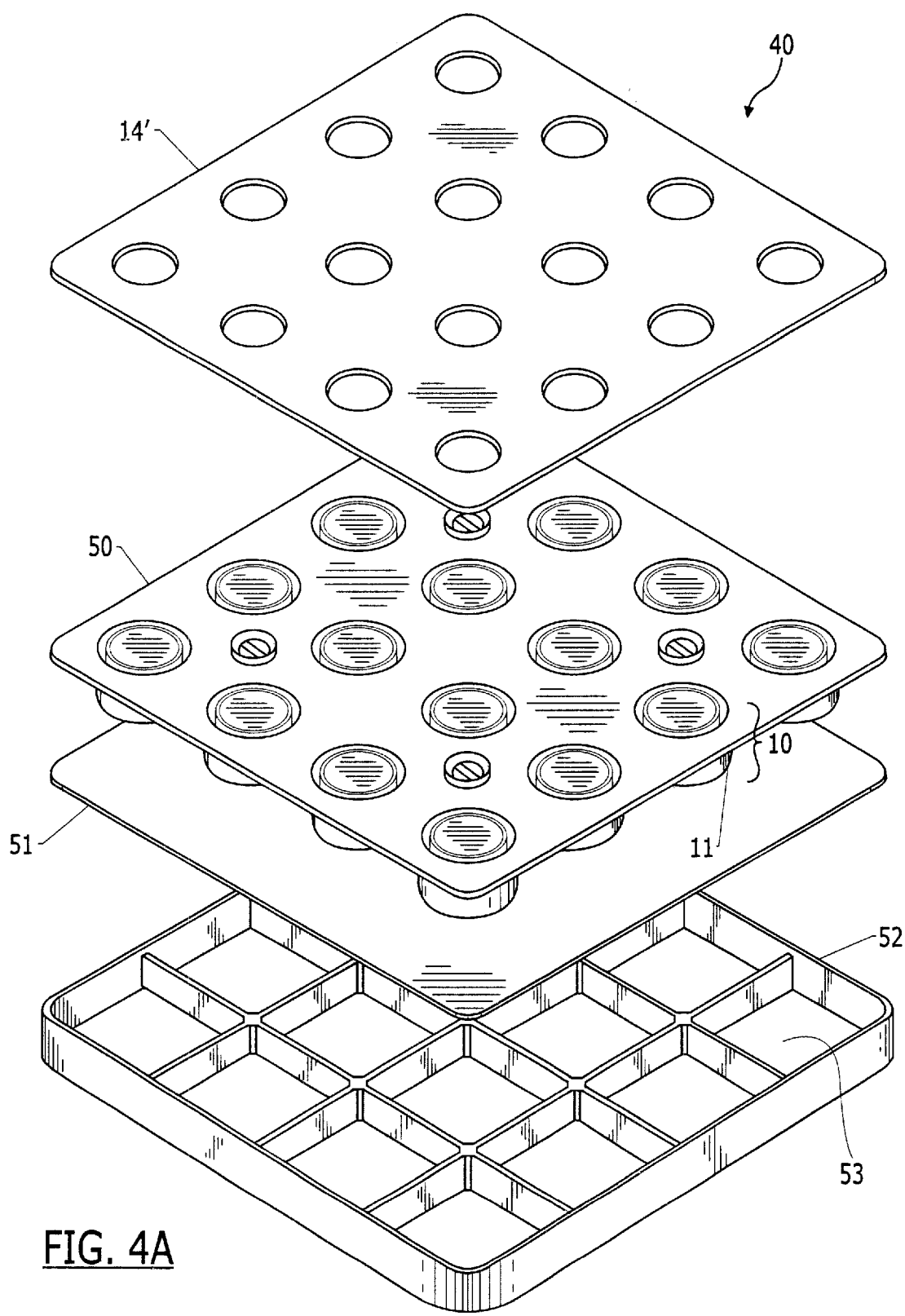

Hydratable meal pads 13 are provided in each of the containers 10 as described above. The floor of each container 11 is preferably permeable to liquids, as described above. The meal pads are rehydrated by placing the multi-chambered plate 50 on a wetted material 51 (e.g., wet paper towels or filter paper) or in a tray 52 of rehydrating solution. The tray may contain a single space or may be divided into sections 53 as shown in FIG. 4A Different compounds may be conveniently added to each section 53 (e.g., for screening of multiple compounds). In alternative embodiments, some or all of the sections 53 are in liquid communication with each other. For example, an entire row may in fluid communication such that a compound may be added to the liquid in one section and be dispersed throughout the other sections in the row.

In particular embodiments, the hydratable meal pads 13 are formed to fit into the containers 10, and the multi-chambered plate 40 may be provided to the end-user with the hydratable meal pads 13 already contained therein. Alternatively, the meal pad 13 may be provided separately and inserted into the individual containers 10 at the point of use.

Figure 4B:
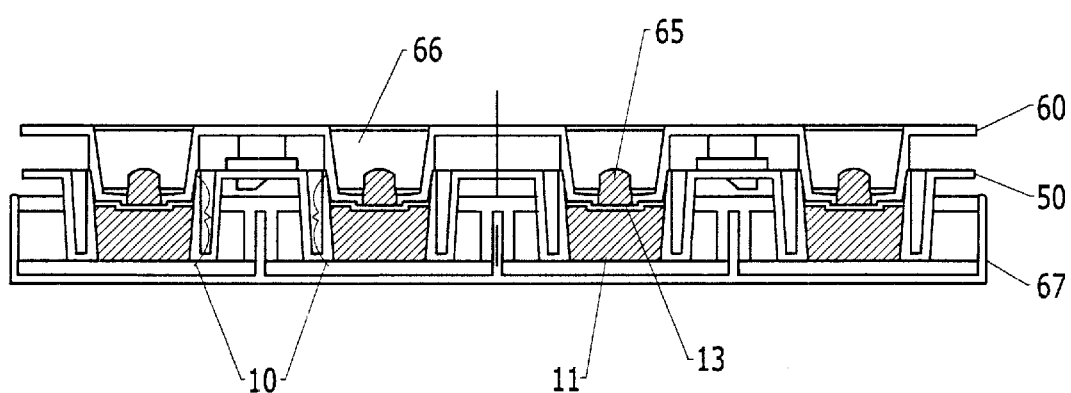
Figure 4C:
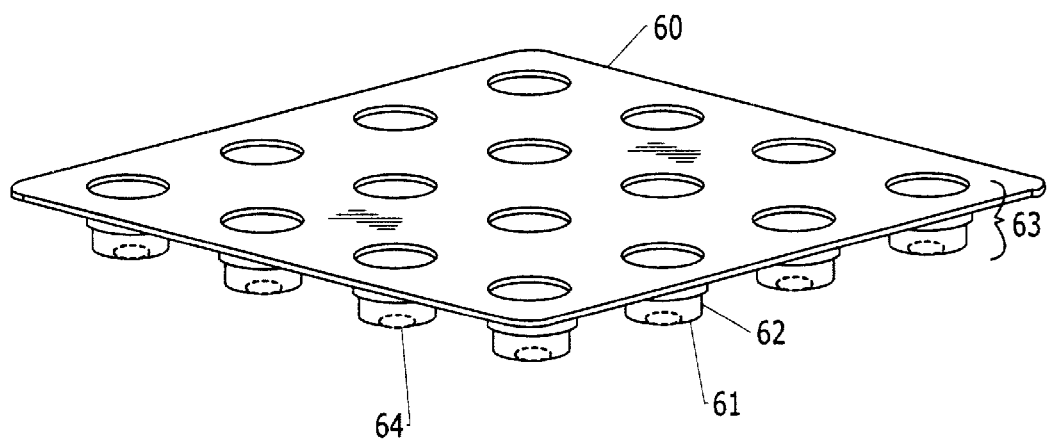

In a particular preferred embodiment 40' shown in FIG. 4B the liquid meal pad formulation is added to each container 10 to cover substantially the entire floor 11 thereof. While the meal pad is still liquid and prior to gelation, an upper well layer 60 is fitted on top of the multi-chambered plate 50. The upper well layer 60 may be of any suitable material, and is typically of a similar material to the multi-chambered plate 50 (e.g., plastic, silicone, glass, cardboard). Turning to FIG. 4C, the upper well layer 60 contains a plurality of wells 63 that align with, and fit into, the individual containers 10 of the multi-chambered plate 50. The individual wells 63 of the upper well layer 60 are formed with a base 61, sidewalls 62, and open top. There is an opening or aperture 64 formed in the base 61 of each well 63 of the upper well layer 60.

As shown in FIG. 4B and 4C, when the upper well layer 60 is fitted on top of multi-chambered plate 50, the liquid meal pad extrudes through the opening 64 in the base 61 of each well 63 in upper well layer 60, to form an exposed portion 65 of the meal pad 13 that is accessible to insects placed in the compartment 66 that is formed in the container 10 by placement of the upper well layer 60 on top of the multi-chambered plate 50. The base 61 of each well 63 of the upper well layer 60 surrounds the exposed portion 65 of the meal 13 and forms a platform for the insects to walk on. Insects may be placed into each well 63 through the open top, which may be sealed with a removable cap as described above. The apparatus 40' may optionally contain tray 67, which may be used to carry the other components or to rehydrate the meal pads through a conductive floor.

Following gel formation, the meal pad 13 is dehydrated while contained in the apparatus, essentially as described above. The meal may be rehydrated prior to use by placing the apparatus 40' into a tray 52 containing rehydrating solution or by placement onto a wetted material 53, as described above. Alternatively, the meal pads may be rehydrated by dispensing liquid from the top of the apparatus directly onto the meal pad.

Figure 5A:
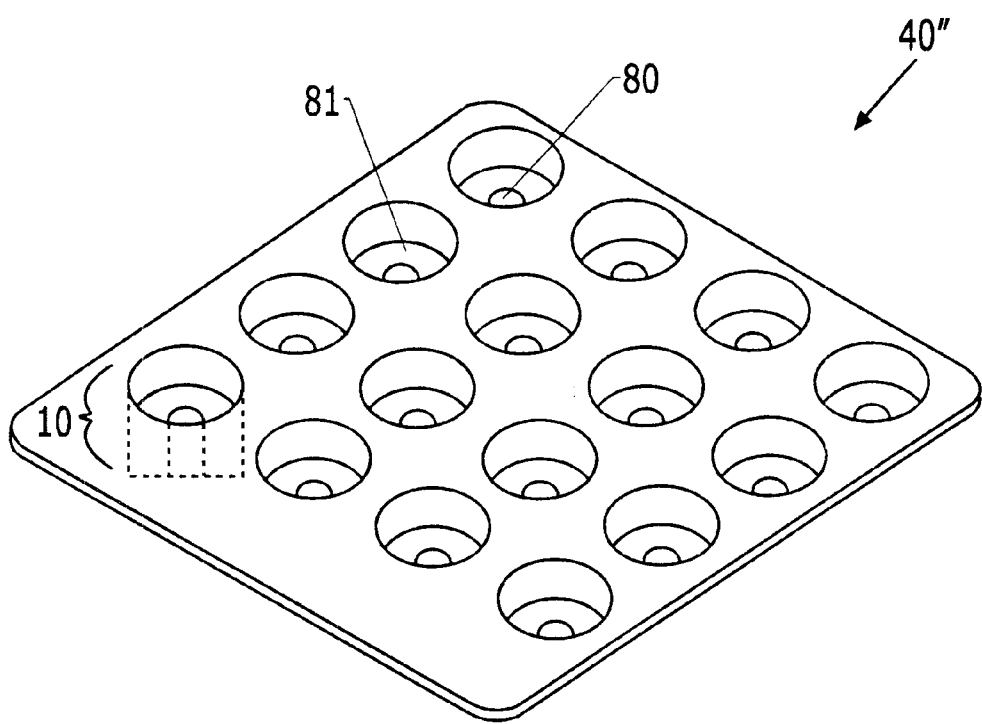

In a another particular embodiment 40", shown in FIG. 5A, a depression or well 80 is formed in the bottom of each container 10. The diameter of the well is typically about 20% to about 50% of the interior diameter of the container, preferably about 20% to about 40% of the interior diameter of the container (e.g., about one-third of the interior diameter of the container as shown in FIG. 5A). There is an essentially flat platform surface 81 around the perimeter of the well 80, on which the insects may walk and deposit feces. In particular preferred embodiments, the platform surface 81 is colored to contrast with the feces to facilitate detection thereof (e.g., white or other light color to contrast with blue feces). The apparatus 40" has a seal 14' as described above. In addition, the floor 11 of each container 10 may be permeable or impermeable (preferably, permeable) to liquid as described above.

Figure 5B:
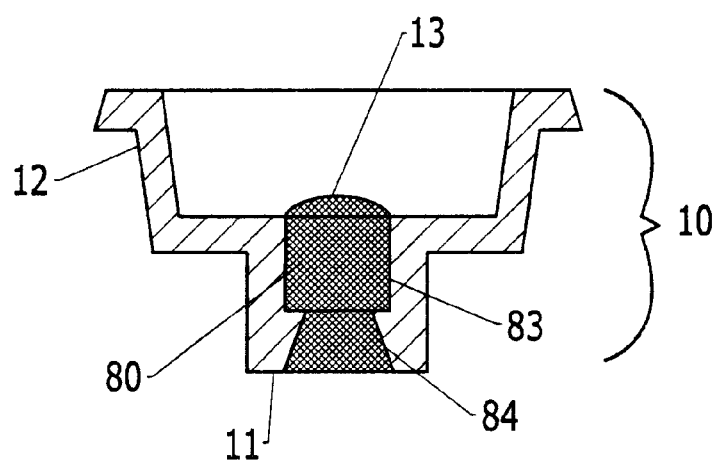

FIG. 5B shows a cross-view of an individual container of the apparatus of FIG. 5A. The sidewalls 12 of the container may be angled as shown in the figure or may be perpendicular with the floor 11. The meal pad 13 is formed within the well 80, and preferably fills the well 80 and extrudes therefrom so as to provide an exposed portion to the insects. The bottom portion of the well 80 may be shaped to affix the meal pad formed therein into the bottom of the well (for example, the bottom portion of the well may be expanded, as shown in FIG. 5B). The sides of the well 84 may be perpendicular (as shown) or angled. Alternatively, the sides of the well may have a funnel shape as shown in FIG. 2B.

Insects, insect eggs or insect larvae are placed in a container vessel ('test container'), on top of the meal pad enclosed therein. The meal pad is hydrated shortly before or after the placement of insects in the test container. Where the test container has a solid, water-impervious bottom surface, the meal pads are rehydrated by the addition of an aqueous solution to the top of the meal pad. Where the test container has a perforated bottom surface, it can be placed in a shallow tray of water or aqueous solution of insecticide. The meal pad may remain in contact with the aqueous solution during use to maintain hydration of the meal pad. The hydrating solution may contain a predetermined concentration of insecticide (e.g., a diagnostic dose of an insecticide for use in a resistance assay), or the meal pads may be formulated to contain a predetermined dose of insecticide.

It will be apparent to those skilled in the art that the various apparatus described above may be provided to the end-user with the meal pad already formed therein. Alternatively, the apparatus may be provided without the meal pad. Likewise, the meals pads of the invention may be provided independently of the apparatus or with only a portion thereof (e.g, a cylindrical ring containing the meal pad such as that shown in FIGS. 2A and 2B).

The Examples which follow are set forth to illustrate the present invention, and are not to be construed as limiting thereof.

EXAMPLE 1

Materials and Methods

Insects were reared in the laboratory at 27±1° C. with a 14:10 (light:dark) cycle on a standard artificial diet (Gould et al., 1995; Rose et al., 1995). The Wake strain of *H. virescens* used was originally collected in 1986 from tobacco in Wake county, N.C. The YHD2 strain was originally collected as eggs from seven tobacco fields in Yadkin County, N.C., in July of 1988. The YHD2 larvae were reared each generation for about seven days from egg hatch on 1000 $\mu$g of Bt toxin CryIAc (MVP, commercial grade, >98.0% $\delta$ endotoxin, Mycogen Corporation, San Diego) per ml of artificial diet and then transferred to insecticide-free diet for the remainder of development. The YHD2 strain is >2000-fold resistant to CryIAc, compared to the Wake strain (Gould et al., *J. Econ. Entomol.* 88:1545 (1995)).

During the course of these studies, the Bt toxin LC50s for the YHD2 and Wake strains were 2952 (95% confidence interval, 2247–3604; slope 3.23) and 0.0017 (0.0002–0.0038; 1.03) $\mu$g CryIAc/ml diet, respectively, using a seven day mortality assay on neonates. Mortality data were analyzed using probit analysis (PROC PROBIT, SAS 1991). Based on the low LC50 for Wake tobacco budworms versus that for YHD2, the Wake strain is designated as Bt susceptible.

Hybrid F1 larvae were obtained for testing from a YHD2 (female)×Wake(male) cross with 100 insects from each strain. This cross was duplicated and studies conducted with the F1 generation from each duplicate. The LC50 was 0.129 (95% confidence interval, 0.091–0.178; slope 3.19) $\mu$g CryIAc/ml diet in the hybrid larvae.

In addition to testing larvae from artificial diet, Wake and YHD2 larvae were reared from egg hatch through the third stadium on cotton plants, *Gossypium barbardense* (variety "Delta Pine Nutty"), in the greenhouse at 25° C. during the day and 18° C. at night (12:12, light:dark). Plants containing different strains were isolated by a distance of 10 meters to prevent cross-contamination. *H. zea* were obtained from cotton plants in Plymouth, N.C. and reared in the laboratory on the same artificial diet as that used for *H. virescens*.

EXAMPLE 2

Feeding Disruption Assay

The blue diet used in the feeding disruption bioassay is an agar based insect meal containing 20 mg of Trypan Blue (Direct Blue 14; Matheson Coleman & Bell, Norwood, Ohio) per 100 ml of standard artificial diet, and containing different concentrations of CryIAc (MVP, Mycogen). Larvae feeding on this colored diet produced blue feces which were easily distinguished by observation from feces derived from other food sources. Assays were conducted in 1-ounce clear plastic cups (Solo Cup Company, Urbana, Ill.; approximately 1½ inch in diameter and ¾ inches high) fitted with white cardboard tops, which are routinely used for insect rearing in the inventors' laboratories. The clear plastic allowed for the observation of blue feces without opening the container.

Third instars from Wake (Bt susceptible), YHD2 (Bt resistant), and YHD2×Wake hybrid strains of the tobacco budworm (*H. virescens*) were used. Instars weighed 30±5 mg and were reared either on standard artificial diet or cotton plants. Instars were starved for one hour and then transferred to clear plastic assay cups, one larvae per cup. The starvation treatment synchronized the beginning of feeding between individuals once transferred to the dye-containing diet. The effect of different concentrations of CryIAc (0 to 0.064 μg CryIAc/ml diet) on the production of blue feces was examined for one to 24 hours at 27±1° C. and 16: (light:dark). Studies were conducted in triplicate with 15 larvae per replicate. Once a diagnostic concentration and optimum assay time were identified from these experiments, the accuracy of resistance detection was investigated for individual resistant and susceptible neonates of *H. virescens*. These experiments were duplicated for 25 resistant and 25 susceptible budworms from two different budworm generations.

The diagnostic concentration for resistance detection was also investigated for its ability to distinguish Wake susceptible *H. virescens* from *H. zea*. In addition, dose response studies were conducted to identify a concentration of Bt that would distinguish resistant YHD2 neonates of *H. virescens* from *H. zea*. Dose response studies were duplicated for 25 resistant (HD2) tobacco budworms and 25 bollworms from two generations at different doses of Bt ranging from 0 to 1000 μg CryIAc/ml of blue diet.

EXAMPLE 3

Effects of Tyrpan Blue on Feeding

The rate of feces production was examined for third instars of both the Wake (Bt susceptible) and YHD2 (Bt resistant) strains of *H. virescens*, to examine the effects of adding Trypan Blue to the standard artificial diet (the "Blue diet"). Wake budworms produced 30.6 (90.5% confidence interval, 27.6–33.6) fecal pellets/hour/15 larvae on regular diet, and 25.5 (22.5–28.5) fecal pellets/hour/15 larvae on Trypan Blue diet. This difference, although small, was statistically significant as indicated by a significant diet×time interaction (F=6.05; df=1,24; P=0.0215) (PROC GLM procedure, SAS 1991). (Data not shown).

In contrast, the rate of fecal pellet production by the YHD2 strain did not differ between the regular and Trypan Blue diets, as indicated by the lack of a significant diet main effect (F+0.13; df=1,18; P=0.7248) and the lack of a significant diet×time interaction effect (F=0.08; df=1,8; P=0.7834) in an analysis of variance. The rates of fecal pellet production by YHD2 third instars were 34.4 (31.6–37.2) fecal pellets per hour per 15 larvae on the regular diet, and 34.9 (32.5–37.3) on the Trypan Blue diet. The YHD2 strain had a significantly higher feces production rate on Blue diet than the Wake strain (strain×time interaction significant; F=19.62; df=1,24; P=0.002). The difference, however, is small relative to the inhibitory effects of Bt on feces production and does not preclude the use of Trypan Blue as a feeding indicator in the bioassay. (Data not shown).

EXAMPLE 4

Resistance Assay on Homogenous Populations

FIG. 6 shows the rates of production of blue feces by susceptible (Wake), and resistant (YHD2), and hybrid (YHD2(female)×Wake(male)) third instars of *H. virescens* on Trypan Blue diet containing different concentrations of Bt toxin CryIAc. Each test was conducted in triplicate on 15 third instars per replicate. Although both susceptible (Wake) and resistant (YHD2) budworms produced blue feces in these studies, relatively little blue feces was produced through 24 hours by the susceptible budworms as compared to the resistant YHD2 strain. For example, after 24 hours at 0.032 μg of CryIAc/ml of diet, susceptible (Wake) budworms produced a total of 12 fecal pellets/15 larvae (0.8/larva) as compared to 470 (31/larva) for resistant (YHD2) larvae. FIG. 6. Even at 24 hours for concentrations as low as 0.008 μg/ml, fecal production was extremely low in the susceptible budworms (63, 4/larva) as compared to the resistant YHD2 strain (800, 53/larva).

These results indicate that a bioassay time of at least about four hours is needed to effectively discriminate between the resistant (YHD2) and susceptible (Wake) budworm populations at toxin concentrations of 0.008 to 0.064 μg/ml in these experiments. However, at least about 0.032 μg of CryIAc/ml blue diet appeared to be preferable as a diagnostic concentration for distinguishing resistant (YHD2) from susceptible (Wake) budworms since blue fecal production was minimal in the susceptible budworms at this concentration. Only 1.6 (0.1/larva), 5 (0.3/larva) and 12 (0.8/larva) blue fecal pellets were produced by susceptible larvae at 4, 8 and 24 hours as compared to 46 (3/larva), 129 (9/larva) and 470 (31/larva), respectively, for resistant budworms.

The detection of resistance in heterozygotes with a much lower LC50 than that of the YHD2 strain was also possible, although differences between the F1 hybrids and Wake larvae were not as distinct as those between YHD2 and Wake. The rate of fecal production in the YHD2×Wake hybrids was intermediate between that of YHD2 and Wake at all of the concentrations of CryIAc tested (FIG. 6). Because the overall production rate of blue feces was greatly reduced in the F1 hybrids as compared to the YHD2 strain, a bioassay time of about 24 hours was needed for a firm diagnosis. In these studies, a successful diagnosis of the hybrid was possible at concentrations ranging from 0.004 to 0.032 μg of CryIAc/ml of diet (FIG. 6). The 0.032 μg/ml dose at 24 hours produced 470 fecal pellets (31/larva) for the YHD2 strain, 68 (5/larva) for the hybrid and 12 (0.8/larva) for the Wake susceptibles. A single diagnostic concentration of 0.032 μg/ml can distinguish the Wake strain (LD50=0.0017 μg CryIAc/ml diet) from the highly resistant YHD2 strain (LD50=2952.0) after a minimum of about four hours and the YHD2×Wake hybrid (LD50=0.129) after 24 hours. In the present assays, differing resistance levels can be detected by simply changing the duration of the bioassay time from 4 to 24 hours.

EXAMPLE 5

Resistance Assay in Cotton-fed Larvae

The previous experiments were conducted on budworms reared exclusively on artificial diet. To examine whether plant reared, resistant (YHD2) and susceptible (Wake) tobacco budworms could be distinguished with this method, neonates from both strains were reared to the third stadium on cotton plants in the greenhouse and then assayed for resistance using the feeding disruption assay.

At a concentration of 0.032 µg of CryIAc/ml of Blue diet, the assay discriminated between the Wake and YHD2 populations reared on cotton (FIG. 7) similar to insects raised on artificial diet (FIG. 6). Essentially no blue feces were produced by the susceptible insects from cotton while at 24 hours, >140 fecal pellets were produced per 15 larvae by the YHD2 strain.

At a diagnostic concentration of 0.032 µg CryIAc/ml, 85±3.9 (1 SE)% of the resistant (YHD2) *H. virescens* produced one or more blue fecal pellets in 5 hours; 95±3.9% produced one or more blue fecal pellets in 9 hours, and 100.0±0.0% produced one or more blue fecal pellets in 14 hours (FIG. 8). The delay in fecal production by some resistant budworms is likely due to developmental differences at the beginning of the assay. By simply looking for the presence of blue fecal material and classifying larvae as resistant if blue fecal pellets were present, or susceptible if blue fecal pellets were absent, 95% of the YHD2 budworms could be accurately classified as resistant, and all of the Wake larvae could be accurately classified as susceptible after 9 hours. After 14 hours, 100% of the resistant insects could be correctly classified, but 2.2±3.9% of the Wake larvae had produced blue feces and would be incorrectly classified as resistant (FIG. 8). The initial classification of larvae as resistant could be verified by counting blue fecal pellets after 24 hours or by examining mortality a few days later.

These results establish that resistant and susceptible strains of plant-reared budworms can be distinguished using the present feeding disruption assay, and that insects reared on artificial diets can represent plant-reared insects in assessing feeding disruption assays.

EXAMPLE 6

Species and Resistance Diagnosis in Individual Insects

The above examples using third instars demonstrate the feasibility of using fecal production as an indicator of resistance to Bt toxins in the tobacco budworm. However, eggs are the easiest stage to collect from the field, and can be hatched by growers to provide neonatal larvae for resistance testing so that results are obtained early enough for corrective management. Additionally, in field samples, the populations will not necessarily be homogenous with respect to Bt susceptibility or species composition. Natural pest populations in cotton today include Bt susceptible *H. virescens* and Bt resistant *H. zea*.

Using the Blue diet described above and containing a discriminating concentration of 0.032 µg CryIAc/ml diet, and a 24 hour feeding time followed by a single observation, the present feeding disruption assay distinguished neonates of susceptible (Wake) tobacco budworm from the resistant bollworm with 100% accuracy (FIG. 9). Insects producing six or fewer fecal pellets were *H. virescens* and larvae producing ≧7 blue fecal pellets were *H. Zea* (FIG. 9). Only 1 out of 50 *H. virescens* produced six blue fecal pellets and 99% of *H. zea* produced ≧15 blue fecal pellets. The difference in fecal production between neonates of *H. virescens* and *H. zea* is greatly increased by waiting an additional 12 to 24 hours; during this time the budworms produced no additional fecal pellets. Additional characteristics that distinguished susceptible *H. virescens* budworms from resistant *H. zea* bollworms were apparent at 24 hours: *H. zea* larvae were noticeably larger at 24 hours, and most *H. zea* larvae maintained contact with the diet while the susceptible *H. virescens* larvae were physically away from the diet. In addition, mortality can be determined as a final check after 3–7 days.

EXAMPLE 7

Distinguishing Among Resistant Insects

Although the 0.032 µg CryIAc/ml diet was suitable to distinguish resistant from susceptible neonates of *H. virescens* at 24 hours, this concentration did not adequately distinguish the highly resistant *H. virescens* strain from *H. zea* (FIG. 9). Additional dose/response studies were conducted to determine a diagnostic concentration that would distinguish resistant YHD2 neonates from resistant *H. zea*. As shown in FIG. 10, using 500 µg CryIAc/ml in blue diet allowed discrimination of resistant YHD2 neonates from *H. zea*.

Using 500 µg CryIAc/ml in blue diet, 100% of *H. zea* produced no blue feces and the minimum fecal production by any individual YHD2 tested was five fecal pellets. As the Bt concentration approached zero, or was increased to 1000 µg/ml, the separation between species was not complete (FIG. 10). As discussed above, discrimination increased with assay time, and additional behavioral and developmental criteria exist that facilitate a correct diagnosis.

The above studies demonstrate that for susceptible *H. virescens* and *H. zea* and highly resistant laboratory *H. virescens* (YHD2), the present feeding disruption assay can effectively diagnose the presence of resistant species and resistance in individual insects. For use in field populations, assessment of regional variations in baseline levels of budworm and bollworm susceptibility to Bt, and potentially different levels of Bt resistance, will be useful to tailor the feeding disruption assay to particular regions. Studies of geographically diverse field populations of *H. virescens* and *H. zea* are conducted as needed to examine these questions and determine appropriate diagnostic doses.

EXAMPLE 8

Feeding Disruption Assay to Assess Resistance to a Carbamate Insecticide

The feeding disruption assay described above can also be used to detect resistance to chemical insecticides. *H. virescens* resistance to a carbamate insecticide was achieved by substituting a diagnostic dose of LARVIN® (thiodicarb; Rhone Poulenc Ag Co., Research Triangle Park, N.C.) for the Bt used in the preceding examples.

Two strains of *H. virescens* were utilized. The Wake strain was known to be susceptible to thiodicarb; the Macon Ridge strain was known to be resistant to thiodicarb. LARVIN® was added to a test diet at 1000 ppm and the larvae were allowed to feed; FIG. 11 graphs the production of fecal pellets over time. As shown in FIG. 11, the resistant and susceptible strains can be distinguished within hours based on fecal pellet production.

EXAMPLE 9

Field Studies

The eggs and young larvae of *H. zea* and *H. virescens* are indistinguishable by simple observation in the field. Neonate larvae were collected from fields in Plymouth and Rocky Mount, N.C., and 110 larvae were assessed using a feeding disruption assay containing 0.032 μg/ml of Bt over 48 hours. The larvae were successfully diagnosed as either *H. zea* (82 larvae) or *H. virescens* (28 larvae) (data not shown).

EXAMPLE 10

Modified Feed Disruption Assay

The assay design for the feeding disruption assay described in the preceding Examples was modified to furnish a more stable and efficient dose delivery system in an effort to provide a format suitable for field and laboratory use. The studies described below examine the efficacy of the modified feeding disruption bioassay when applied to field strains of *H. virescens* and *H. zea* collected throughout the Southeast and South-central U.S. These studies were designed to validate the use of this novel bioassay approach for identification and resistance monitoring of both species.
Materials and Methods:
Insects.

Insects were routinely reared in the laboratory at 27±1° C. with a 14:10 (L:D) cycle and 55% relative humidity on a standard artificial diet (Burton, (1970) *J. Econ. Entomol.* 631969). Adults were fed a 20% sucrose solution. Four field strains of *H. virescens* and seven field strains of *H. zea* used in these studies were established from populations collected from eight states representing the southern United States cotton-growing region (Table 1).

Feeding Disruption Bioassays.

Trypan Blue (Direct Blue 14; Matheson Coleman and Bell, Norwood, Ohio) was blended with artificial diet, 20 mg dye per 100 ml diet. Blue diet aliquots were dispensed (100 μl per well) into 8-well microtiter plate strips (Nalge Nunc Int., Napersville, Ill.). The blue dye served as a marker of feeding on the assay diet, with larvae feeding on colored diet producing blue feces which were easily distinguished visually from feces derived from other food sources. Microtiter plate strips containing blue diet were frozen at −80° C. and lyophilized (Bench Top 6, Virtis, Gardiner, N.Y.; cold trap=−70° C., ~200 mTorr, ambient temperature=23° C.) for a minimum of 24 h in order to form hydratable meal pads. Meal pads were stored in the dark in sealed plastic bags with desiccant prior to use.

Meal pads were hydrated with aqueous dilutions of the *B. thuringiensis* CryIAc δ-endotoxin formulation MVP (Mycogen, San Diego, Calif.) at least 1 h prior to the start of assays. Fresh diet aliquots (100 μl) consistently lost 78–84% of their water content by weight during the lyophilization process. Therefore, meal pads were hydrated with 80 μl of MVP in distilled water (treatments) or distilled water only (controls). The insecticide concentrations referenced throughout this paper are in μg MVP per ml of diet, i.e. the final concentration of insecticide in hydrated diet, which is 80% of the concentration of the solution used to hydrate the meal pads. Strip caps (Nunc) were cut into single caps in order to seal wells of the microtiter plate strips individually, which facilitated observation within wells while not allowing neighboring larvae to escape. In order to reduce condensation within the wells and provide larvae with air, caps were punctured twice with a #3 insect pin. Bioassays were conducted at 27±1° C. with a 14:10 (L:D) cycle, and blue fecal pellets were counted at 24 h. Neonates were used in all assays and were exposed to assay diets within 24 h of hatch. The results from each assay are taken from two replicates of each dose, with each replicate consisting of 24 larvae, one larva per well. Control (no dose) treatments were replicated three times. Dead larvae (defined as no movement for 30 s after prodding with a blunt probe) at the assay endpoint (24 h) were discarded and not included in the reported results. For each surviving larva, the number of fecal pellets produced was recorded. Serial dilutions of the MVP formulation were used for meal pad hydration, with separate dilution series prepared for each replicate.

Statistical Analyses.

Following 24 h exposure to diet containing a known concentration of MVP (Mycogen), a surviving larva was designated as a 'feeder' if it had produced more than two fecal pellets and as a 'non-feeder' otherwise. The cut-off value of two fecal pellets was adopted because this provided the clearest separation between species. Probit analyses were applied to the dichotomized fecal pellet counts in order to compare strains, between and within species, with respect to the feeding disruption response. A probit model was then used to relate the proportion of non-feeders to dose (on a $\log_{10}$ scale). Probit curves were fitted separately for each insect strain, and a $NFC_{50}$ (non-feeding concentration$_{50}$; $\log_{10}$ of the MVP concentration resulting in 50% non-feeders) and slope was obtained for *H. zea*. Also, probit curves were compared across species and among strains within species using PROC GENMOD with LINK= PROBIT (SAS 1993) on the data for all strains combined, and fitting effects for species, strains within species, $\log_{10}$ dose, as well as dose by species and dose by strain within species interactions.

Probit estimates of the proportion of feeders at the diagnostic concentration for each strain were used to predict the properties of an assay involving exposure of a small number, n, of larvae in individual wells for 24 h to diet containing a diagnostic concentration of the MVP formulation (final MVP concentration in diet 0.04 μg/ml). Calculations were carried out to determine the probability of obtaining k=0, 1, 2, etc. feeders, assuming that n 10 randomly chosen larvae are subjected to the assay. The probability of a single randomly chosen larva being a feeder was calculated as $$pf = R^* pr + (1-R)^* ps \tag{1}$$

where pr is the probability of a larva being a feeder given that it is a 'tolerant' type (*H. zea*), ps is the probability of a larva being a feeder given that it is a 'susceptible' type (*H. virescens*), and R is the proportion of tolerant types in the sampled population.

Given an assay with n surviving larvae, the probability that k of the n are feeders was then calculated assuming a binomial distribution for k, based on n trials each with "success" probability pf. These binomial probabilities were obtained for cases corresponding to n=10; R=0.0 to 1.0 by 0.1; ps=0.02, pr=0.80. The values used for ps and pr were chosen as the most conservative estimates obtained from the probit analysis of the proportion of feeders at the diagnostic concentration for strains of the 'susceptible' and 'tolerant' species, respectively. The cases R=0 and 1.0 represent populations that are entirely susceptible and tolerant, respectively.

Assuming known values of ps and pr, the proportion of feeders, $\hat{p}=k/n$, from an assay on n randomly selected larvae, can be used to estimate R, the proportion of resistant types in the population, using the equation:

$$\hat{R} = (\hat{p} - ps)/(pr - ps) \tag{2}$$

The larger the number of larvae subjected to the assay, the greater the precision of this estimate of $\hat{R}$. To illustrate the precision associated with different sample sizes n, 95% confidence limits were obtained for R based on using the estimator R and assuming pr and ps known. These confidence limits were constructed by first obtaining confidence belts for pf as, for example, in Table A.15A of Steel et al. (In Principles and Procedures of Statistics: A Biometrical Approach, p. 636. McGraw-Hill, N.Y. (1997)), and then using the upper and lower limits for pf to calculate upper and lower limits for R via equation (2). These confidence belts for R were obtained for sample sizes of n=10, 50, and 100 larvae and assuming pr=0.98 and ps=0.15. The choice of values assigned to pr and ps is discussed in the results.

Results and Discussion:

Response Variability in Feeding Disruption Bioassays.

The previous Examples have described a bioassay using feeding disruption, evidenced by decreased fecal production, for the diagnosis of B. thuringiensis-resistance and species identification in individual neonates of H. virescens and H. zea. These studies were conducted on laboratory insect strains and determined that an optimum diagnostic concentration of the B. thuringiensis CryIAc formulation MVP (0.032 µg MVP per ml diet) resulted in a nearly complete shutdown of fecal production in susceptible H. virescens over 24 h. At the same dose, B. thuringiensis-resistant H. virescens and susceptible H. zea consistently produced more feces. In addition, all of the surviving larvae on control (no dose) diets from those laboratory strains produced feces at 24 h. In order to use the feeding disruption bioassay for the detection of resistance or determination of species composition in the field, the assay response in field-collected insects was determined. Significant geographic variability in toxicity to the CryIAc toxin among field strains has been previously reported (Stone and Sims, (1993) J. Econ. Entomol. 86:989; Luttrell et al., (1999) J. Econ. Entomol. 92:21).

Strains of H. virescens and H. zea established from field collections (Table 1) were studied using a modified version of the feeding disruption bioassay, where assay diet was lyophilized to form hydratable meal pads and CryIAc was incorporated during meal pad hydration. Insect strains were compared by their bioassay responses over a range of doses. Four H. virescens strains were bioassayed on a no-dose control and four MVP concentrations from 0.013–0.1 µg MVP per ml diet (FIG. 12). Production of 0–2 fecal pellets over 24 h at a concentration of 0.05 µg MVP per ml diet was observed in 100%, 95.5%, 95.5%, and 97.7% of Hv Franklin, Hv Johnston, Hv Quitman, and Hv Washington, respectively (FIG. 12). Due to the similarity of these responses to that of the previously characterized laboratory strain, where 88.0% of the susceptible H. virescens produced 0–2 fecal pellets in 24 h at a concentration of 0.032 µg MVP per ml diet (Examples 1–9), these strains were designated H. virescens field strains as B. thuringiensis-susceptible. However, atypical of the previous work, a proportion of each field population were non-feeders on no-dose control diet, producing ≦2 fecal pellets at 24 h (FIG. 12). The range was 4.6% in Hv Washington to 17.1% in Hv Franklin.

TABLE 1

H. virescens and H. zea strains used for B. thuringiensis feeding disruption bioassays

| STRAIN | STATE | LOCATION | SPECIES | HOST |
|---|---|---|---|---|
| Hv Franklin | Louisiana | Franklin Parish | H. virescens | velvet leaf |
| Hv Johnston | North Carolina | Johnston County | H. virescens | tobacco |

TABLE 1-continued

H. virescens and H. zea strains used for B. thuringiensis feeding disruption bioassays

| STRAIN | STATE | LOCATION | SPECIES | HOST |
|---|---|---|---|---|
| Hv Quitman | Georgia | Quitman County | H. virescens | cotton |
| Hv Washington | Mississippi | Washington County | H. virescens | geranium |
| Hz Alachua | Florida | Alachua County | H. zea | cotton |
| Hz Baldwin | Georgia | Baldwin County | H. zea | cotton |
| Hz Barnwell | South Carolina | Barnwell County | H. zea | cotton |
| Hz Harmon | Oklahoma | Harmon County | H. zea | — |
| Hz Irwin | Georgia | Irwin County | H. zea | corn, tobacco |
| Hz Nueces | Texas | Nueces County | H. zea | corn |
| Hz Washington | Mississippi | Washington County | H. zea | geranium |

Six H. zea strains (Table 1) were assayed by the feeding disruption bioassay with four MVP concentrations (0.4–400 µg MVP per ml diet) and a no-dose control (FIG. 13). Production of 0–2 fecal pellets over 24 h at a concentration of 400 µg MVP per ml diet was observed in 97.7% of Hz Baldwin, 89.5% of Hz Harmon and 97.6% of Hz Washington (FIG. 13). Less than 88.0% of each of three other H. zea field strains were non-feeders at 400 µg (FIG. 13), but 1200 µg MVP per ml diet resulted in a non-feeding response in 87.2% of Hz Alachua and in 100% of both Hz Barnwell and Hz Nueces. The similarity of the response of these field strains to that previously observed in a laboratory susceptible colony, where 98.0% of the susceptible H. zea produced 0–2 fecal pellets in 24 h at a concentration of 1000 µg MVP per ml diet (Examples 1–9) led us to designate the H. zea field strains (Table 1) as B. thuringiensis-susceptible. The Hz Irwin strain was also susceptible (data discussed later). A no-dose non-feeding response was observed but at lower frequencies than in H. virescens, ranging from 0.0% in Hz Alachua, Hz Baldwin and Hz Washington to 6.0% in Hz Harmon. Helicoverpa zea strains (FIG. 13) consistently produced more feces as neonates on control diet over 24 h than did H. virescens (FIG. 12). For example, >50% of larvae in five out of a total of six H. zea strains produced >45 fecal pellets per larva as compared to one of four H. virescens strains.

Probit curves relating $\log_{10}$ dose to the proportion of non-feeders were fitted for each strain of both species (FIG. 14). In this analysis, non-feeders (NF) are defined as larvae producing ≦2 fecal pellets in 24 h. The $NFC_{50}$ is the $\log_{10}$ concentration of toxin resulting in 50% of assayed insects producing ≦2 fecal pellets. Helicoverpa zea strains are clearly separated from H. virescens strains in this graph, corresponding to a highly significant difference between species averaging over strains (p<0.001; FIG. 14). There were also significant differences among H. zea with respect to the $NFC_{50}$s but not with respect to slopes. Heliothis virescens curves indicate that the doses used in these bioassays did not permit 50% of the larvae in any strain to produce >2 fecal pellets, so comparisons based on $NFC_{50}$s were not made within this species. It appears that feeding responses on diet containing an appropriate MVP concentration can serve to differentiate bollworm field strains from tobacco budworm (FIG. 14), as was previously shown for laboratory strains (Examples 1–9).

Species Diagnosis.

Based on the probit analysis in FIG. 14, a bioassay concentration of 0.04 µg MVP per ml diet was chosen as a diagnostic concentration to distinguish *H. virescens* from *H. zea*. Assay results using this diagnostic concentration are shown in FIG. 15. An additional *H. zea* field strain, Hz Irwin, was included in the analysis. Neonates from only two *H. virescens* strains produced >5 fecal pellets (2.2% of Hv Quitman, 4.3% of Hv Washington), while no *H. virescens* were observed to produce >11 fecal pellets at this dose (FIG. 15). Conversely, >90% of three *H. zea* populations (Hz Alachua, Hz Barnwell, Hz Baldwin) produced >15 fecal pellets at the same dose, suggesting that all neonates producing >11 fecal pellets on the diagnostic concentration can be identified as *H. zea* without ambiguity. It is evident that the respective feeding probabilities for ps (*H. virescens*) and pr (*H. zea*) from equation (1), on the diagnostic concentration of 0.04 µg MVP per ml diet, varied among populations and geographic regions sampled. For example, the feeding response in *H. virescens* ranges from 2.1% for Hv Franklin to 14.9% for Hv Quitman, while the feeding response in H zea ranges from 80.4% for Hz Washington to 100% for Hz Alachua and Hz Barnwell (FIG. 15).

To illustrate the assay properties for n=10 larvae, the probability of observing k feeders was calculated using equation (1). The most conservative estimates of feeding probabilities ps and pr were chosen, values which tend to underestimate the likelihood of neonates from the population being feeders on the diagnostic concentration of 0.04 µg MVP per ml diet. The relationship between the true proportion of 'tolerant' types (*H. zea*) in a population and the probabilities of 0–3, 4–6, or 7–10 feeders being present in an assay of ten randomly sampled larvae is represented graphically (FIG. 16). From this analysis it is apparent that the assay is most accurate at extremes in species composition within a population. For example, 0–3 feeding larvae out of a sample of ten are highly predictive of a low proportion of *H. zea* in the population. Similarly, 7–10 feeding larvae are highly predictive of a high proportion of *H. zea* in the population. The presence of 4–6 feeders is less predictive of the corresponding true population proportion, although still providing useful estimates.

A decision scheme for predicting insect control failures in *B. thuringiensis* cotton entails two possible classification errors. One error would be predicting that the insect population will be adequately controlled by the endogenously expressed insecticidal protein when control actually will not occur. The second possible error would be predicting an insect population will not be adequately controlled when control is adequate. While neither error is desirable, their consequences are not equal. The latter error (incorrect prediction of a high proportion of *H. zea* in the population) might lead to the application of an unnecessary control treatment, while the former (incorrectly predicting the population has a low *H. zea* proportion) may entail more serious repercussions, including the potential for significant crop damage. Therefore, a decision scheme based on the bioassay should be biased toward minimizing the risk of misdiagnosing a potential control problem. By choosing the most conservative feeding probabilities encountered among the field strains tested, FIG. 16 depicts such a scheme. Actual bioassay results will likely provide more accurate predictions than those indicated in FIG. 16, which was calculated using observed feeding probabilities that are the most negatively biased for each species in a mixed population.

A sample size of ten was chosen in the analysis presented in FIG. 16 in order to easily illustrate the predictive nature of the bioassay. The potential value of using larger sample sizes in order to increase the precision of predictions based on bioassay results, using the diagnostic concentration of 0.04 µg MVP per ml diet, is evident in FIG. 17. Here 95% confidence intervals were generated from assay results for sample sizes of n=10, 50, and 100. Feeding probabilities used to calculate these CIs are based on estimates from insect strains collected in south Georgia (pr=0.98, Hz Irwin; ps=0.15, Hv Quitman). Confidence intervals generated from feeding probabilities typical of other insect field strains produced similar curves (data not shown). The increase in prediction precision resulting from larger samples is readily apparent. For example, in a random sample of n=10, with eight feeders (80%) identified by the bioassay, 95% CIs place the true *H. zea* population proportion between 35.3 and 100%. In contrast, a sample of n=100 larvae, with 80% of larvae classified as feeders after bioassay, provides a prediction of 67.2–87.2% *H. zea*. The accuracy gained by increasing the sample size from 10 to 50 is shown to be larger than that resulting from an increase from 50 to 100 (FIG. 17). The choice of an appropriate sample size will, in part, be a trade-off between the level of sampling effort and the degree of confidence needed in the assay results, as is the case for any population analysis. In addition, the confidence intervals are smaller at true population extremes (FIG. 17), as was predicted earlier (FIG. 16). Resistance Detection. The same diagnostic concentration used to differentiate *H. virescens* larvae from *H. zea* (0.04 µg MVP per ml diet) may also serve to monitor for the development of resistance in *H. virescens*. As seen in FIG. 18A, this dose resulted in <1% of the insects producing >10 fecal pellets (arrow). Based on the susceptible budworm strains examined so far, the production >10 fecal pellets by a larva over 24 h at 0.04 µg MVP per ml diet would indicate potential resistance to *B. thuringiensis*.

It was observed that the *B. thuringiensis* susceptible *H. zea* field strains (FIG. 13) produced feces over a wider range of CryIAc doses than did *H. virescens* (FIG. 12). Feeding disruption bioassays with meal pads containing 400 µg MVP per ml hydrated diet resulted in >89% non-feeding response in three of the six *H. zea* susceptible field strains tested (FIG. 13). In order to establish an appropriate diagnostic concentration for *H. zea* resistance monitoring, the three strains with >10% feeding response at a diagnostic concentration of 400 µg per ml diet were bioassayed at 1200 µg MVP per ml diet (FIG. 18B). This dose resulted in a 100% non-feeding response in both Hz Barnwell and Hz Nueces, but 12.8% of Hz Alachua neonates remained feeders (>2 fecal pellets per larva). The Hz Alachua strain was consistently observed to be more robust (lower mortality, greater fecundity and shorter generation time) than the other *H. zea* strains used in these studies, which may have influenced the feeding response. As indicated by the arrow in FIG. 18B, <1% of all *H. zea* larvae assayed produced >6 fecal pellets at this dose. Based on these assay results from the susceptible *H. zea* field strains, a diagnostic concentration of 1200 µg MVP per ml diet provides a good initial reference point for the screening of potentially *B. thuringiensis*-resistant *H. zea*.

These studies demonstrate that the feeding disruption bioassay provides reliable species diagnosis in the budworm/bollworm complex. The greatest utility of this technology, however, may be for the rapid detection of resistance. *Heliothis virescens* is historically notorious for developing high levels of resistance to broad categories of control agents (Sparks et al., (1993) Insecticide resistance and the tobacco budworm: Past, present and future, pp. 149–183. In Reviews in Pesticide Toxicology, Volume 2. R. M. Roe and R. J. Kuhr [eds.], Toxicology Communications Inc., Raleigh, N.C.), and the use of both cotton and corn expressing *B. thuringiensis* toxin indicates that surviving *H.* zea may be selected by both hosts in early and late generations (Storer et al., (1999) Ecology and biology of cotton bollworm in reference to modeling Bt resistance development in a Bt cotton/Bt corn system. In Proceedings, 1999 Beltwide Cotton Conferences, pp. 949–952. National cotton Council, Memphis, Tenn.). The U.S. Environmental Protection Agency therefore mandates monitoring for the early detection of resistance in B. thuringiensis crops (Matten, (1998) Resist. Pest Manag. 10:3). The feeding disruption bioassay appears to be a practical and rapid method for resistance monitoring both in the laboratory and in the field.

EXAMPLE11

Hydratable Meal Pads for Bioassays, Toxicity Screening, and General Insect Rearing To investigate the utility of substituting lyophilized complete artificial insect diets for fresh diets, comparisons between fresh and freeze-dried lepidopteran diets were conducted. Hydratable meal pads were formed by lyophilizing standard artificial insect diets in an attempt to overcome some of the limitations imposed by the use of fresh diets in bioassays and insect rearing. The efficacy of incorporating bioassay toxicants secondarily (during meal pad hydration) was also investigated, using the feeding disruption bioassay as the model.

Materials and Methods:

Insects and Diets. Insects were routinely reared in the laboratory at 27±1° C. with a 14:10 (L:D) cycle and 55% relative humidity. A strain of the cabbage looper, Trichoplusia ni (Hübner) (Lepidoptera: Noctuidae), has been continuously reared in laboratory culture since 1985. Trichoplusia ni larvae were reared on a pinto bean-based diet (diet No. 2 of Roe et al., (1982) An. Entomol. Soc. Amer. 75:421) in 8 oz styrofoam cups (~20 insects per cup) with plastic lids. Adults were fed a 50% aqueous honey solution. Tn-MP are identical to T. ni with the exception that larvae were reared on lyophilized diet (meal pads) for seven consecutive generations. Tobacco budworm, H. virescens and bollworm, H. zea strains (Hv 97 and Hz 97, respectively) were established and annually supplemented with field collections of all life stages from North Carolina. Hv Washington is a strain of H. virescens collected as eggs off geranium in Washington Co., MS. All heliothine larvae (Heliolhis and Helicoverpa spp.) were reared on a soy protein-based diet (Burton, (1970) J. Econ. Entomol. 63:1969) in individual 1 oz clear plastic cups with white cardboard tops, and adults were fed a 20% aqueous sucrose solution.

Developmental Comparisons.

The appropriate agar-containing insect rearing diet (described above) for each of three lepidopteran species was used in all experiments. Diets consisted of fresh, frozen, meal pad and stored-meal pad types. Fresh diet denotes the diet used in normal colony rearing, made within 3 d of use. The frozen type is fresh diet incubated overnight at −20° C. and thawed for at least 4 h prior to use. Meal pads are frozen diet lyophilized for a minimum of 72 h (Bench Top 6, Virtis, Gardiner, N.Y.; cold trap=−70° C., ~200 mTorr, ambient temperature=23° C.) in 1 oz rearing cups. Stored-meal pads were kept in the dark in a glass desiccator at ~500 mTorr with Drierite (W. A. Hammond Drierite Co., Xenia, Ohio) for >90 d prior to use. Water loss due to lyophilization was consistently 75–85% of the original wet weight for T. ni and heliothine diet meal pads. Meal pads (fresh or stored) were rehydrated to original wet weight 1 h prior to use by pipetting ½ of the proper volume of distilled water to the pad surface and repeating after 1 min. Dual water aliquots were used for meal pad hydration in order to keep them from floating, which is undesirable because partially hydrated floating pads may bind to the rearing cup sides, resulting in air space between the meal pad and bottom of the cup. For each strain of insect, 30 neonates (within 24 h of egg hatch) were placed on each diet type, 1 larva per 1 oz plastic cup, 10 ml diet per cup. Trichoplusia ni development was compared on fresh, frozen, and meal pad (fresh and stored) diets. Tn-MP development was compared to that of T. ni by monitoring both strains on fresh diet. Hv 97 and Hz 97 were compared on fresh diet and both stored and fresh meal pads. Growth expressed as mean wet weight (mg) was plotted, starting when larvae were large enough to be weighed without injury (either 4 or 6 d from placement on diet) and recorded every 2 d until >90% pupation was reached. Reported pupal weights will be of either day 1 or day 2 pupae, depending on when pupation occurred relative to the day of observation. All developmental comparisons within a given strain were conducted simultaneously with insects from the same generation.

Meal Pad Hydration.

Experiments designed to quantify water and solute dispersal during the hydration of lyophilized diets were conducted on 400 $\mu$l heliothine diet cylinders (height=10.5 mm, diameter=7.0 mm). Heliothine diet was chosen for these studies because it is more easily prepared than T. ni diet, while having a similar agar content. In experiments where lyophilized diet cylinders were allowed to hydrate freely in excess water, cylinders were vertically oriented in a 24-well microtiter plate, 1 cylinder per well (well height=20 mm, diameter=16 mm), containing excess water (500 $\mu$l, depth=2 mm). These free hydration experiments resulted in water absorption only from the basal portion of the cylinder. Hydrated diet water weight determinations were made by baking in a convection oven for 4 h at 80° C. Additional baking (24 h) did not result in additional weight loss. When non-hydrated diet cylinders were baked 4 h they lost 3.6% dry weight (SD=0.8%), so water weights were corrected for this loss.

In experiments where 400 $\mu$l lyophilized diet cylinders were hydrated to original wet weight, water (or solution) was added by pipetting dropwise from the top in order to attain hydration through the apical surface. After hydration, cylinders were divided into three sections with a scalpel for subsequent analyses. Data presented for hydration experiments using both excess and original water volumes are mean values of three replicates ±1 SE of the mean.

Radiolabeled compounds used in solute dispersal studies were [$^{14}$C(U)] L-Amino Acid Mixture (American Radiolabeled Chemicals, Inc., St. Louis, Mo.), [10-$^{13}$H(N)] Juvenile Hormone III (DuPont NEN, Boston, Mass.), and 1$\alpha$, 2$\alpha$ [N]-$^3$H-Cholesterol (Sigma Chemical Co., St. Louis, Mo.). Octanol-water partition coefficient ($K_{ow}$) values were obtained by the method of Leo et al. (1971), and the coefficients reported are the mean value of 3 replicates. Standard errors of the means were consistently <1.5%. Radioactivity, reported as cpm, was determined in 3 ml Scintiverse cocktail (Fisher Scientific, Springfield, N.J.) on a Beckman LS1801 scintillation counter (Beckman Instruments, Fullerton, Calif.), and >90% of radioactivity was recovered in all experiments. Approximately 0.05 $\mu$Ci of radioisotope was used in the hydration of each 400 $\mu$l lyophilized diet cylinder, which were hydrated from the top to original wet weight as described above.

Bioassays.

Feeding disruption bioassays follow the method Examples 1–9. Bioassay diets contain 20 mg of the dye Trypan Blue (Direct Blue 14; Matheson Coleman and Bell, Norwood, Ohio) per 100 ml of diet. The blue dye serves as a marker of fecal origin, with only larvae feeding on blue diet producing blue feces. All bioassay results were taken from two replicates consisting of 24 insects per replicate. Dead larvae (defined as no movement for 30 s after prodding with a blunt probe) at the assay endpoint (24 h) were discarded and not included in the results in order to avoid interpreting mortality as a non-feeding assay response. Assays were conducted in clear 8-well microtiter plate strips (Nalge Nunc Int., Napersville, Ill.). Strip caps were separated with a scalpel to allow individual removal, facilitating observation of individual wells while not allowing neighboring larvae to escape. A #3 insect pin was used to puncture each cap twice, which permitted ventilation in order to reduce condensation within wells and provide larvae with air.

The original bioassay method was modified by substituting 100 $\mu$l meal pads (diameter=6 mm) for fresh diets. Except where noted, toxins were incorporated into the meal pads by hydrating with aqueous solutions containing appropriate concentrations of the B. thuringiensis CryIAc formulation MVP (Mycogen, San Diego, Calif.). Serial MVP dilutions were used in each assay, with dilution series for each replicate of a treatment made on different days. Hydration of 100 μl meal pads was by pipetting two 40 μl aliquots (water volume=80 μl) in order to prevent pads from floating in the wells, as discussed above. Lyophilized diet cylinders (400 μl) were hydrated to original wet weight as previously described with an aqueous MVP dilution, resulting in a final concentration of 0.04 μg MVP per ml diet. After 1 h, cylinders were divided into 3 sections with a scalpel and individual sections were placed in 8-well microtiter strips, 1 section per well. The feeding disruption bioassay was then used to assess the diffusion of MVP through the cylinder using one larva per cylinder section. All bioassay concentrations reported are final diet concentrations, and not those of solutions used to hydrate meal pads.

Statistical Procedures.

Effects of diet on pupal weights were analyzed by 3-way ANOVA for each species using a general linear models procedure (PROC GLM) (SAS Institute 1989). Main effect variables were diet, sex and date of pupation for *T. ni*, Hv 97, and Hz 97. Main effect variables comparing pupal weights between *T. ni* and *T. ni*-L were species, sex, and date of pupation.

Differences between pupation dates were determined for each species by 2-way ANOVA (PROC GLM) (SAS Institute 1989) with sex and diet as main effect variables. Differences between *T. ni* and Tn-MP pupation dates were analyzed by a 2-way ANOVA (PROC GLM) with species and sex as main effect variables. Standard deviations and standard errors were determined using Microsoft Excel 97 (Microsoft Corp., Redmond, Wash.).

Results and Discussion

Meal Pads for Routine Insect Rearing. Larval and pupal weights of three species of insects reared on fresh artificial insect diet and meal pads (stored and fresh) were compared. FIG. 19 plots developmental mean wet weights by sex of *T. ni* reared on 4 types of a pinto bean-based diet. In addition to fresh diet and meal pads, fresh-frozen-and-thawed diet was added to examine developmental impacts resulting from the freezing process alone. Empty symbols denote mean larval weights, while filled symbols represent mean weights of either 1 or 2 day-old pupae and signify that >50% pupation has been reached (FIG. 19). The time period reported for reaching >50% pupation was taken from all of the insects. Mean pupal weights are reported only for insects who reached pupation within 2 days prior to observation of >50% pupation. All diet varieties examined appear equivalent with respect to the rate of *T. ni* growth as fresh diet (FIG. 19).

In addition to the *T. ni* pinto bean diet, a freeze-dried soy-protein diet used for heliothine rearing was evaluated. Heliothis virescens (FIG. 20) and *H. zea* (FIG. 21) neonates were placed on fresh and meal pad diets, and developmental mean wet weights were plotted by sex. Meal pads containing heliothine diet provided for similar growth rates (as measured by mean weights and rate of development) as fresh diet (FIGS. 20 and 21). These studies indicate that freeze-drying of diets does not produce a negative impact on larval development.

Table 2 presents a more detailed comparison of pupal weight and development for all three species reared on fresh diet and hydratable meal pads. All insects that pupated by 18 d are included, and weights were recorded within 2 d of pupation. There were no significant differences between mean male and female pupal weights over each diet for *T. ni* (sex×diet interaction; F=2.67; df=3,93; P=0.0519), *H. virescens* (F=0.98; df=2,54; P=0.3806) or *H. zea* (F=2.80; df=2,59; P=0.0687). For *H. zea*, there was a significant difference in pupal weights averaged over males and females (diet main effect; F=10.27; df=2,59; P=0.0001), with larvae feeding on meal pads (fresh and stored) producing heavier pupae than those feeding on fresh diet. In addition, there were no significant differences within strains in the day of pupation by sex for *T. ni* (sex×diet interaction; F=2.23; df=3,109; P=0.0892), *H. virescens* (F=0.51; df=2,58; P=0.6059), or *H. zea* (F=0.59; df=2,71; P=0.5568) over the different diet types. These data indicate that for these three species, substitution of hydratable meal pads for fresh rearing diets does not negatively affect weight or developmental time to pupation.

TABLE 2

Comparison by sex of mean pupal weights and cumulative pupation for 3 species on different diet varieties

| Insect Strain | Diet | % Mortality* | Sex | n | Cumulative % Pupation Day 14 | Day 16 | Day 18 | Pupal Weight (Mean ± SE) |
|---|---|---|---|---|---|---|---|---|
| *T. ni* | Fresh | 0 | F | 17 | 82.3 | 100 | 100 | 217.8 ± 3.6 |
| | | | M | 13 | 38.5 | 92.3 | 100 | 243.9 ± 4.7 |
| | Frozen | 6.7 | F | 15 | 53.3 | 93.3 | 100 | 223.8 ± 3.2 |
| | | | M | 13 | 30.8 | 92.3 | 100 | 251.4 ± 10.1 |
| | Meal Pad | 0 | F | 15 | 86.7 | 93.3 | 100 | 231.6 ± 5.1 |
| | | | M | 14 | 85.7 | 92.9 | 100 | 246.7 ± 5.3 |
| | Stored-Meal Pad | 0 | F | 12 | 66.7 | 91.7 | 100 | 216.3 ± 4.8 |
| | | | M | 18 | 22.2 | 66.7 | 88.9 | 242.5 ± 4.5 |
| Tn-MP | Fresh | 0 | F | 15 | 66.7 | 86.7 | 93.3 | 229.6 ± 4.8 |
| | | | M | 12 | 50.0 | 91.7 | 100 | 258.4 ± 4.3 |

TABLE 2-continued Comparison by sex of mean pupal weights and cumulative pupation for 3 species on different diet varieties

| Insect Strain | Diet | % Mortality* | Sex | n | Cumulative % Pupation | | | Pupal Weight (Mean ± SE) |
|---|---|---|---|---|---|---|---|---|
| | | | | | Day 14 | Day 16 | Day 18 | |
| Hv 97 | Fresh | 6.7 | F | 9 | 100 | 100 | 100 | 298.5 ± 3.5 |
| | | | M | 19 | 78.9 | 100 | 100 | 285.8 ± 5.9 |
| | Meal Pad | 3.3 | F | 11 | 72.7 | 100 | 100 | 307.6 ± 6.8 |
| | | | M | 16 | 68.8 | 93.8 | 93.8 | 290.0 ± 12.6 |
| | Stored-Meal Pad | 48.3 | F | 6 | 66.7 | 100 | 100 | 283.4 ± 15.6 |
| | | | M | 9 | 77.8 | 88.9 | 100 | 291.5 ± 8.4 |
| Hz 97 | Fresh | 20.0 | F | 13 | 0.0 | 53.8 | 100 | 401.4 ± 15.7 |
| | | | M | 11 | 0.0 | 45.5 | 90.9 | 406.7 ± 20.5 |
| | Lyophilized | 10.0 | F | 13 | 38.5 | 92.3 | 92.3 | 431.6 ± 17.3 |
| | | | M | 14 | 7.1 | 92.9 | 100 | 444.9 ± 17.3 |
| | Stored-Meal Pad | 10.0 | F | 16 | 6.3 | 43.8 | 87.5 | 414.6 ± 13.3 |
| | | | M | 11 | 0.0 | 18.2 | 81.8 | 429.5 ± 13.0 |

*% Mortality is defined as the number of insects dead or not reaching pupation by day 20 divided by the total number of insects assayed.

The developmental effects of rearing multiple generations on meal pads were also evaluated. Tn-MP is a subpopulation of *T. ni* reared for seven consecutive generations on meal pads. In the eighth generation, Tn-MP and *T. ni* were reared on fresh diet and their development was monitored (FIG. 22). Rearing *T. ni* for multiple generations on meal pads resulted in larvae capable of growth and development indistinguishable from *T. ni* reared exclusively on fresh diet. Pupal weights for these two *T. ni* strains (Table 2) were significantly different (species main effect; F=7.85; df=1,45; P=0.0075), with Tn-MP pupae heavier than the parental *T. ni* pupae. There was no significant difference in the day of pupation between the sexes for the two strains on fresh diet (species×sex interaction; F=1.78; df=1,53; P=0.1883). In addition, no differences in fecundity or general robustness between *T. ni* and Tn-MP strains were observed during routine colony maintenance.

Freeze-dried diets provide the essential nutrition for insect growth and development similar to fresh artificial diets. The results clearly demonstrate that meal pads are reasonable alternatives for growth media, at least for the lepidopteran species observed. Feeding on stored meal pads did result in some increased mortality for *H. virescens* (Table 2) as compared with fresh meal pads. Proper packaging is essential for long-term storage of freeze-dried food items (Greensmith, (1998) Practical Dehydration. 2 d Edition. Woodhead Publishing Ltd, Cambridge, UK), and laboratory storage conditions may have permitted some diet degradation during storage. Further investigation may be required in order to increase the stability of lyophilized diets for long-term storage.

Meal Pads for Bioassays.

It was hypothesized that hydratable meal pads might serve as superior alternatives to fresh diets in insecticide screening and toxicity bioassays if they could incorporate toxicants uniformly, when introduced as solutes, during the hydration process. A series of experiments was devised in order to examine some of the physical parameters associated with the hydration of meal pads, including the diffusion of solutes through the diet matrix.

Meal Pad Hydration.

Water movement during meal pad hydration was examined in the presence of excess water and when hydrated to original wet weight. First, lyophilized heliothine diet cylinders (400 μl) were allowed to hydrate freely from the bottom in excess water. FIG. 23 shows the total water content during hydration as the percentage of original wet weight over time. Complete hydration was essentially achieved at 2 min, while extending the hydration to 60 min and 24 h resulted in only 102.1±2.4% and 102.3±0.7% of the original wet weight, respectively. At least for the heliothine diet tested, the total water absorbed over 24 h is only slightly higher than the original water content. In order to determine how water is distributed through hydrating diet, the cylinders were cut into three approximately equal sections at multiple time intervals after hydration initiation (FIG. 24). The water content is expressed as a ratio (water weight/dry diet weight) in order to provide an index of hydration which accounts for minor differences in the volume of cylinder sections. In as little as 2 min, water content in the middle and bottom sections is stable, while content in the top section is consistently lower at all time points, with differences diminishing through 24 h (FIG. 24). These results were expected since the bottom of the cylinder is submerged. Minimal hydration differences within cylinders at 24 h indicate that an excess water hydration protocol for meal pads will likely be acceptable for many applications. Free hydration in excess water may prove especially useful in situations where dispensing precise volumes is impractical, for example when time is critical or in the absence of dispensing tools. In. addition, the use of membrane filters for packaging of lyophilized foods has been previously reported (Schimmel et al., (1996) *J. Food Sci.* 61:579) as a method of preventing microorganismal contamination resulting from hydration with impure water. The use of such filters could eliminate the need for sterile or potable water in situations where it may not be conveniently accessed, for instance when meal pads are used in field bioassays or for the rearing of field-collected larvae.

Lyophilized diet cylinders (400 μl) were also hydrated to original wet weight from the top in a drop-wise manner. The disks were divided into three sections at 10 and 60 min, and the water content of each section determined (FIG. 25). At 60 min, there is slightly less water in the bottom section as compared to the top, while water content in the middle section is within 1 SE of both top and bottom. The cylinders retained minimally more water in the region closest to the point of hydration.

Solute Diffusion.

The diffusion of solutes through the diet matrix during hydration was examined for compounds of varying water solubility. Solutes were radiolabeled so that diffusion of minute concentrations, which are typical of those used for toxicity bioassays, could be easily quantified. Octanol-water coefficient ($K_{ow}$) values were determined for three compounds or mixtures; L-amino acids ($K_{ow}$=0.04), cholesterol ($K_{ow}$=0.46) and juvenile hormone III (JH III) ($K_{ow}$=165.33). Water, with compounds in solution, was used to hydrate 400 µl lyophilized diet cylinders from the top to their original water content. At 60 min the cylinders were divided into three sections and radioactivity in each section was determined (FIG. 26). These compounds are arranged on the X-axis in order of increasing hydrophobicity as indicated by $K_{ow}$. An approximately 10-fold difference in coefficient range exists between the more polar amino acid mixture and cholesterol. There was only a small difference in diffusion, however, with less activity detected in the bottom cylinder section for cholesterol than the amino acid mixture, while the top and middle sections were not different (±1 SE of the mean) for these compounds (FIG. 26). The dispersal of these two solutes through the cylinders follows the same profile as water (FIG. 25) over the same time interval (60 min). In contrast, essentially all of the JH III remained in the top cylinder section, where it contacted the matrix (FIG. 26). JH III is an extremely lipophilic compound (Schooley, (1977) Analysis of naturally occurring juvenile hormones—their isolation, identification, and titer determination at physiological levels, pp. 241–287, In R. B. Turner [ed.], Analytical Biochemistry of Insects. Elsevier Press, New York), which is evidenced by its high $K_{ow}$. Water solubility obviously influences the dispersal of compounds through meal pads during hydration.

Meal Pads for Bioassays.

The feeding disruption bioassay was used as a model to examine whether meal pads will function adequately when substituted for commonly used fresh diets in bioassays. A diagnostic concentration of 0.04 µg MVP per ml diet was chosen based on previous findings (Examples 1–9) that *H. virescens* neonates could be distinguished from *H. zea* at 24 h by differential fecal pellet production over 24 h. The same diagnostic concentration was also used to differentiate *B. thuringiensis*-resistant and susceptible *H. virescens*.

Incorporation of Toxins.

The Hv Washington strain has been shown to respond to this assay similarly to other field collected strains of *H. virescens*. FIG. 27A shows the fecal production response from Hv Washington on 100 µl meal pads hydrated to 0.00 (control) and 0.04 (diagnostic concentration) µg MVP per ml diet. These 100 µl meal pads were hydrated by immersion (FIG. 27A), while 400 µl lyophilized diet cylinders were hydrated dropwise through the apical surface. Cylinders were then divided into three sections, and Hv Washington neonates were monitored for fecal production, one larva per section (FIG. 27B). The feeding disruption responses between diet sections are similar, with the cylinder sections farthest from the site of toxin entry (middle and bottom) performing as well as the top section (FIG. 27B). While 10.4% of the population assayed on the diagnostic concentration with 100 µl meal pads produced >5 fecal pellets (FIG. 27A), the 400 µl cylinders resulted in only 6.3, 4.2, and 6.4% of the population producing >5 fecal pellets for the top, middle and bottom sections, respectively (FIG. 27B). These results suggest that MVP is distributed relatively evenly through meal pads during hydration. Pesticide formulations, such as MVP, are intended to make the active ingredients more water soluble in order to facilitate field application. Proper formulation may permit greater dispersal of hydrophobic compounds through meal pads than was previously seen with JH III in the absence of such carriers (FIG. 26). It is certainly reasonable to expect compounds to diffuse through hydratable meal pads at least as well as overlay methods, regardless of their relative polarity. The use of organic solvents to incorporate lipophiles prior to meal pad hydration has also been examined. In studies using acetone and hexane, the meal pad matrix was solvent-permeable, retained its structure and could be hydrated with water after solvent evaporation.

Comparison with Fresh Diets.

Meal pads and fresh diet aliquots (100 µl for each) were compared in the feeding disruption bioassay. Hv 97 neonates were assayed for fecal production at the diagnostic concentration of 0.04 µg MVP per ml diet over 24 h, and the percent of the population producing >2 fecal pellets per larva was compared among diets (FIG. 28). Hydrated meal pads performed equally as well as fresh diet in absence of toxin (FIG. 28; Bars A and C), with all larvae producing multiple feces. There were no differences in bioassay results using fresh diet where the toxin was incorporated during formulation (FIG. 28; Bar B), meal pads where the toxin was incorporated during hydration (FIG. 28; Bar E), and meal pads where the toxin was incorporated during diet formulation prior to lyophilization (FIG. 28; Bar D). MVP is apparently stable in diet during the lyophilization process (FIG. 28; Bar D), which has been reported previously (Stone et al., (1989) *J. Invert. Pathol.* 53:228).

These results indicate that meal pads perform as well as fresh diets in the bioassay, and that the MVP toxin may be incorporated either before or after lyophilization without altering bioassay sensitivity. Hydratable meal pads clearly offer a viable, if not preferable, alternative to traditional diet formats used in feeding bioassays. Meal pads can be produced in large quantities, eliminate the need for refrigeration, and extend shelf life. Bioassays are enhanced by meal pads due the ease of toxicant incorporation during hydration, as opposed to blending during diet formulation.

EXAMPLE 12

Larval feeding Disruption Assay for Spinosad Resistance

Spinosad was originally discovered in the actinomycete, *Saccharopolyspora spinosa*, and has been developed into an important new class of insecticides for control of lepidopterous pests in cotton and other crops (Thompson et al., (1997) *Down to Earth* 52:1). The principle active components of the commercial product, spinosad (Tracer®), are spinosyns A and D, which contain a tetracyclic core consisting of a 12-membered macrocyclic lactone fused to a 5,6,5-cis-anti-trans-tricyclic ring system. Also attached to the core is the amino sugar forosamine and a neutral sugar, 2,3,4-tri-O-methylrhamnose. Spinosyns A and D differ only by the presence of a methyl group at $C_6$ (Sparks et al., (1998) *J. Econ. Entomol.* 91:1277). Spinosad has only recently come into widespread use as an insecticide.

The Bt feeding disruption assay described above was modified to monitor spinosad resistance in tobacco budworms. Trypan Blue (Direct Blue 14, Matheson Coleman and Bell, Norwood, Ohio) was blended into artificial diet (described above) at the rate of 20 mg of dye per 100 ml diet. This diet also was formulated with 1.6 µg of spinosad active ingredient per ml diet. The spinosad was added to the diet as part of a 44.2% aqueous formulation provided to us by Dr. Clyde Sorenson (NC State University, Raleigh, N.C.). Several different concentrations of spinosad were investigated, but 1.6 µg/ml proved to be an optimum diagnostic dose. The blue indicator diet with spinosad was dispensed at the rate of 100 μl per well into 8-well microtitre plate strips (Nalge Nunc Int., Napersville, Ill.). The wells were sealed with strip caps (Nunc). In order to reduce condensation within the wells, caps were punctured twice with a #3 insect pin.

Hv Franklin (spinosad susceptible) and spinosad resistant (selected) neonates of the tobacco budworm were used in all assays and were added to the assay diet within 24 h of hatch. Hv Franklin has been previously shown to be representative of other field collected *H. virescens strains* in spinosad toxicity. Selection of our laboratory colony of tobacco budworms which were originally collected from various locations in North Carolina, with technical spinosad applied topically each generation, produced insects that were highly resistant to spinosad.

Bioassays were conducted at 27±1° C. with a 14:10 L:D cycle, and the number of blue fecal pellets produced were counted after a 24 h exposure of the neonates to the diet. Results were taken from two replicates consisting of 24 insects per replicate.

Several diagnostic concentrations of formulated spinosad were tested. An optimum diagnostic dose was 1.6 μg of active ingredient (spinosad) per ml artificial diet (FIG. 29). At this dose, 100% of the susceptible Hv Franklin tobacco budworms produced 0–2 fecal pellets while 100% of the Hv selected insects produced >2 fecal pellets in 24 h. Only a small fraction of the resistant budworms (2.3%) produced 3–5 pellets (FIG. 29). These studies demonstrated that the feeding disruption assay can be used for monitoring spinosad resistance in larvae of the tobacco budworm.

The foregoing examples are illustrative of the present invention, and are not to be construed as limiting thereof. The invention is described by the following claims, with equivalents of the claims to be included therein.

That which is claimed is:

1. A container for housing insects, comprising:

(a) a chamber having a floor, sidewalls extending from said floor and an open end portion;

(b) a seal member removably attached to said container and configured to close the open end portion;

(c) a dehydrated insect meal pad contained within said chamber; wherein the meal pad substantially covers the floor of said container; and (d) a platform layer partially overlying said meal pad.

2. The container of claim 1, wherein said meal pad comprises a dye that imparts color to insect feces and the color of said platform layer contrasts with the color imparted to insect feces by said dye.

3. The container of claim 2, wherein said dye comprises Trypan Blue.

4. The container of claim 1, wherein the floor of said chamber is formed of a material that is permeable to water.

5. The container of claim 4, wherein the floor of said container comprises nitrocellulose.

6. The container of claim 1, wherein said seal is a removable cap.

7. The container of claim 1, wherein said meal pad comprises an insecticide.

8. The container of claim 7, wherein said insecticide is a chemical insecticide selected from the group consisting of pyrethroids, carbamates, diamidides, organophosphates, organochlorines, spinosyns, and chloronicotinoids.

9. The container of claim 7, wherein said insecticide comprises a Bacillus thuringiensis toxin.

10. The container of claim 1, wherein said meal pad comprises a test compound to be assessed for insecticidal activity.

11. The container of claim 1, wherein the sidewalls of said container are formed of plastic.

12. An apparatus for housing insects, comprising a plurality of containers according to claim 1 affixed together.

13. A container for housing insects, comprising:

(a) a chamber having a floor, sidewalls extending from said floor and an open end portion;

(b) a seal member removably attached to said container and configured to close the open end portion;

(c) a dehydrated insect meal pad partially overlying said floor; and (d) a platform layer overlying meal pad, said platform layer having a hole therein, wherein said meal pad substantially overlies said hole.

14. The container of claim 13, wherein said meal pad comprises a dye that imparts color to insect feces and the color of said platform layer contrasts with the color imparted to insect feces by said dye.

15. The container of claim 13, wherein the floor of said chamber is formed of a material that is permeable to water.

16. The container of claim 15, wherein the floor of said container comprises nitrocellulose.

17. The container of claim 13, wherein said seal is a removable cap.

18. The container of claim 13, wherein said meal pad comprises an insecticide.

19. The container of claim 18, wherein said insecticide is a chemical insecticide selected from the group consisting of pyrethroids, carbamates, diamidides, organophosphates, organochlorines, spinosyns, and chloronicotinoids.

20. The container of claim 18, wherein said insecticide comprises a *Bacillus thuringiensis* toxin.

21. A container for housing insects, comprising:

(a) a chamber having a floor, sidewalls extending from said floor and an open end portion;

(b) a seal member removably attached to said container and configured to close the open end portion; and (c) a dehydrated insect meal pad contained within said chamber, the pad comprising a marker substance that imparts a detectable characteristic to insect feces.

22. The container of claim 21, wherein the floor of said container is conductive to liquid.

23. The container of claim 22, wherein the floor of said container is a permeable material.

24. The container of claim 23, wherein the floor of said container comprises nitrocellulose.

25. The container of claim 21, wherein the meal pad substantially covers the floor of the container.

26. The container of claim 25, further comprising a platform layer on top of said meal pad, wherein the platform layer does not cover the entire surface of the meal pad.

27. The container of claim 21, wherein said meal pad is a disk that covers less than all of said floor of said container.

28. The container of claim 27, further comprising a platform layer, said platform layer having a hole therein, wherein said meal pad substantially covers said hole.

29. The container of claim 21, wherein the meal pad substantially covers the inner surface of said seal.

30. The container of claim 21, wherein said meal pad is a disk that covers less than all of the inner surface of said seal.

31. The container of claim 21, wherein said seal is a removable cap.

32. The container of claim 21, wherein said floor is perforated.

33. The container of claim 21, wherein said meal pad comprises an insecticide.

34. The container of claim 21, wherein said meal pad comprises a test compound to be assessed for insecticidal activity.

35. The container of claim 21, wherein said marker substance comprises a dye that imparts one of color, fluorescence and luminescence to insect feces.

36. The container of claim 21, wherein the sidewalls of said container are made of plastic.

37. An apparatus for housing insects, comprising a plurality of containers according to claim 21 affixed together.

38. The container of claim 35, wherein said marker substance comprises Trypan Blue.

39. The container of claim 33, wherein said insecticide is a chemical insecticide selected from the group consisting of pyrethroids, carbamates, diamidides, organophosphates, organochlorines, spinosyns, and chloronicotinoids.

40. The container of claim 33, wherein said insecticide comprises a *Bacillus thuringiensis* toxin.

41. The container of claim 40, wherein said *Bacillus thuringiensis* toxin is a CryIAc *Bacillus thuringiensis* toxin.

42. The container of claim 13, wherein said meal pad a test compound to be assessed for insecticidal activity.

43. The container of claim 13, wherein the sidewalls of said are formed of plastic.

44. An apparatus for housing insects, comprising a plurality of according to claim 13 affixed together.

45. A container for housing insects, comprising:
(a) a chamber having a floor, sidewalls extending from said floor and an open end portion, wherein the floor of said chamber is formed of a water-permeable material;
(b) a seal member removably attached to said container and configured to close the open end portion; and
(c) a dehydrated insect meal pad contained within said chamber.

46. The container of claim 45, wherein the floor of said container comprises nitrocellulose.

47. The container of claim 45, wherein the meal pad substantially covers the floor of the container.

48. The container of claim 47, further comprising a platform layer partially overlying said meal pad.

49. The container of claim 57, wherein said meal pad is a disk partially overlying said floor of said container.

50. The container of claim 45, further comprising a platform layer, said platform layer having a hole therein, wherein said meal pad substantially overlies said hole.

51. The container of claim 45, wherein said seal is a removable cap.

52. The container of claim 45, wherein said meal pad comprises an insecticide.

53. The container of claim 52, wherein said insecticide is a chemical insecticide selected from the group consisting of pyrethroids, carbamates, diamidides, organophosphates, organochlorines, spinosyns, and chloronicotinoids.

54. The container of claim 52, wherein said insecticide comprises a *Bacillus thuringiensis* toxin.

55. The container of claim 45, wherein said meal pad comprises a test compound to be assessed for insecticidal activity.

56. The container of claim 45, wherein said meal pad comprises a dye that imparts color to insect feces.

57. The container of claim 56, wherein said dye comprises Trypan Blue.

58. The container of claim 45, wherein the sidewalls of said container are formed of plastic.

59. An apparatus for housing insects, comprising a plurality of containers according to claim 45 affixed together.

* * * * *

UNITED STATES PATENT AND TRADEMARK OFFICE
CERTIFICATE OF CORRECTION

PATENT NO. : 6,517,856 B1
DATED : February 11, 2003
INVENTOR(S) : Roe et al.

It is certified that error appears in the above-identified patent and that said Letters Patent is hereby corrected as shown below:

<u>Column 45,</u>
Line 21, should read as follows:
-- 42. The container of claim 13, wherein said meal pad comprises a --.
Line 24, should read as follows:
-- said container are formed of plastic. --.
Line 26, should read as follows:
-- rality of containers according to claim 13 affixed together. --.

Signed and Sealed this

Twenty-first Day of February, 2006

JON W. DUDAS
*Director of the United States Patent and Trademark Office*